US008431666B2

(12) United States Patent
Kennedy et al.

(10) Patent No.: US 8,431,666 B2
(45) Date of Patent: Apr. 30, 2013

(54) INJECTIBLE CYANOACRYLATE-FUNCTIONALIZED POLYISOBUTYLENES

(75) Inventors: Joseph P. Kennedy, Akron, OH (US); Yongmoon Kwon, Weston, FL (US); Suresh Jewrajka, Bankura (IN)

(73) Assignee: The University of Akron, Akron, OH (US)

( * ) Notice: Subject to any disclaimer, the term of this patent is extended or adjusted under 35 U.S.C. 154(b) by 539 days.

(21) Appl. No.: 12/529,113

(22) PCT Filed: Apr. 14, 2008

(86) PCT No.: PCT/US2008/004870
§ 371 (c)(1),
(2), (4) Date: Feb. 23, 2010

(87) PCT Pub. No.: WO2008/127730
PCT Pub. Date: Oct. 23, 2008

(65) Prior Publication Data
US 2010/0144996 A1   Jun. 10, 2010

Related U.S. Application Data

(60) Provisional application No. 60/923,003, filed on Apr. 12, 2007, provisional application No. 61/007,682, filed on Dec. 14, 2007.

(51) Int. Cl.
*C08F 12/28* (2006.01)

(52) U.S. Cl.
USPC ............ 526/310; 525/379; 525/384; 525/386

(58) Field of Classification Search .................. 526/310; 525/379, 384, 386
See application file for complete search history.

(56) References Cited

U.S. PATENT DOCUMENTS

| | | | |
|---|---|---|---|
| 5,448,000 A | 9/1995 | Gullapalli et al. | |
| 6,365,171 B1 | 4/2002 | Kennedy et al. | |
| 2003/0194389 A1 | 10/2003 | Porter | |
| 2010/0130696 A1* | 5/2010 | Kennedy et al. | ............ 525/379 |

FOREIGN PATENT DOCUMENTS

WO     9802468 A1    1/1998

OTHER PUBLICATIONS

Van Dijk, M.A. and Van Den Berg, R., "Ordering Phenomena in Thin Block Copolymer Films Studied Using Atomic Force microscopy", Macromolecules, 28, 6773-6778 (1995).
Antony, Prince, et al., "Atomic Force Microscopic Studies of Novel Arborescent Block and Linear Triblock . . . ", European Polymer Journal, 40, 149-157, (2004).
Pickering, J.P. & Vancso, G.J., "Apparent Contrast Reversal in Tapping Mode Atomic Force Microscope Images on Films of Polystyrene . . . ", Polymer Bulletin 40, 549-554 (1998).
Knoll, A., et al., "Tapping Mode Atomic Force Microscopy on Polymers: Where is the True Sample Surface?", Macromolecules, 34, 4159-4165, (2001).
St. Lawrence, A., et al., "Micromechanical Testing of Polyisobutylene-Polystyrene Block-Type Thermoplastic Elastomers", Rubber Chemical Technology, 74, 601-613, (2001).
Holden, G., et al., "Thermoplastic Elastomers", 3rd Ed., Chapter 12, Hanser publishers, Munich, (1996).
Marks, J.E. (Ed), "Physical Properties of Polymers", Chapter 23, American institute of Physics Press, Woodbury, New York, (1996).
Gent, A.N. (Ed), "Engineering with Rubber", Chapters 1 & 2, Hanser Publishers, New York, (1992).
Klemarczyk, P. "The isolation of zwitterionic initiating species for ethyl cyanoacrylate (ECA) polymerization and the identification . . . ", Polymer, (2001) 42(7), 2837-2848.
Tong, Jiang-Don & R. Jerome, "Communications to the Editor", Macromolecules (2000) 33(5), 1479-1481.
Fetters, L.J., et al., "Reviews", Macromolecules (1994) 27(17), 4639-4647.
Ikada, Y., "Tissue Adhesives in Wound Closure Biomaterials", Chapter 11, "Tissue Adhesives", pp. 317-346, Eds. C. C. Chu, J. Anthony von Fraunhofer, CRC Press, 1997, New York.
Hua, K., Ph.D Dissertation, Effect of Zinc Oxide Particle Size on the Mechanical properties of Carboxylated Nitrile and Carboxylated Styrene . . . , University of Akron, 2003.
Tomlinson, S.K., et al., "The Use of Near-Infrared Spectroscopy for the Cure Monitoring of an Ethyl Cyanoacrylate Adhesive", Vibration Spectroscopy, (2006) 40, 133-141.
Coover, H.W., et al., "Chemistry and Performance of Cyanoacrylate Adhesives", SPE Tech Papers, 5, 92-97, 1959.
Klemarczyk, P., "Surfaces, Chemistry and Applications, Chapter 19, Cyanoacrylate Instant Adhesives", 847-867.
Garcia, Paez, J.M., et al., "Comparative Study of the Mechanical Behaviour of a Cyanacrylate and a Bioadhesive", Journal of Materials Science, 15 (2004) 109-115.
Kennedy, J.P., et al., "Macromers by Carbocationic polymerization . . . ", J. Macromol. Sci-Chem., A28(2), 209-224 (1991).
Mishra, Munmaya K., et al., "Living Carbocationic polymerization . . . ", Polymer Bulletin 17, 207-314 (1987).
Ivan, Bela, et al., "New Telechelic Polymers and Sequential Copolymers by Polyfunctional Initiator-Transfer Agents . . . ", Journal of Polymer Science, vol. 18, 3177-3191 (1980).
Kennedy, Joseph P., et al., "New Telechelic Polymers and Sequential Copolymers by Polyfunctional initiator . . . ", Polymer Bulletin, 4, 67-74 (1981).
Wilczek, Lech & Kennedy, Joseph P., "Electrophillic Substitution of Organosilicon Compounds, II . . . ", J. of Polymer Science, Part A: Polymer Chem., vol. 25, 3255-3265 (1987).
Boston Scientific's Taxus Express 2, "Paclitaxel-Eluting Coronary Stent System", pp. 1-18, Boston Scientific, (2004).

(Continued)

*Primary Examiner* — Robert D. Harlan
(74) *Attorney, Agent, or Firm* — Renner Kenner Greive Bobak Taylor Weber

(57) ABSTRACT

The present invention generally relates to injectible polyisobutylene polymer compounds. More specifically, the present invention relates to injectible polyisobutylene polymer compounds that are designed for various biological and medical applications. In one embodiment, the present invention relates to injectible functionalized polyisobutylene polymer compounds that are designed for various biological and medical applications. In another embodiment, the present invention relates to injectible cyanoacrylate-functionalized polyisobutylene polymer compounds.

32 Claims, 29 Drawing Sheets

OTHER PUBLICATIONS

Lenaerts, V., et al., "Nanoparticles as a Gastroadhesive Drug Delivery System", Bioadhesive Drug Delivery Systems, Chapter 5, pp. 93-104 CRC Press, (1990).

Flory, Paul J. & Refiner, John Jr., "Statistical Mechanics of Cross-Linked Polymer Networks", J. of Chemical Physics, 11(11), Nov. 1943.

Hamed, G.R. & Hua, K.C., "Effect of ZnO Particle Size on the Curing of Carboxylated NBR and Carboxylated SBT", Rubber Research Ctr, The Univ. of Akron, 77(2), 214-226, (2004).

Jain, Mukesh, "Fracture of Styrene Butadience Rubbers of Varying Crosslink Density", Master's Thesis, University of Akron, (1993) Part 1.

Jain, Mukesh, "Fracture of Styrene Butadience Rubbers of Varying Crosslink Density", Master's Thesis, University of Akron, (1993) Part 2.

Vandenberg, R., et al., "Atomic Force Microscopy of Thin Triblock Copolymer Films", Polymer, 35(26), 5778-5781, (1994).

* cited by examiner

INJECTIBLE CYANOACRYLATE-FUNCTIONALIZED POLYISOBUTYLENES

The present invention was made in the course of research that was supported by National Science Foundation (NSF) Grant DMR 02-43314. The United States government may have certain rights to the invention or inventions herein.

FIELD OF THE INVENTION

The present invention generally relates to injectible polyisobutylene polymer compounds. More specifically, the present invention relates to injectible polyisobutylene polymer compounds that are designed for various biological and medical applications. In one embodiment, the present invention relates to injectible functionalized polyisobutylene polymer compounds that are designed for various biological and medical applications. In another embodiment, the present invention relates to injectible cyanoacrylate-functionalized polyisobutylene polymer compounds.

BACKGROUND OF THE INVENTION

Polyisobutylene (PIB) is one of the most biostable and biocompatible rubbers. To that end, certain PIBs have been used in drug-eluting stents for use in coronary arteries. Additional biomedical applications for PIB include, for example, glaucoma-correcting ophthalmic conduits and triflet hear valves, which are currently under intensive clinical evaluation. The spectacular oxidative resistance of PIB has recently been demonstrated by certain PIBs being able to withstand boiling in concentrated nitric acid.

Accordingly, there is a need in the art for additional PIBs that are able to be tailored to one or more specific biological and/or medical applications.

SUMMARY OF THE INVENTION

The present invention generally relates to injectible polyisobutylene polymer compounds. More specifically, the present invention relates to injectible polyisobutylene polymer compounds that are designed for various biological and medical applications. In one embodiment, the present invention relates to injectible functionalized polyisobutylene polymer compounds that are designed for various biological and medical applications. In another embodiment, the present invention relates to injectible cyanoacrylate-functionalized polyisobutylene polymer compounds.

In one embodiment, the present invention relates to an injectible functionalized polyisobutylene compound comprising: a core structure having at least three polyisobutylene arms connected thereto, wherein each of the polyisobutylene arms contain a pendant group selected from a cyanoacrylate group, a —$NH_2$ group, a -$NEt_2$ group.

In another embodiment, the present invention relates to an injectible functionalized polyisobutylene compound comprising: a core structure having at least three polyisobutylene arms connected thereto, wherein each of the polyisobutylene arms contain a pendant cyanoacrylate group and wherein the $M_n$ of the compound is in the range of about 1,500 g/mole to about 4,500 g/mole.

In still another embodiment, the present invention relates to an injectible functionalized polyisobutylene compound comprising: a core structure having at least three polyisobutylene arms connected thereto, wherein each of the polyisobutylene arms contain a pendant —$NH_2$ group and wherein the $M_n$ of the compound is in the range of about 1,500 g/mole to about 4,500 g/mole.

In still another embodiment, the present invention relates to an injectible functionalized polyisobutylene compound comprising: a core structure having at least three polyisobutylene arms connected thereto, wherein each of the polyisobutylene arms contain a pendant -$NEt_2$ group and wherein the $M_n$ of the compound is in the range of about 1,500 g/mole to about 4,500 g/mole.

In still another embodiment, the present invention relates to a method for forming a network from an injectible functionalized polyisobutylene compound, the method comprising the steps of: (A) combining at least one injectible functionalized polyisobutylene compound and at least one initiator compound, wherein the at least one injectible functionalized polyisobutylene compound comprises a core structure having at least three polyisobutylene arms connected thereto and wherein each of the polyisobutylene arms contain a pendant group selected from a cyanoacrylate group, a —$NH_2$ group, a -$NEt_2$ group; (B) loading the combination of the at least one injectible functionalized polyisobutylene compound and at least one initiator compound into an injection device; and (C) injecting the combination of the at least one injectible functionalized polyisobutylene compound and at least one initiator compound into an environment suitable to cause the formation of a polymer network.

DETAILED DESCRIPTION OF THE INVENTION

Figure 1:
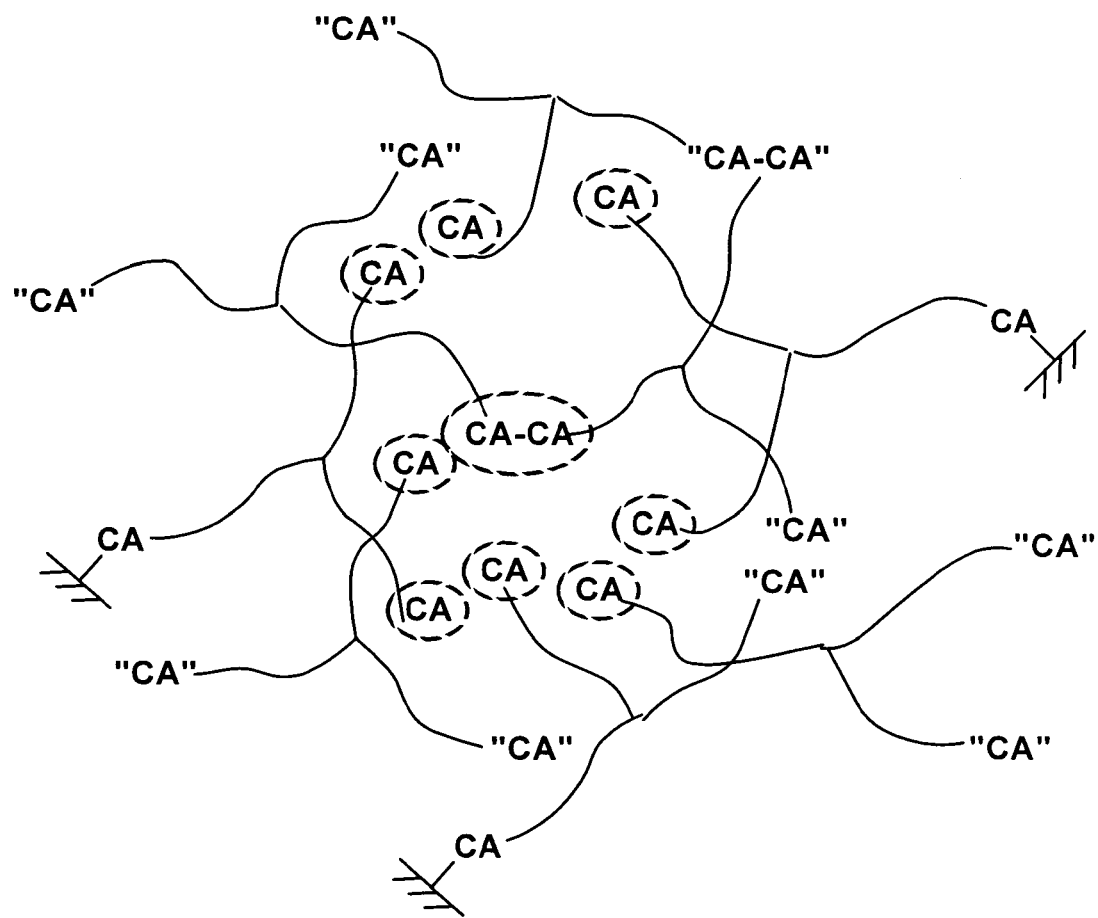
FIG. 1 is an illustration of one idealized structure of a rubbery polyisobutylene (PIB) network formed from the reaction of tri-star polyisobutylenes carrying cyanoacrylate termini (Ø(PIB-CA)$_3$) with nucleophiles.

The present invention generally relates to injectible polyisobutylene polymer compounds. More specifically, the present invention relates to injectible polyisobutylene polymer compounds that are designed for various biological and medical applications. In one embodiment, the present invention relates to injectible functionalized polyisobutylene polymer compounds that are designed for various biological and medical applications. In another embodiment, the present invention relates to injectible cyanoacrylate-functionalized polyisobutylene polymer compounds.

The chemistry of the cyanoacrylate (CA) group is characterized by extreme reactivity and polymerizability. Small-molecule cyanoacrylates, i.e., Me-, Et-, iBu-CA, instantaneously polymerize upon contact with weak nucleophiles, even with water and produce high molecular weight poly cyanoacrylates. The rapid polymerization of cyanoacrylates is exploited by instant industrial adhesives ("superglue") and in specialty adhesives that the FDA permits for use in brain surgery.

Thus, some of the objectives of the present invention include, but are not limited to: (1) to develop an improved and inexpensive synthesis for cyanoacrylate-telechelic polyisobutylenes; (2) to study the effect of reaction conditions on the molecular weight of cyanoacrylate-telechelic polyisobutylenes; (3) to define the viscosity (molecular weight) range at which cyanoacrylate-telechelic polyisobutylene becomes injectible/syringible by various gauge hypodermic needles; (4) to demonstrate the copolymerization of cyanoacrylate-telechelic polyisobutylene with conventional small molecule cyanoacrylates; (5) to demonstrate the crosslinking to rubbers of cyanoacrylate-telechelic polyisobutylene and its copolymers upon injecting into and contact with living tissue; and (6) to explore the physical-chemical-biological properties of the rubbers obtained by the self- and copolymerization of cyanoacrylate-telechelic polyisobutylene upon contact with living tissue.

In one embodiment, the present invention relates to the production of novel clinically useful materials by combining the chemistries of isobutylene (IB) and cyanoacrylates (CAs). The first phase of the present invention relates to the synthesis of manually syringible tri-star polyisobutylenes carrying cyanoacrylate termini ((PIB-CA)$_3$) designed to produce rubbery networks upon injection into living tissue. One potential application for the compounds of the present invention is anti-wrinkle compounds that can be injected under the skin. While not wishing to be bound to any one theory it is believed that when injected under skin with wrinkles, the cyanoacrylate termini present in the compounds of the present invention react with abundantly available nucleophiles (water, proteins, polysaccharides) under the surface of the skin to produce rubbery masses that will stretch the skin and thus reduce/eliminate wrinkles. Another potential application for the compounds of the present invention is for injectible intervertebral disc prostheses.

Thus in one embodiment, the present invention entails the synthesis of tri-star polyisobutylenes carrying cyanoacrylate termini ((PIB-CA)$_3$) with an appropriate bulk viscosity for manual injection. In one embodiment, the appropriate bulk viscosity is achieved with a M$_n$ in the range of 1,500 g/mole to about 4,500 g/mole, or about 2,000 g/mole to about 3,500 g/mole, or about 2,200 g/mole to about 3,300 g/mole, or about 2,500 g/mole to about 3,000 g/mole, or even about 2,800 g/mole. Here, as well as elsewhere in the specification and claims, individual range limits can be combined to form non-stated ranges.

In another embodiment, the appropriate bulk viscosity is achieved with a M$_n$ of about 2,800 g/mole is manually syringible and produces a rubbery polymer masses upon contact with living tissue (e.g., an egg yolk). However, the networks produced by the use of this injectible Ø(PIB-CA)$_3$ exhibit insufficient strength (manual examination). In order to solve this issue the present invention yields PIB networks with increased mechanical properties (e.g., strength). To aid in this objective, a molecular model of a PIB network that is expected to form upon injecting Ø(PIB-CA)$_3$ into living tissue is shown below.

As used throughout the present invention, star polymers arise when at least three polymer arms are linked to a common nucleus or center and each arm carries a functional terminus. In one embodiment, the present invention can utilize any suitable star molecular having at least three arms radiating from a central "core" structure. Suitable central core structures include, but are not limited to, cyclic structures or non-cyclic structures that can be, at a minimum, tri-substituted. In another embodiment, the core is selected from suitable cycloalkanes, cycloalkenes, or aromatics that can be, at a minimum, tri-substituted with polyisobutylene arms. The arms of such compounds can then be further functionalized as is known to those of skill in the art to yield the above-mentioned function terminus on each arm.

As can be seen below, in this model the nucleophilic groups (—OH, —NH$_2$) of proteins react with the cyanoacrylate end groups of Ø(PIB-CA)$_3$ and thus covalently link proteins to the polyisobutylene. In view of the very high reactivity of the cyanoacrylate group towards nucleophiles this reaction is very rapid; indeed bond formation can be, in some embodiments, essentially instantaneous. In polymer chemical terminology this reaction is important to the initiation of anionic polymerization in cyanoacrylates. In one embodiment, since the molar concentration of CA end groups in a high molecular weight Ø(PIB-CA)$_3$ (M$_n$ is approximately 2,000 to 4,000 g/mol) molecule is relatively low, chain growth cannot ensue, and the reaction rapidly terminates by proton capture. This reaction may be regarded a "polymerization without propagation", i.e., initiation rapidly followed by termination. Although polymerization is not expected to proceed, one or perhaps two addition/propagation steps may occasionally occur, particularly when the M$_w$ of Ø(PIB-CA)$_3$ is low. Reaction Schemes 1 and 2, below, outline several possible reactions that may occur between a polymer (P) carrying a nucleophilic group (—OH) and Ø(PIB-CA)$_3$, and water and Ø(PIB-CA)$_3$.

Reaction Scheme 1: Reaction Between P-OH and Ø(PIB-CA)$_3$

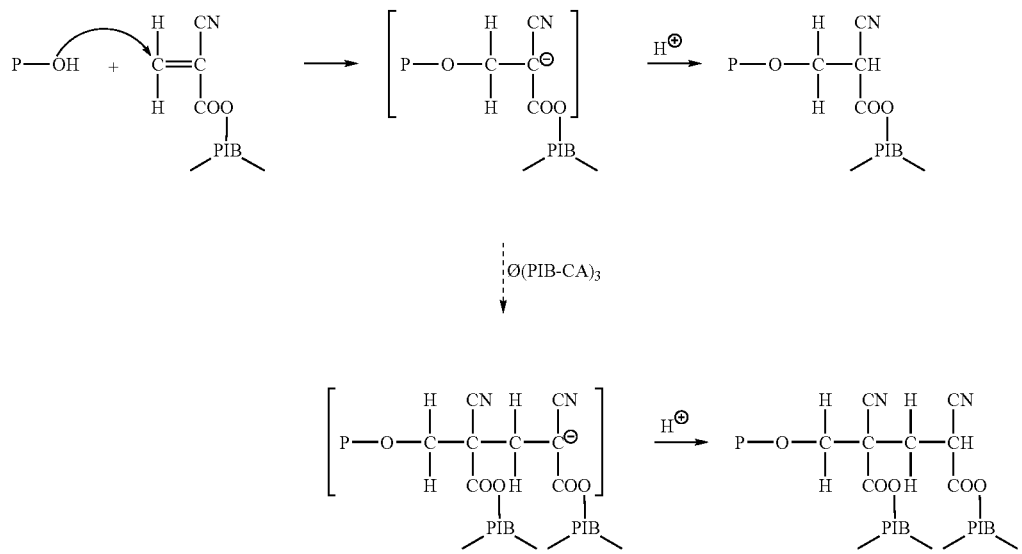

Reaction Scheme 2: Reaction Between P-OH, Ø(PIB-CA)$_3$ and Water

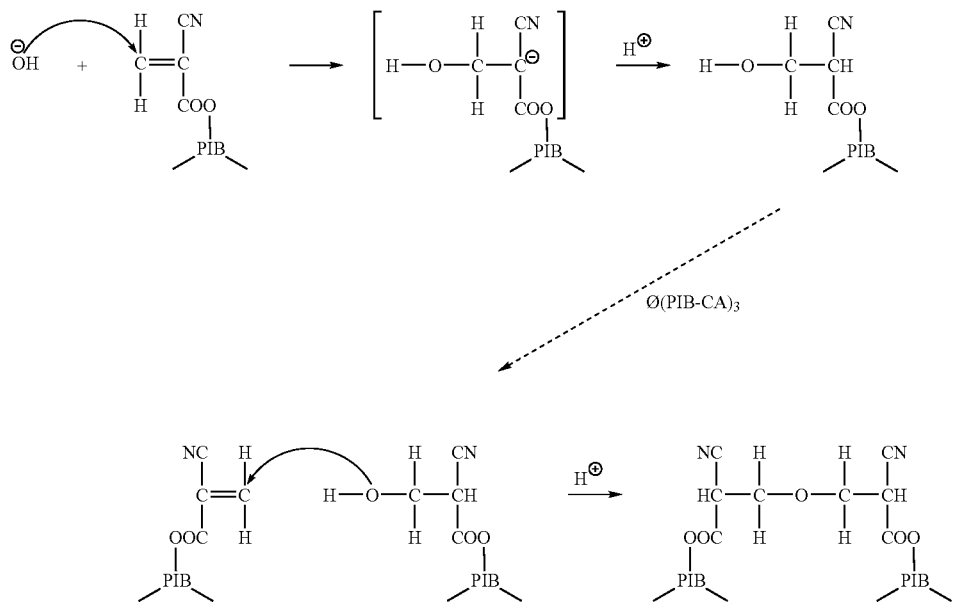

Importantly, the reaction is expected to yield covalent bond(s) between the nucleophilic group (living tissue, surfaces carrying nucleophilic groups) and Ø(PIB-CA)$_3$.

FIG. 1 helps to visualize the microstructure of a crosslinked rubber that arises when Ø(PIB-CA)$_3$ reacts with nucleophiles. The construct contains permanent crosslinks at the center of the tri-arm star Ø(PIB-CA)$_3$. In this embodiment, FIG. 1 represents one idealized structure of a rubbery polyisobutylene (PIB) network formed from the reaction of Ø(PIB-CA)$_3$ with nucleophiles. In FIG. 1 above, CA indicates unattached and/or "useless" HOCH$_2$CH(CN)COO-PIB groups; "dotted" circles and ovals indicate buried CA groups; and the

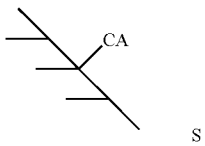

indicate CA groups attached to a surface.

This straightforward chemical scenario, however, can be clouded by a variety of physical factors: (1) due to the low concentration of polar CA groups dispersed in the vast continuum of non-polar PIB matrix, many CA become buried and thus the contact between the reactive functions can be denied. Also, the fraction of buried CA groups may be significant even when low $M_w$ Ø(PIB-CA)$_3$ is used; (2) several CA groups may form polar clusters dispersed within the hostile hydrophobic environment; and (3) adsorbed moisture or liquid water in living tissue will lead to useless dangling PIB chains terminated by HOCH$_2^-$ groups.

Experimentally, it is found that when Ø(PIB-CA)$_3$ having a $M_n$ equal to 2,800 g/mole is contacted with living tissue (e.g., fresh egg yolk) a bolus of polymer is formed essentially instantaneous. However, the tensile strength of the material is judged to be insufficient (by manual examination) for certain intended applications. While not wishing to be bound to any one theory, the low strength is most likely due to the relatively low $M_w$ of the PIB tri-star (2,800 g/mol) used, or possibly due to the absence of permanent entanglements needed for high tensile strength rubbers. The entanglement molecular weight ($M_e$) of PIB is approximately 7,300 g/mol, and the 2,800 g/mole tri-star, whose individual arm $M_w$ is less than about 1,000 g/mole, does not, in certain embodiments, produce sufficient permanent entanglements for high strength. In this embodiment, one cannot increase the $M_w$ of the Ø(PIB-CA)$_3$ to increase the tensile strength of the network because that would increase the viscosity of the starting material, and manual syringibility can be lost (the bulk viscosity Ø(PIB-CA)$_3$ of $M_n$ equal to 2,800 g/mol is close to the limit of manual syringibility).

Given the above, suitable mechanical properties can, in one embodiment, be obtained by increasing the $M_e$ without increasing the $M_w$ of the Ø(PIB-CA)$_3$, by using and/or injecting Ø(PIB-CA)$_3$ together with ethyl cyanoacrylate (EtCA), that is by creating in situ copolymers of Ø(PIB-CA)$_3$ and EtCA. The copolymerization of the CA end groups of Ø(PIB-CA)$_3$ and EtCA should lead to a reduction in the number of useless, buried and/or dangling PIB chains, and thus increase the number of covalently linked PIB segments. By incorporating dangling PIB chains into the networks, the $M_w$ of PIB would increase above a $M_e$ of about 7,300 g/mol and thus the load-bearing capacity of the network should increase.

Figure 2:
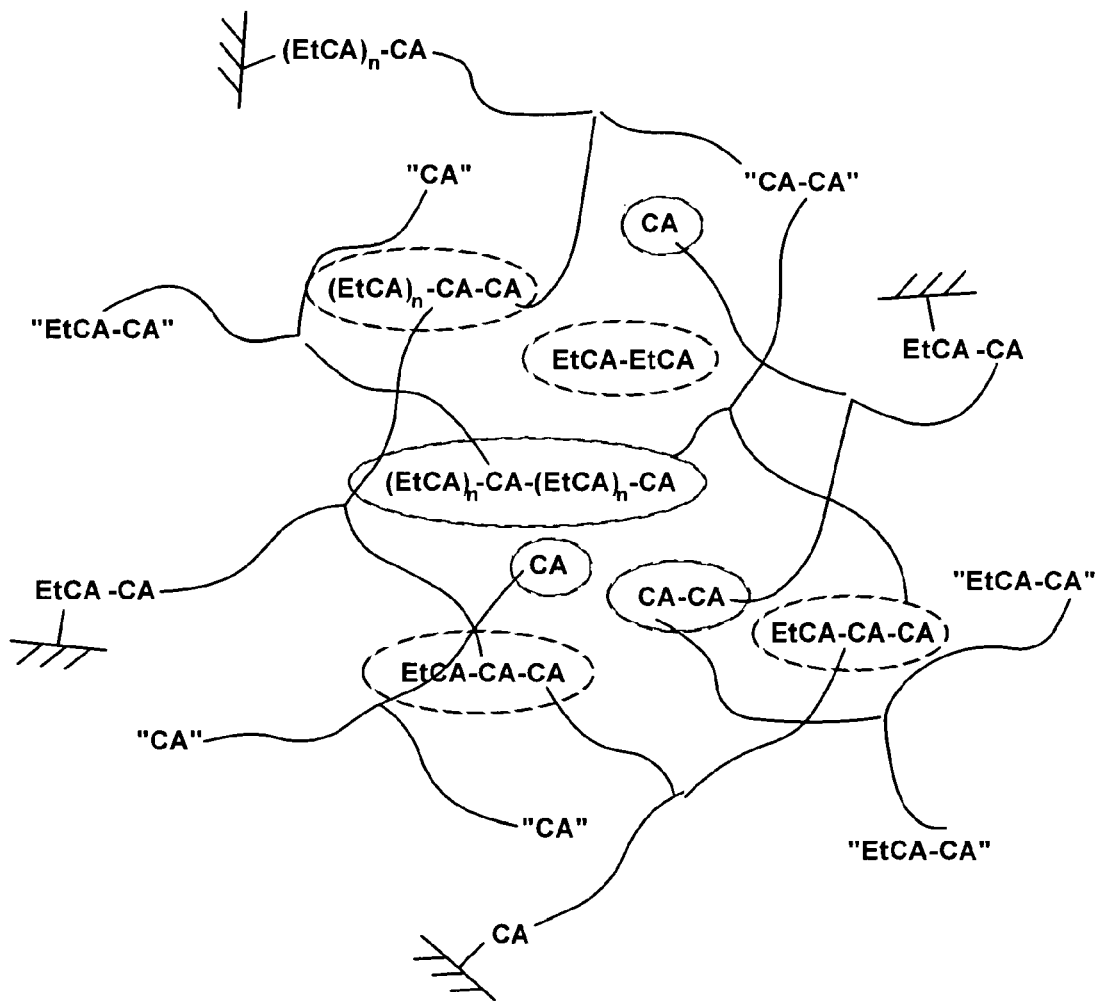
FIG. 2 is an illustration of one idealized structure of a co-network formed from Ø(PIB-CA)$_3$ and ethyl cyanoacrylate (EtCA) upon the reaction with nucleophiles.

FIG. 2 is an illustration of an idealized microstructure of a crosslinked rubber that is expected to form upon contacting a mixture of Ø(PIB-CA)$_3$ and EtCA with nucleophiles present in, for example, living tissue. In FIG. 2, "CA" and "EtCA-CA" indicate unattached and/or "useless" groups (e.g., HOCH$_2$CH(CN)COO-PIB); circles and ovals indicate buried CA or EtCA-CA groups; and the

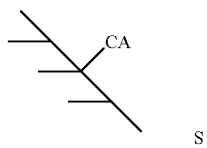

indicate CA or EtCA-CA groups attached to surfaces.

Moreover, the copolymerization of Ø(PIB-CA)$_3$ with relatively large amounts of EtCA forms, in one embodiment, glassy polyEtCA domains ($T_g$ equal to 140° C.) covalently attached to and randomly-dispersed in the PIB matrix; these hard domains desirably reinforce and/or stiffen the rubbery network. The size and concentration of the reinforcing polyEtCA domains can, in one embodiment, be controlled by the amount of EtCA added.

EXPERIMENTAL

Example 1

Materials:

The synthesis and purification of Ø(PIB-CA)$_3$ is known in the art. Benzene, hexanes, methylene chloride, and p-xylene are distilled over CaH$_2$ under a N$_2$ atmosphere. Ethyl 2-cyanoacrylate (EtCA) (from Loctite), anthracene, maleic anhydride, N,N-dimethyl-p-toluidine (DMT) (from Aldrich), and 1,3-dicyclohexylcarbodiimide (DCC) are used as received. Reagent grade tetrahydrofuran, hexanes, and acetone are used for swelling and extraction studies.

Preparation of Films:

0.8 grams of Ø(PIB-CA)$_3$ is dissolved in 3 mL toluene and is added 0 to 20 weight percent EtCA and 1 drop (approximately 37 µmol) of DMT initiator. The solution is poured into a 5×5 cm square Teflon mold, covered with aluminum foil, and the solvent is evaporated in fume hood for 2 days. Finally, the film is vacuum dried for 1 week at 100° C.

Swelling:

Swelling studies are carried out using approximately 30×5×0.3 mm films (see above for film preparation). According to orientating experiments equilibrium swelling is reached after approximately 5 hours of swelling at room temperature. Equilibrium swelling is routinely obtained by placing pre-weighed samples in vials containing approximately 20 mL hexanes, acetone and THF, and gently shaking the systems for 24 hours. Then the samples are removed from the solvents, their surfaces are blotted dry by tissue paper and weighed. The degree of swelling is calculated by using the following equation:

$$d_{sw} = \frac{w_{sw} - w_{dry}}{w_{dry}} \times 100$$

where $w_{sw}$ and $w_{dry}$ are the weights in grams of the swollen and dry network, respectively. Hexane is a good solvent for PIB but not for cyanoacrylate moiety, therefore degree of hexane swelling can give crosslink density information of the networks. Acetone is not good solvent for EtCA, therefore, acetone intake increased with increasing EtCA content in the network.

The average PIB molecular weight between crosslinks ($M_{c,PIB}$) is determined from equilibrium swelling data, using the modified Flory-Rehner equation below:

$$M_c = \frac{\rho_{PIB} V_H (\varphi_{PIB}^{1/3} - \varphi_{PIB}/2)}{-[\ln(1-\varphi_{PIB}) + \varphi_{PIB} + \chi_{IBH}\varphi_{PIB}^2]}$$

where $M_c$ is the molecular weight between effective crosslinks; $\phi_{PIB}$ is the volume fraction of the PIB in the swollen state; $\rho_{PIB}$ is the density of the PIB in the non-swollen state, 0.917 g/cm$^3$; $V_H$ is the molar volume of the hexane, 86.18 cm$^3$/mole; and $\chi_{IBH}$ is the Flory-Huggins solvent interaction parameter, 0.68.

Mechanical (Instron) Testing:

Stress strain properties of micro dumbbell shaped samples are determined by the use of an Instron 5543 tester with 1 kN force and a crosshead speed of 5 mm/min, per the ISO 527 S2 method. The samples are punched 0.22 to 0.35 mm thick solution casting films. Merlin 3.11 software is used for data analysis.

DMTA:

DMTA measurements are carried on film samples by the use of a Rhometric Scientific DMTA V apparatus operating in tension mode. Experiments are performed at 1 Hz with a heating rate of 2° C./min in the 100 to 150° C. range. The setup provides the storage and loss modulus (E' and E"), and the loss factor (tan δ).

FTIR:

FTIR spectra are collected at 4 cm$^{-1}$ resolution with 32 scans, using a Shimadzu FTIR-83 00 spectrometer. Networks are prepared by solution casting Ø(PIB-CA)$_3$ and Ø(PIB-CA)$_3$/EtCA and adding the initiator as discussed above in the film preparation section of this Example.

Results and Discussion—Swelling Studies:

Swelling studies provide valuable insight into the microstructure of complex networks. Table 1 contains initial swelling data. Given the data below, some unexpected trends seem to emerge, and some preliminary observations can be made: (1) acetone (a bad solvent for high $M_W$ PIB and good solvent for polyEtCA) swells the networks, and swelling in acetone is increasing with increasing amounts of EtCA used in co-network synthesis; (2) the extent of swelling in THF is much larger than in hexanes, although hexanes are a better solvent for PIB than THF; (3) swelling in acetone increases in spite of decreasing $M_{c,PIB}$; (4) swelling in both acetone and hexanes suggests the presence of two phases or domains, i.e., co-networks; (5) $M_{c,PIB}$ decreases with increasing EtCA concentration; and (6) the extent of swelling in THF (a good solvent for both PIB and polyEtCA) is very high and increases with increasing EtCA concentration in the co-networks in spite of decreasing $M_{c,PIB}$ (i.e., increasing crosslink density).

TABLE 1

Swelling of Ø(PIB-CA)$_3$ and Ø(PIB-CA)$_3$/EtCA Networks in Various Solvents

| Polymer PIB | Swelling (weight percent) | | | $M_{c,PIB}$ (g/mol)* |
|---|---|---|---|---|
| | Hexanes | Acetone | THF | |
| Ø(PIB-CA)$_3$ | 97 | 15 | 212 | 8060 |
| Ø(PIB-CA)$_3$/EtCA6 | 76 | 17 | 217 | 2950 |
| Ø(PIB-CA)$_3$/EtCA11 | 71 | 18 | 250 | 2860 |
| Ø(PIB-CA)$_3$/EtCA20 | 55 | 26 | 238 | 1690 |

$M_n$ of Ø(PIB-CA)$_3$ is equal to 2,800 g/mol;
*calculated from swelling in hexanes The last digit in the sample codes of column 1 above indicates the weight percent of EtCA used therein.

Figure 3:
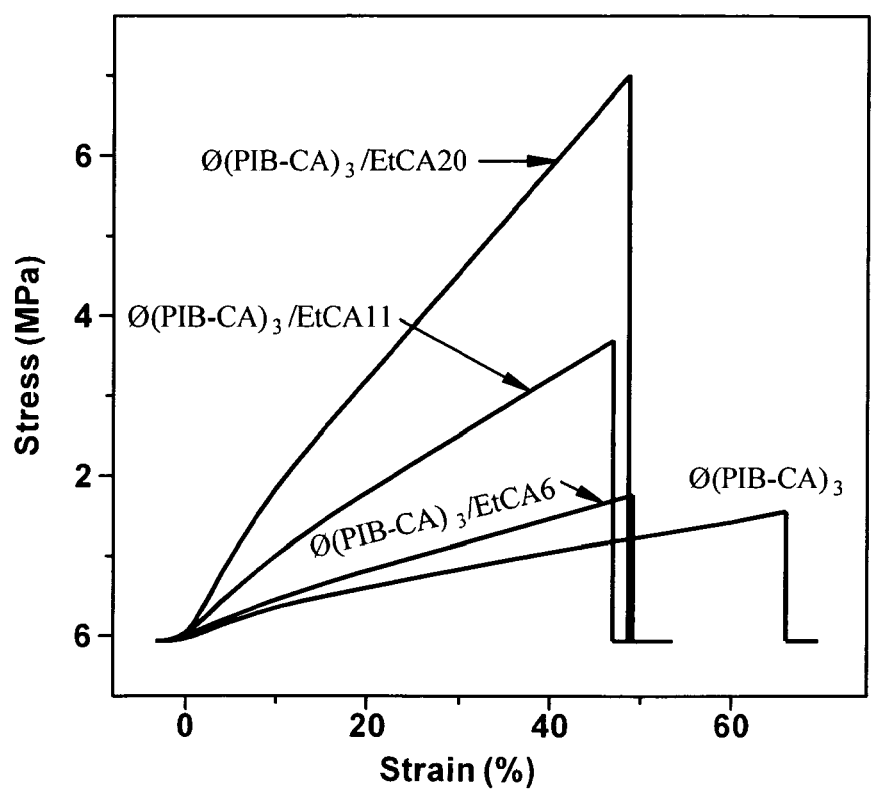
FIG. 3 is a graph illustrating stress-strain traces for various Ø(PIB-CA)$_3$ and Ø(PIB-CA)$_3$/EtCA co-networks from Table 1.

Results and Discussion—Mechanical Properties:

FIG. 3 and Table 2, below, summarize the mechanical properties and $T_g$'s of the Ø(PIB-CA)$_3$ networks and Ø(PIB-CA)$_3$/EtCA co-networks prepared. The first four lines in Table 2 concern PIB networks while the last two lines are obtained with PDMS networks prepared in the absence and presence of EtCA. The data shows the same tendency.

Upon visual examination the samples appear to be optically transparent, slightly yellow homogeneous films.

TABLE 2

Mechanical Properties and $T_g$'s

| Abbreviation of Samples | EtCA Added | Number of Moles** | Tensile (MPa) | Elongation (%) | Young's Modulus (MPa) | $T_g$ (° C.) low/high |
|---|---|---|---|---|---|---|
| Ø(PIB-CA)$_3$ | 0 | 0 | 1.6 | 70 | 4.9 | −12/76° C. |
| Ø(PIB-CA)$_3$/EtCA6 | 6 | 0.47 | 1.8 | 52 | 5.3 | |
| Ø(PIB-CA)$_3$/EtCA11 | 11 | 0.91 | 3.5 | 48 | 11.0 | |
| Ø(PIB-CA)$_3$/EtCA20 | 20 | 1.65 | 7 | 50 | 20.2 | −12/127° C. |
| PDMS-CA$_2$ | 0 | 0 | 0.46 | 115 | 1.02 | |
| PDMS-CA$_2$/EtCA5 | 5 | 1.08 | 1.6 | 80 | 3.65 | |

The last digit in the sample codes of column 1 above indicates the weight percent of EtCA used therein. The molecular weights of the Ø(PIB-CA)$_3$ and PDMS-CA$_2$ are 2800 and 500 g/mol, respectively. Relative to the CA in Ø(PIB-CA)$_3$. *$T_g$'s from tan δ traces.

Figure 4:
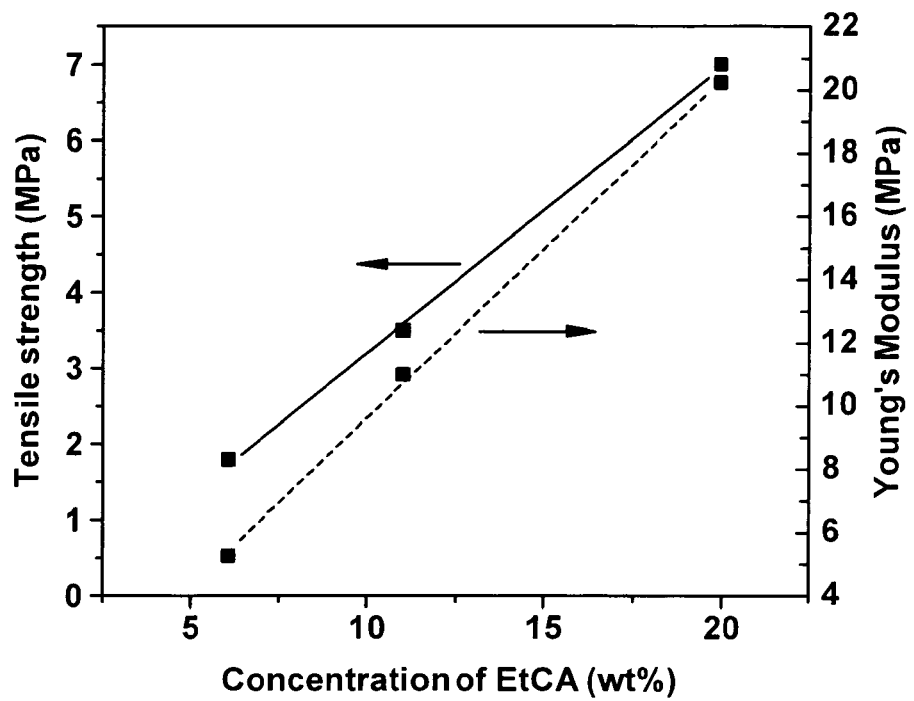
FIG. 4 is a graph illustrating tensile strengths and moduli of various co-networks of Table 1 as a function of EtCA concentration.

Co-networks formed with Ø(PIB-CA)$_3$ plus EtCA exhibit significantly enhanced mechanical properties relative to a control network prepared in the absence of EtCA. Specifically, as shown by the plots in FIG. 4, the tensile strengths and moduli of the co-networks increase linearly with the amount of EtCA. Interestingly, in spite of the different EtCA concentrations, the elongations of the co-networks remain constant at approximately 48% for the samples discussed above (see FIG. 3).

Figure 5:
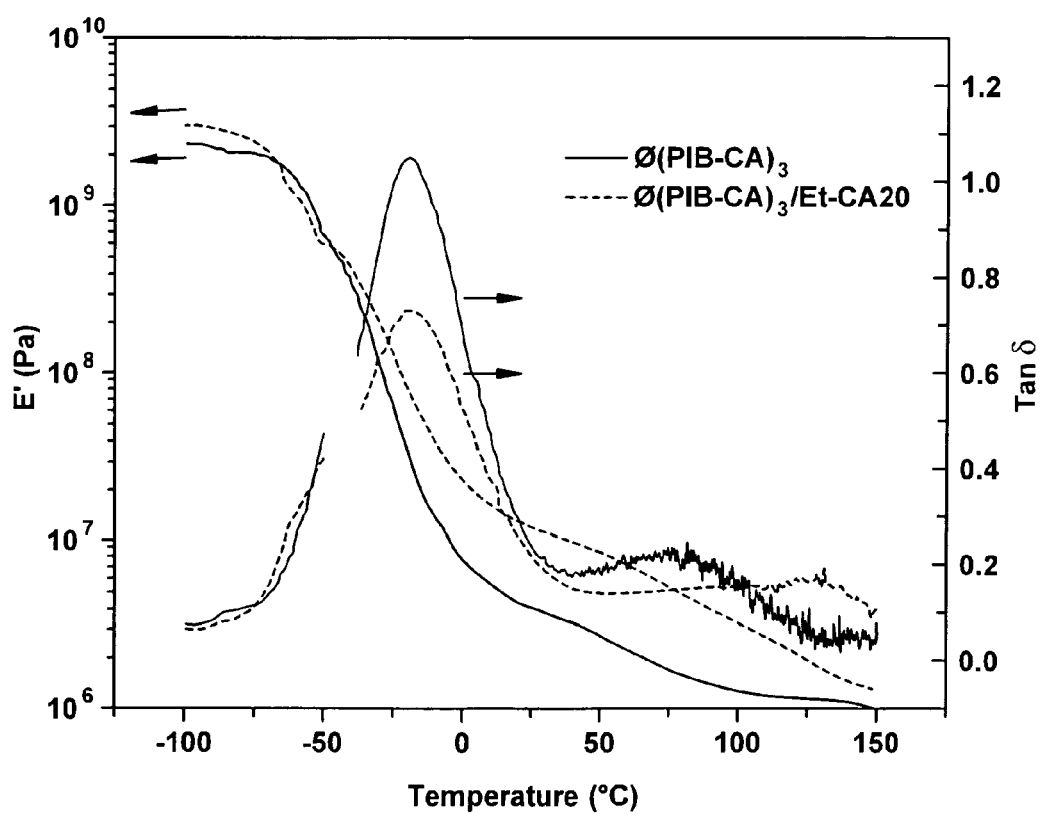
FIG. 5 is a graph illustrating DMTA traces of a Ø(PIB-CA)$_3$ network and a Ø(PIB-CA)$_3$/EtCA20 co-network.

Results and Discussion—DMTA:

FIG. 5 is a graph illustrating the DMTA traces of a representative Ø(PIB-CA)$_3$ network and Ø(PIB-CA)$_3$/EtCA co-network. In the glassy state (below −75° C.), there is little difference between the storage moduli of the Ø(PIB-CA)$_3$ network and Ø(PIB-CA)$_3$/EtCA20 co-network. By increasing the temperature from −100° C. to 0° C., the materials soften and the moduli decrease dramatically. The Ø(PIB-CA)$_3$/EtCA20 co-network, due to its higher crosslink density, exhibits slower relaxation in the glassy transition zone (−75° C. to 0° C.). The loss factor of the co-network is lower than that of the network at −25° C. because of the interaction between the PIB and polyEtCA phases. The plateau modulus starts at approximately 0° C. and extends up to approximately 50° C., where the mechanical relaxation of the polyEtCA phase starts.

Figure 6:
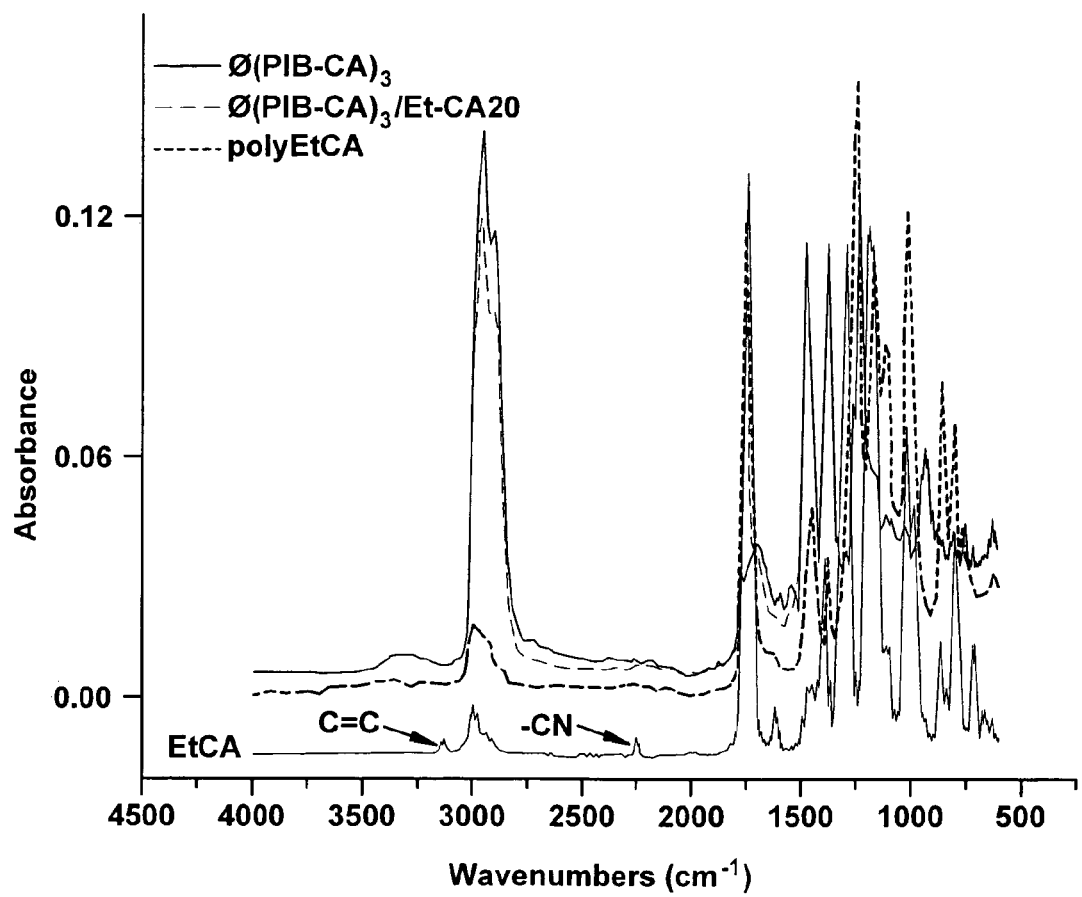
FIG. 6 is a plot of FTIR spectra of polyEtCA (labeled as EtCA), Ø(PIB-CA)$_3$ and Ø(PIB-CA)$_3$/EtCA20 networks.

The prominent loss factor peaks at approximately 83° C. and approximately 130° C. are most likely due to the $T_g$'s of the hard polyEtCA phases in the Ø(PIB-CA)$_3$ network and Ø(PIB-CA)$_3$/EtCA20 co-network, respectively. The glass transition temperature of polyEtCA is reported to be 140° C. The difference in the $T_g$'s is probably due to the molecular weights of the CA domains in the networks. The size of the CA domains is expected to increase by the use of higher concentrations of EtCA. FIG. 6 is a plot of FTIR spectra of polyEtCA (labeled as EtCA), Ø(PIB-CA)$_3$ and Ø(PIB-CA)$_3$/EtCA20 networks.

Figure 7:
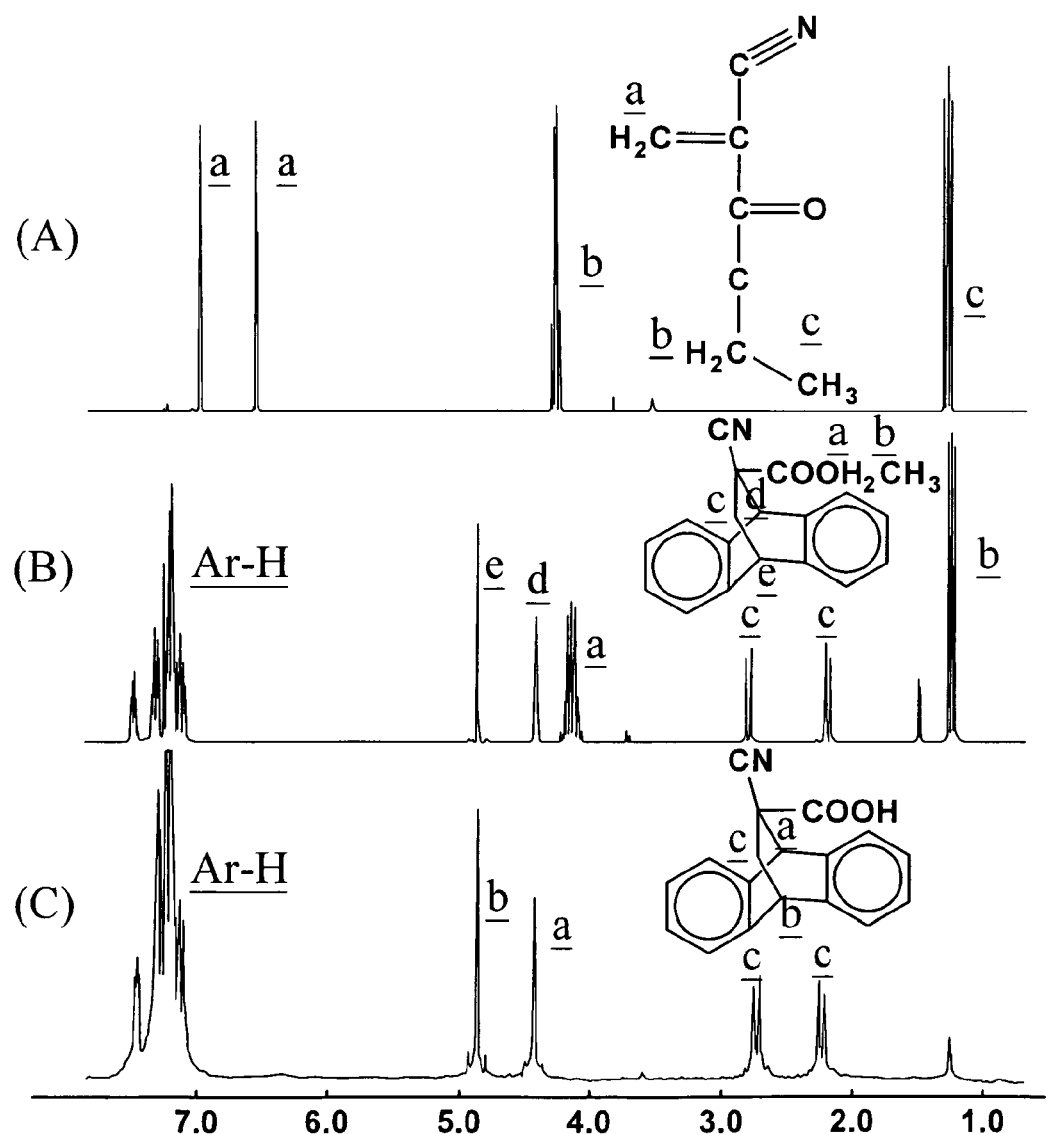
FIG. 7 is a series of $^1$H NMR spectra of (A) ethyl-2-cyanoacrylate; (B) 11-cyano-11-carbomethoxy-9-10-dihydro-9,10-endoethanoanthracene; and (C) 11-cyano-9,10-dihydro-9,10-endoanthracene-carbocxylic acid.

Results and Discussion—FTIR:

FIG. 7 shows the FTIR spectra of EtCA, polyEtCA, and a representative Ø(PIB-CA)$_3$ network and a Ø(PIB-CA)$_3$/EtCA20 co-network. The C—H stretching vibrations of the $CH_2$ and $CH_3$ groups appear in the 2750 to 3000 cm$^{-1}$ range. The sharp CN stretching vibration at 2240 cm$^{-1}$ in the EtCA monomer shifted to 2250 cm$^{-1}$ and broadened in the polymers. While not wishing to be bound to any one theory, these changes are most likely due to the loss of conjugation between the —CN, C═C and C═O groups, and to the presence of the —CN groups in two distinct environments in the polymers. The —C═O stretching vibration at 1740 cm$^{-1}$ increases by increasing the amount of EtCA in the co-network. The stretching vibration of conjugated C═C groups at 2215 cm$^{-1}$ in the Ø(PIB-CA)$_3$ network is due to the aromatic initiator, 1,3,5-tri(2-methoxyisopropyl)benzene. The stretching vibration associated with the ═CH$_2$ groups at 3130 cm$^{-1}$ is absent in the networks, which indicates that the polymerization of cyanoacrylate groups is essentially complete.

EXPERIMENTAL

Example 2

Materials

Trimethyl-1,3,5-benzenetricarboxylate (from Aldrich), methyl magnesium bromide (from Aldrich), potassium t-butoxide (from Aldrich), hydrogen peroxide 35% (from Aldrich), anthracene (from Aldrich), ethyl cyanoacrylate (from Loctite, Part No. 49550), maleic anhydride (from Alfa Aesar), hydrogen bromide (from Aldrich), isobutylene (from Lanxess), methylene chloride (from Lanxess), di-t-butyl pyridine (DtBP, from Aldrich), allyltrimethyl silane (from Aldrich) and TiCl$_4$ (from Aldrich) are used as received. Toluene (from Aldrich), p-xylene (from Aldrich), benzene (from Aldrich), hexanes (from Aldrich) are distilled over CaH$_2$ prior to use.

Synthesis of 1,3,5-Tri(2-Methoxyisopropyl) Benzene

The synthesis of the tri-functional initiator 1,3,5-tri(2-methoxyisopropyl) benzene (tricumyl methoxy, TriCuOMe) is carried out by a Grignard reaction and etherification of trimethyl-1,3,5-benzenetricarboxylate. The product is a white crystalline material, melting point 43° C. to 45° C. The purity of the material is greater than about 98% as confirmed by $^1$H NMR spectroscopy.

Synthesis of Allyl-Terminated Tri-Arm Star PIB

The syntheses of tri-arm star PIBs with low molecular weight (range from 1,000 to 5,000 g/mol) are carried in the N$_2$ filled MBroun LabMaster 130 glove box at −75° C., maintained with an FTS Flexi Cool Immersion Cooler. Thus, in a 500 mL three-neck round bottom flask equipped with an overhead stirrer, is charged with the mixed solvent (n-hexane/methyl chloride 60/40 v/v), proton trap (DtBP, 0.007 M), monomer (IB, 2M), and initiator (TriCuOMe, in the range of 0.022 to 0.05 M). The polymerization is initiated by the rapid addition of a chilled coinitiator (TiCl$_4$, 0.15 M stock solution in methyl chloride), and the reaction continues for 15 minutes. After isobutylene (IB) polymerization 3 fold molar excess allyltrimethyl silane (AllylSiMe$_3$) relative to the tert-chloro groups is added to the reactor. After 60 minutes, the systems are deactivated by addition of a 10 mL of aqueous NaHCO$_3$ solution, and then the volatiles are evaporated in the fume hood overnight. The polymer is dissolved in a 100 mL of hexanes, washed by with water/MeOH (50/50 v/v) solution 3 times, dried over MgSO$_4$ overnight, filtered, and the solvents are evaporated by a rotavap at 50° C. The allyl terminated tri-arm PIBs are clear, colorless, transparent, viscous liquids.

Synthesis of Bromine-Terminated Tri-Arm Star PIB

After the synthesis of narrow molecular weight distribution (MWD) tri-arm star PIB (Ø(PIB-Cl)$_3$) carrying allyl end-groups, bromine-functionalized PIBs (Ø(PIB-Br)$_3$) are prepared by quantitative hydrobromination. Thus, a 100 mL three-neck flask, equipped with a magnetic stirrer and a condenser, is charged with heptane (50 mL) and allyl-telechelic polyisobutylene (10 grams), and air is bubbled through the solution for 30 min at 100° C. Then the solution is cooled to approximately −10° C. and HBr gas is bubbled through the system for about 5 to 10 minutes. After neutralizing the solution with aqueous NaHCO$_3$ (10%), the product is washed 3 times with distilled water. The solution is dried over magnesium sulfate overnight, filtered, and the solvent is removed by using a rotary evaporator at 50° C. The product is a clear viscous liquid. The total yield of the product is 9.5 gram (95% of theory).

Synthesis of 11-Cyano-9,10-Dihydro-9,10-Endoanthracene-Carboxylic Acid (pCA)

The protected cyanoacrylate containing carboxylic acid is prepared by reacting ethyl-2-cyanoacrylate with anthracene followed by ester hydrolysis. Thus, a 500 mL three-neck flask, equipped with a magnetic stirrer and a condenser, is charged with dry SO$_2$-inhibited benzene (300 mL, SO$_2$ is bubbled through the benzene for 30 minutes) and anthracene (50 grams, 0.28 moles) and ethyl-2-cyanoacrylate (30 grams, 0.24 moles), and the solution is refluxed overnight. Next, the solution is concentrated to a volume of about 150 mL and then cooled in a refrigerator. The crystalline adduct (11-cyano-11-carboethoxy-9,10-dihydro-9,10-endoethanoanthracene) is suction-filtered, washed with hexanes, and air-dried. The filtrate is solvent removed and residue is re-crystallized from 200 mL ethanol. The melting is point 98° C. to 100° C. The total yield is 56 grams (0.18 moles) or 75% theory. The purity is approximately 98% by $^1$H NMR spectroscopy (see FIG. 7).

In a 1 liter 3-neck round bottom flask equipped with a overhead stirrer and a condenser is charged 11-cyano-11-carboethoxy-9,10-dihydro-9,10-endoethano-anthracene, ethanol, and a solution of KOH dissolved in water. The solution is stirred at reflux for 2 hours, and the orange colored solution is quenched into water. After overnight standing at room temperature, the suspension is filtered and the filter cake washed with water. The clear yellow filtrate is acidified to a pH 2 by dropwise addition with stirring of 6 N HCl. The solid white product is then collected, washed with water, and air dried to constant weight: melting point 201° C. to 202° C. The yield of pCA is 45 grams (0.16 moles) or 90% of theory. The purity of pCA is at least about 98% by $^1$H NMR spectroscopy (see FIG. 7).

Esterification of Ø(PIB-Br)$_3$ with 11-Cyano-9,10-Dihydro-9,10-Endoanthracene-Carboxylic Acid (pCA):

The esterification of Ø(PIB-Br)$_3$ and 11-cyano-9,10-dihydro-9,10-endoanthracene-carboxylic acid (pCA) is carried out in the presence of tetrabutylammonium hydrogensulfate (TBAHSO$_4$) and potassium fluoride dehydrate (KF.2H$_2$O) by the use of dry tetrahydrofurane (THF) at 60° C. Thus, in a 1 liter three-neck flask, equipped with a overhead stirrer and condenser, is charged with 400 mL dry THF and 0.015 mole of Ø(PIB-Br)$_3$, 0.052 moles of pCA, 0.006 moles of TBAHSO$_4$, and 0.212 moles of KF.2H$_2$O. After stirring overnight at 60° C., the mixture is filtered and precipitated in MeOH. The recovered product is dissolved in hexanes and dried over MgSO$_4$, filtered, and solvent evaporated by a rotavap at 50° C. The product Ø(PIB-pCA)$_3$ is clear, colorless, transparent, viscous liquid, and yields 94% of theory.

Synthesis of Cyanoacrylate-Terminated Tri-Arm Star PIB

The final step for the synthesis of Ø(PIB-CA)$_3$ is de-protection of Ø(PIB-pCA)$_3$ with maleic anhydride. Thus, to a solution of Ø(PIB-pCA)$_3$ in dry p-xylene (deoxygenated by bubbling argon for 30 minutes, and SO$_2$ inhibited) is added maleic anhydride (5 mole percent excess relative to end-groups), a trace of P$_2$O$_5$, and hydroquinone (inhibitor). The mixture is refluxed for 7 hours at 140° C., cooled to room temperature, and the anthracene/maleic anhydride by-product is filtered off. The p-xylene is removed at 50° C. under reduced pressure, the crude product is dissolved in dry hexanes, and filtered to remove the excess maleic anhydride and residual crystalline anthracene/maleic anhydride adduct. The residual p-xylene is removed by repeated addition and evacuation of dry hexanes to yield the pure Ø(PIB-CA)$_3$. The polymer is freeze-dried to remove the last traces of solvents. The product is a light yellow viscous liquid and the yield is 92% of theory.

Synthesis of Networks

The Ø(PIB-CA)$_3$ networks and their co-networks with ethyl cyanoacrylate are prepared in the presence of N,N dimethyl p-toluidine (DMT). Thus, to Ø(PIB-CA)$_3$ (approximately 0.8 grams) dissolved in 3 mL toluene in a 10 mL test tube is added EtCA (0 to 20 weight percent) and 1 drop (approximately 37 μmol) of DMT initiator. The solution is shaken and then poured into a 5×5 cm square Teflon mold, covered with aluminum foil, and the solvent is evaporated in a fume hood for 2 days. Finally, the film is vacuum dried at 100° C. to constant weight and sol fractions are determined in THF.

Instrumentation:

Proton ($^1$H) and carbon ($^{13}$C) NMR spectra are obtained with a Varian Gemini 300-MHz spectrometer using deuterated chloroform as a solvent. The functional groups of the intermediates are verified, and the $M_n$ of polymers is calculated by integration of the resonances associated with the protons in the aromatic ring at δ equal to 7.14 ppm relative to those of protons (CH$_3$) in the PIB chains in the δ equal to 0.7 to 1.2 ppm range. Fourier Transform Infrared Spectroscopy (FTIR) spectra are recorded using a Shimazu FTIR-8300 spectrometer. The data are collected and analyzed with hyper IR 1.51 operating software.

Gel Permeation Chromatography (GPC) eluograms are obtained with a Waters GPC instrument equipped with a series of six Waters Styragel-HR columns ($10^6$, $10^5$, $10^4$, $10^3$, $10^1$ Angstrom pore sizes), a refractive-index detector (Optilab, Wyatt Technology), a dual ultraviolet absorbance detector (model 2487, Waters), a laser light scattering detector (Minidawn, Wyatt Technology), and a viscometer (Viscostar, Wyatt Technology). The samples are dissolved in THF, and the flow rate is 1 mL of THF/min.

Stress strain properties of micro dumbbell shaped samples are determined by the use of an Instron 5543 tester with 1 kN force and a crosshead speed of 5 mm/min, following the ISO 527 S2 method. The samples are 0.22 to 0.35 mm thick, punched from solution cast films. Merlin 3.11 software is used for the data analysis process.

Dynamic mechanical thermal analysis (DMTA) measurements are carried on film samples by the use of a Rhometric Scientific DMTA V apparatus operating in tension mode. Experiments are performed at 1 Hz with a heating rate of 2° C./min in the −100 to 150° C. range. The setup provides the storage and loss modulus (E' and E"), and the loss factor (tan δ).

Oxidative degradation of a networks is tested by preparing films casted from Ø(PIB-CA)$_3$ with a drop of DMT in Teflon molds (5×5 cm) are investigated by the use of nitric acid (65%). Dumbbell shaped samples (0.22 to 0.35 mm thick, 5 mm length) are placed in a 20 mL sample vials filled with nitric acid (65%) for one week and shaken occasionally. After one week the sample is removed from the acid, thoroughly washed by with water, and dried in a vacuum oven for two days at 50° C. The mechanical properties (tensile and elongation) of nitric acid treated Ø(PIB-CA)$_3$ networks are determined by Instron (see above).

Swelling studies are carried out by the use of approximately 30×5×0.3 mm solution cast films. According to orienting experiments equilibrium swelling is reached after approximately 5 hours of swelling at 25° C. Equilibrium swelling is routinely determined by placing pre-weighed samples in vials containing approximately 20 mL hexanes, acetone and THF, and gently shaking the systems for 24 hours at 25° C. The samples are removed from the solvents, their surfaces are blotted dry by tissue paper, and weighed.

Results and Discussion—Improved Synthesis of CA-Telechelic Three-Arm Star PIB, Ø(PIB-CA)$_3$:

As stated above, among the objectives of this research are the synthesis of injectible/syringible CA-telechelic PIBs, and an exploration of the products obtained upon contact with living tissue. It is theorized that the preferred molecular architecture for attaining these objectives is a multi-arm PIB star with CA termini because stars possess a larger number of CA groups than linear prepolymers, and because the viscosity of stars is lower (and therefore easier to inject) than equivalent molecular weight linear structures. In view of these considerations one should set out to prepare CA-telechelic three-arm star PIBs.

The synthesis of CA-telechelic linear (one- and two-CA-ended) and three-arm star PIB is first described by Kennedy et al. in 1991. The syntheses involve the esterification of alcohol-telechelic linear and tri-arm star PIBs by anthracene-protected 2-cyanoacryloyl chloride (i.e., 2-cyanoacryloyl chloride in which the active acryl double bond is protected by anthracene):

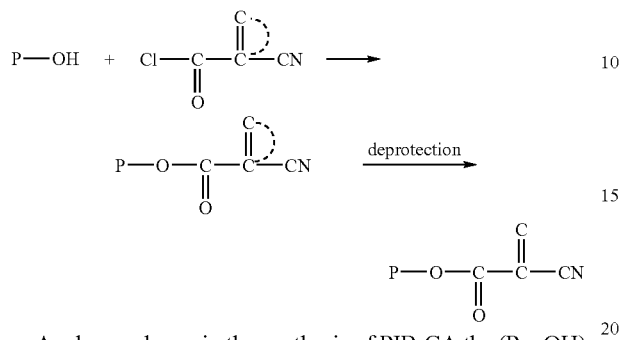

As shown above, in the synthesis of PIB-CA the (P—OH) molecule is generic for mono-, di-, tri-hydroxyl-telechelic PIB alcohols: PIB-OH, HO-PIB-OH and Ø(PIB-OH)$_3$, whose syntheses is known. The dotted semicircle indicates the protection of the acrylic double bond; the protecting group (e.g., anthracene) is removed after esterification.

A thorough analysis of synthetic options indicate that this method still offers an efficient route to Ø(PIB-CA)$_3$ synthesis. However, the present invention discloses and/or involves several improvements to simplify and reduce the cost of the above procedure. Reaction Scheme 3 below summarizes the main steps for the synthesis used in this embodiment for the preparation of three-arm CA-telechelic PIB.

Reaction Scheme 3: Synthesis of Ø(PIB-CA)₃
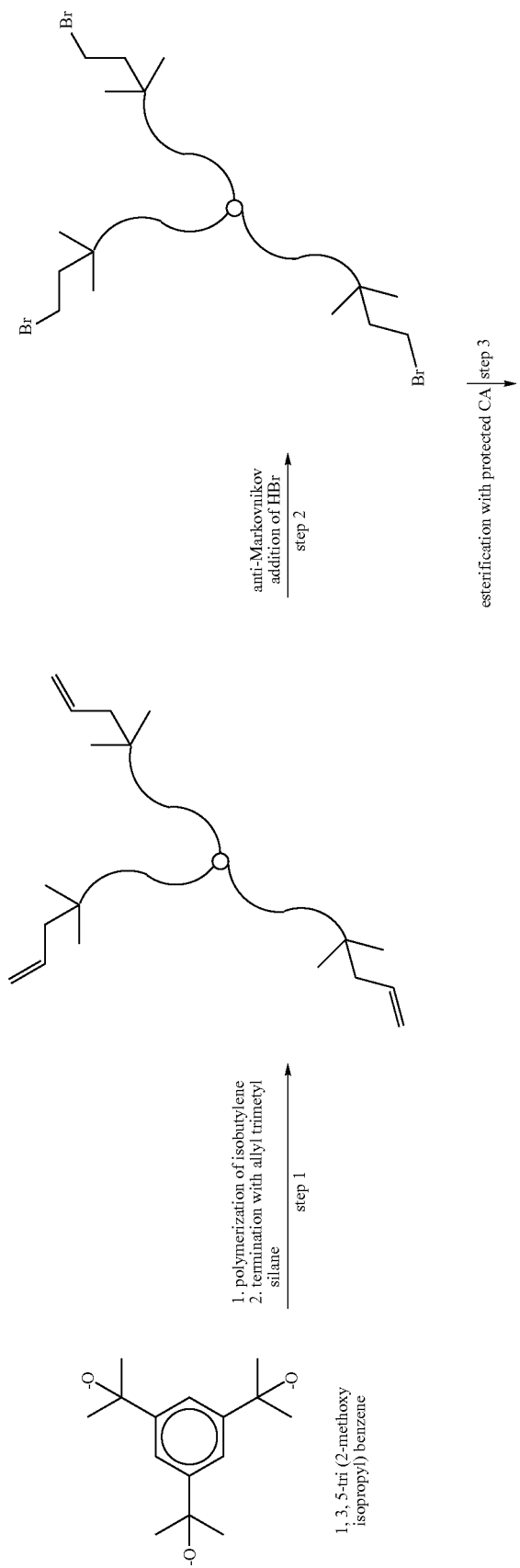

-continued
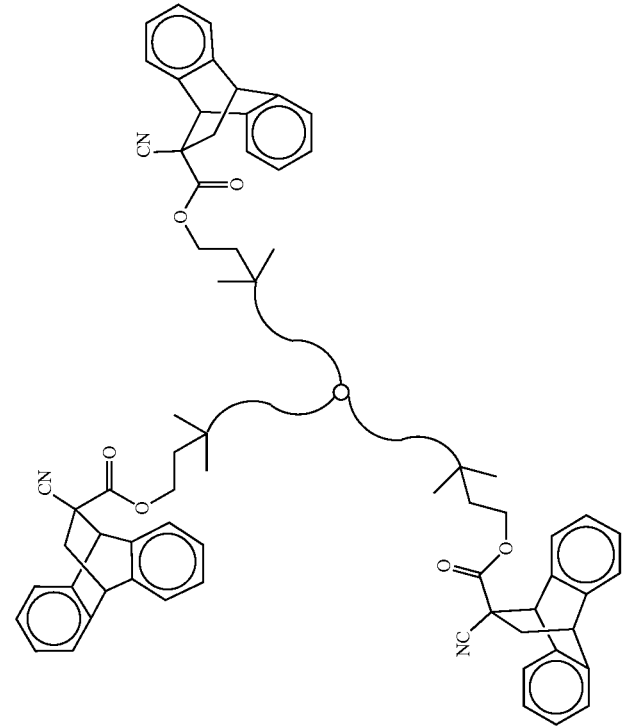
deprotection of CA
step 4
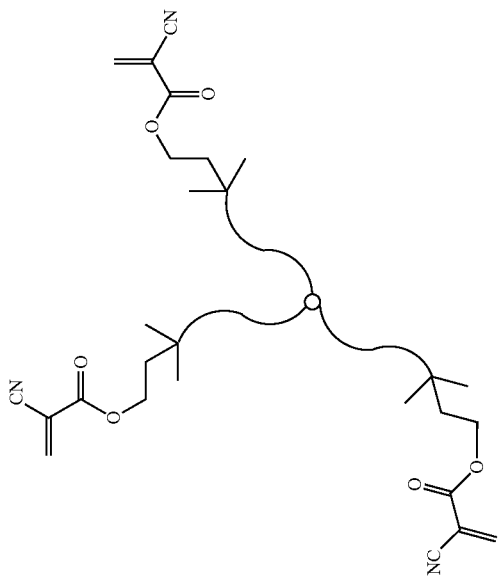

The synthesis starts with the living cationic polymerization of isobutylene by the 1,3,5-tri(2-methoxyisopropyl)benzene/ TiCl$_4$ initiating system. The use of this initiator is preferred to initiators used previously because of its superior stability and ease of purification.

The first product is a Cl-telechelic three-arm star PIB. This Cl-telechelic intermediate is quantitatively converted by reaction with allyltrimethyl silane to allyl-telechelic PIB star in a one-pot reaction. The next step is the conversion of the allyl-telechelic intermediate to a novel primary bromine-telechelic three-arm star PIB. The next step is the esterification of the primary bromide intermediate by anthracene-protected 2-cyano acrylate, which is de-protected in the final step to the target CA-telechelic three-arm PIB star, Ø(PIB-CA)$_3$.

Figure 8:
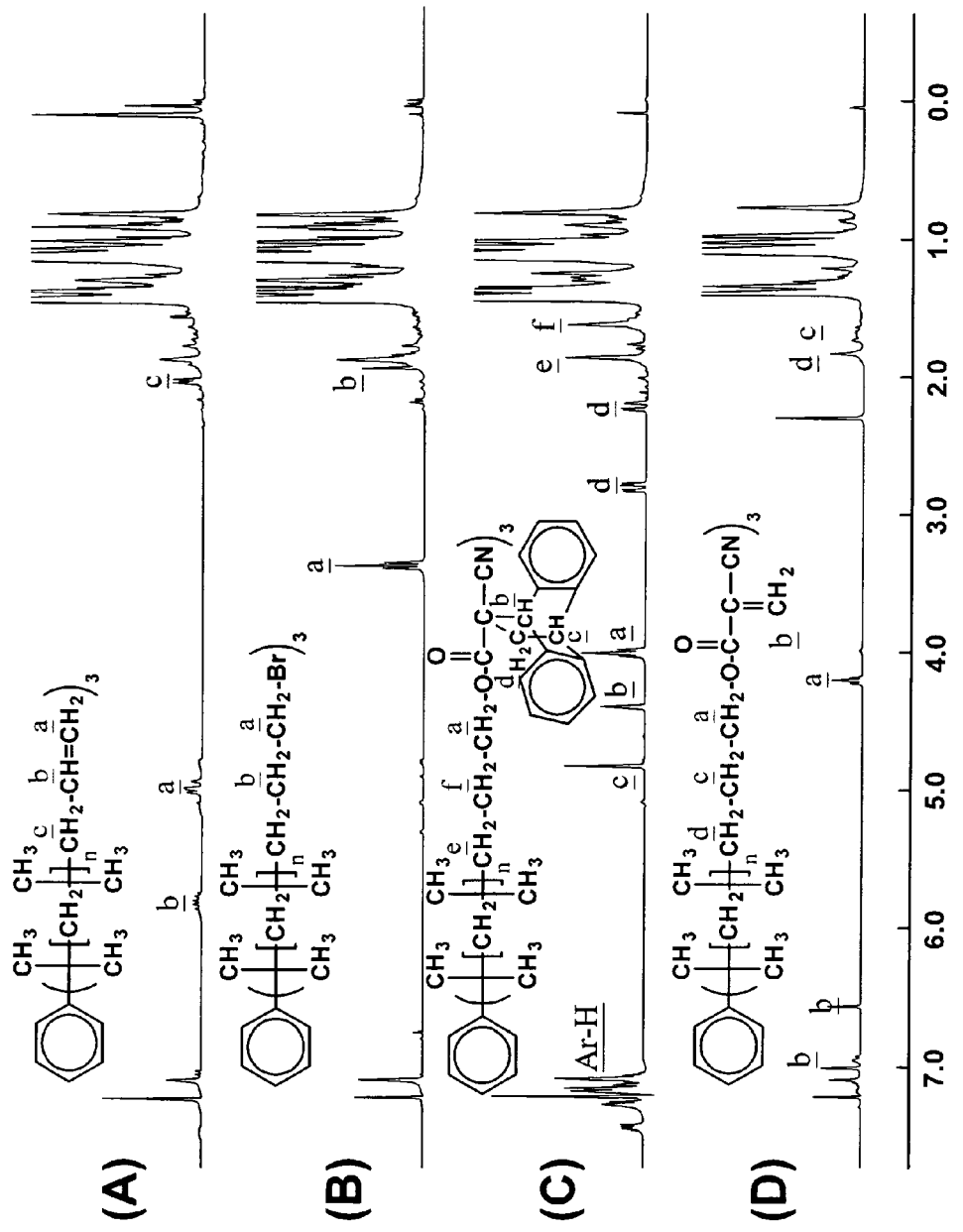
FIG. 8 is a series of $^1$H NMR spectra of tri-arm PIBs with different end groups.

The product is characterized by NMR spectroscopy. FIG. 8 illustrates representative spectra of PIBs with different end groups together with assignments. FIG. 8(A) shows allyl-terminated tri-arm PIB with characteristic resonance signal at δ equal to 5.01 and 5.83 ppm, corresponding to —CH= and =CH$_2$ proton, respectively. The peaks at range from 0.8 to 1.5 are due to the protons on the PIB backbone. After hydrobromination, (FIG. 8(B)) a resonance peak appears at δ equal to 3.37 ppm, corresponding to —CH$_2$— next to the terminal bromo group while double bond disappears. Esterification is carried out with bromine-terminated PIB and carboxylic acid formed the protected cyanoacrylate, and the $^1$H NMR spectrum of the product is shown in FIG. 8(C). The resonance signal of δ equal to 4.02 ppm is due to the —CH$_2$—O—, and 6 equal to 2.19, 2.78, 4.43, and 4.86 ppm are due to the protons from the protection group. In FIG. 8(D) the peak at 4.24 ppm is due to the —CH$_2$—O—, and at δ equal to 7.03 and 6.61 ppm are due to the two protons on the carbon atom of the double bond CH$_2$=C(CN)COO—. The peaks at δ approximately 7 ppm and 2.32 ppm are due to xylenes in the product, which are often hard to remove. In order to obtain pure product, repeated hexanes addition and evacuation and freeze-vacuum-thaw are conducted several times. According to the $^1$H NMR spectrum the number of arms emanating from the central aromatic core is approximately 2.8.

The protected cyanoacrylate adduct, 11-cyano-9,10-dihydro-9,10-endoanthracene-carboxylic acid (pCA) is prepared from Et-CA (ethyl-2-cyanoacrylate) with anthracene and ester hydrolysis. FIG. 8, above, shows $^1$H spectra of ethyl-2-cyanoacrylate, 11-cyano-11-carbomethoxy-9-10-dihydro-9, 10-endoethanoanthracene, and 11-cyano-9,10-dihydro-9,10-endoanthracene-carboxylic acid with assignments, respectively. After Diels-Alder reaction of ethyl-2-cyanoacrylate with anthracene, the double bond on the ethyl-2-cyanoacrylate shown at δ equal to 4.3 ppm disappears (see FIG. 7). The total yield of the final product, pCA is 45 grams or approximately 70% of theory.

Results and Discussion—Syringibility

Experimentation is carried out to obtain various molecular weight Ø(PIB-CA)$_3$. The molecular weight of the Ø(PIB-CA)$_3$ is controlled by controlling the [monomer]/[initiator] ratio. It is soon determined that the viscosity of Ø(PIB-CA)$_3$ is too high for syringibility if the molecular weight is in excess of approximately 5,000 g/mol. It is determined that Ø(PIB-CA)$_3$ of M$_n$ equal to 4,000 g/mol could be injected by a 10 gauge hypodermic needle but not by an 18 gauge needle. Reducing the molecular weight to approximately 3,000 g/mol, gave a free flowing product that is readily syringible by slight manual pressure through an 18 gauge needle.

Figure 9:
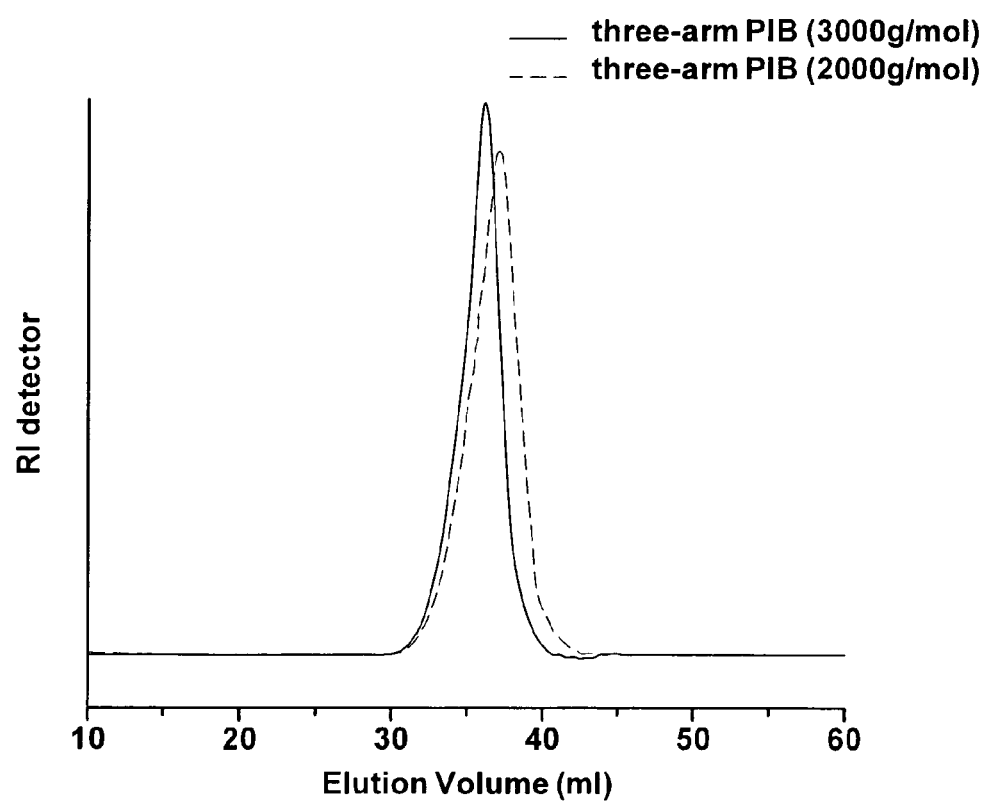
FIG. 9 is a graph illustrating GPC traces of three-arm allyl terminated-PIBs.

The structure of Ø(PIB-CA)$_3$ is determined by NMR spectroscopy and the molecular weight distributions by GPC. FIG. 9 shows GPC eluograms of Ø(PIB-allyl)$_3$ of M$_n$ equal to 2100 and 3100 g/mol, and M$_w$/M$_n$ equal to 1.21 and 1.20, respectively. GPC measurements are carried out by the use of Ø(PIB-allyl)$_3$. GPC measurements could not completed with Ø(PIB-CA)$_3$ because the high polymerization activity of this product prevented measurements in the presence of ubiquitous protic impurities. According to GPC evidence, the products are of narrow distribution as well as homogeneous well-defined materials.

FIG. 9, below, shows GPC eluogram of PIBs with molecular weight 2,000 g/mol and 3,000 g/mol with 1.21 and 1.20 polydispersity index, respectively. The number of arms is in the range of from 2.5 to 2.9, as analyzed by $^1$H NMR.

Results and Discussion—Contact with Living Tissue:

Small quantities (approximately 0.001 grams) of Ø(PIB-CA)$_3$ of 4,000 g/mol are injected into fresh chicken eggs, the eggs are opened and the bolus of the material formed examined.

Orienting observations are made to elucidate the polymerization behavior of Ø(PIB-CA)$_3$ upon contact with proteinaceous tissue. Thus, small quantities (approximately 0.01 grams) of Ø(PIB-CA)$_3$ (M$_n$ equal to 4,000 g/mol) are injected by a hypodermic needle onto the egg white of fresh chicken eggs in a 200 mL beaker, and the system is covered with Parafilm to avoid loss of moisture. After 1 and 7 days product harvested after a day is a soft rubber and dissolved in THF; however, the rubber obtained after 7 days swelled but did not dissolve in THF. Efforts to manually separate (scraping off) this rubber from the egg white failed. These observations indicate possible polymerization of the CA groups of Ø(PIB-CA)$_3$ by the egg protein. However, the rate of the reaction is low, because of the low molar CA concentration and unfavorable contact between the mostly non-polar Ø(PIB-CA)$_3$ and the polar surface of the proteinaceous material.

Results and Discussion—Oxidative Resistance:

The oxidative resistance to concentrated HNO$_3$ of crosslinked PIB rubber formed of Ø(PIB-CA)$_3$ is investigated upon exposure to nucleophiles. Thus, dumbbells punched from films obtained by contacting Ø(PIB-CA)$_3$ with DMT are placed into concentrated nitric acid (65%) and the systems are gently stirred for a week at room temperature. The samples are recovered, washed with water and the mechanical properties of samples are compared before and after exposure to nitric acid. The tensile stress and elongation of representative nitric acid untreated samples are 1.6 MPa and 70%, respectively. The properties of nitric acid treated samples are not much different: 1.5 MPa and 90%, respectively. Additional evidence for the oxidative resistance of co-networks formed of Ø(PIB-CA)$_3$/Et-CA mixtures upon contact with nucleophiles, is obtained by FTIR spectroscopy. The same oxidative degradation experiment with Ø(PIB-CA)$_3$/EtCA20 is carried in the same conditions for a week.

EXPERIMENTAL

Example 3

Materials:

The material used and their sources together with the synthesis of Ø(PIB-CA)$_3$ (2800 g/mol, M$_w$/M$_n$=1.2) is described above. Co-networks are abbreviated by Ø(PIB-CA)$_3$/Et-CA plus a number indicating the weight percent Et-CA used in the synthesis, e.g., Ø(PIB-CA)$_3$/Et-CA50.

Procedures and Instruments:

Ø(PIB-CA)$_3$ networks and their co-networks with Et-CA are prepared in the presence of N,N-dimethyl-p-toluidine (DMT). A typical copolymerization is carried out as follows: to Ø(PIB-CA)$_3$ (approximately 0.8 grams, M$_n$ equal to 2800 g/mol) dissolved in 3 mL toluene in a 10 mL test tube is added Et-CA (0 to 50 weight percent) and 1 drop (approximately 37 µmol) of DMT initiator. The solution is shaken, poured into a 5×5 cm square Teflon mold, covered with aluminum foil, and the solvent is evaporated in a fume hood for 2 days. Finally, the film is vacuum dried at 100° C. to constant weight. Soluble fractions are determined by the use of THF.

Swelling studies are carried out by the use of approximately 30×10×0.3 mm solution cast films. According to orienting experiments equilibrium swelling is reached after approximately 2 hours of swelling at 25° C. Equilibrium swelling is determined by placing pre-weighed samples in vials containing approximately 20 mL hexanes, acetone, and THF, and gently shaking the systems for 24 hours at 25° C. The samples are removed from the solvents, their surfaces are blotted dry by tissue paper, and weighed. The degree of swelling is calculated by:

$$d_{sw} = \frac{w_{sw} - w_{dry}}{w_{dry}} \times 100$$

where $w_{sw}$ and $w_{dry}$ are the weights in grams of the swollen and dry network, respectively.

The average PIB molecular weight between crosslinks ($M_{C,PIB}$) is determined from equilibrium swelling data, using the modified Flory-Rehner equation below:

$$M_c = \frac{\rho_{PIB} V_H (\varphi_{PIB}^{1/3} - \varphi_{PIB}/2)}{-[\ln(1 - \varphi_{PIB}) + \varphi_{PIB} + \chi_{IBH} \varphi_{PIB}^2]}$$

where $M_c$ is the molecular weight between effective crosslinks; $\phi_{PIB}$ is the volume fraction of the PIB in the swollen state; $\rho_{PIB}$ is the density of the PIB in the non-swollen state, 0.917 g/cm³; $V_H$ is the molar volume of the hexane, 86.18 cm³/mole; and $\chi_{IBH}$ is the Flory-Huggins solvent interaction parameter, 0.68.

Oxidative degradation of Ø(PIB-CA)$_3$/Et-CA films (see above) is studied by contact with nitric acid. The films are placed in 20 mL sample vials filled with nitric acid (65%) for one week and shaken occasionally. After one week the films are removed from the acid, washed by distilled water, and dried in a vacuum oven for two days at 50° C. FTIR spectra of the films are compared before and after nitric acid treatment.

Stress strain properties of micro dumbbell shaped samples are determined by an Instron 5543 tester with 1 kN force and a crosshead speed of 5 mm/min, following the ISO 527 S2. Samples of 0.22 to 0.35 mm thick are punched from solution cast films. Merlin 3.11 software is used for data analysis.

The AFM images of Ø(PIB-CA)$_3$/Et-CA50 co-network are recorded by using a multimode scanning probe microscope (Park Scientific Autoprobe CP) operated in the tapping mode using micro-fabricated Si (type NCH) cantilevers. AFM measurements are performed on samples after annealing at 120° C. overnight and the images are obtained at room temperature in air.

Dynamic mechanical thermal analysis (DMTA) is carried out on films using a Rhometric Scientific DMTA V apparatus operating in tension mode. Experiments are performed at 1 Hz with 2° C./min heating rate in the −100 to 150° C. range. The storage and loss moduli (E' and E"), and the loss factor (tan δ) are determined.

Results and Discussion—Swelling Studies:

Table 3 shows sol fractions, weight percent hexanes, acetone and THF uptake together with the molecular weight of the PIB segment between crosslinks, $M_{c,PIB}$, for a homo-network and four co-networks.

TABLE 3

Swelling of Ø(PIB-CA)$_3$ and Ø(PIB-CA)$_3$/EtCA Networks in Various Solvents

| Polymer PIB | Sol Fraction % (THF) | Swelling (weight percent) | | | $M_{c,PIB}$ (g/mol)* |
|---|---|---|---|---|---|
| | | Hexanes | Acetone | THF | |
| Ø(PIB-CA)$_3$ | 10.5 | 97 | 15 | 212 | 8060 |
| Ø(PIB-CA)$_3$/EtCA6 | 10.7 | 76 | 17 | 217 | 2950 |
| Ø(PIB-CA)$_3$/EtCA11 | 9.9 | 71 | 18 | 250 | 2860 |
| Ø(PIB-CA)$_3$/EtCA20 | 8.6 | 55 | 26 | 238 | 1690 |
| Ø(PIB-CA)$_3$/EtCA50 | 7.1 | 33 | 80 | 262 | 1430 |

$M_n$ of Ø(PIB-CA)$_3$ is equal to 2,800 g/mol;
*calculated from swelling in hexanes The last digit in the sample codes of column 1 above indicates the weight percent of EtCA used therein.

The percent soluble fractions are determined by extraction of samples of each polymer with THF. As seen in Table 3, sol fraction of networks is reduced as the amount of Et-CA in the co-networks is increased.

Hexane is a good solvent for PIB but a non-solvent for poly(Et-CA); acetone is non-solvent for PIB; however, it is a good solvent for the poly(Et-CA) moiety. THF is a good solvent for both segments. The fact that swelling in hexanes decrease with increasing Et-CA content is readily explained by the decrease $M_{c,PIB}$. In contrast, the fact that swelling in acetone increases with increasing Et-CA content, indicates co-continuity of the PIB and poly(Et-CA) domains, i.e., the presence of co-networks. The fact that swelling in THF is much higher than in hexanes (a better solvent for PIB than THF), and that swelling increases with increasing Et-CA contents in spite of decreasing $M_{c,PIB}$ (increasing crosslink density), also suggests co-continuous domains. The presence of hard poly(Et-CA) phase dispersed in the soft PIB matrix is desirable for reinforcement of the rubbery co-network.

$M_{c,PIB}$ of co-networks is determined using Flory-Rehner equation. The $M_{c,PIB}$ is decreased as the Et-CA increase in the networks. The network of Ø(PIB-CA)$_3$ with $M_{c,PIB}$ 8060 g/mol is almost 8 times bigger than the molecular weight of one branch of Ø(PIB-CA)$_3$ which is 930 g/mol. This indicates that the Ø(PIB-CA)$_3$ network contains unreacted CA end-group; i.e., one out of three arms probably remains as dangling chains and two arms act as only extensions of the chain but probably do not crosslink. However, the $M_{c,PIB}$ is decreased to 1430 g/mol when 50 weight percent of Et-CA is copolymerized, indicating that the dangling chains reduced and improved crosslink formation by addition of Et-CA. Thus, $M_{c,PIB}$ together with sol fraction studies strongly demonstrate the crosslink formation of the Ø(PIB-CA)$_3$ enhances by addition of Et-CA.

Figure 10:
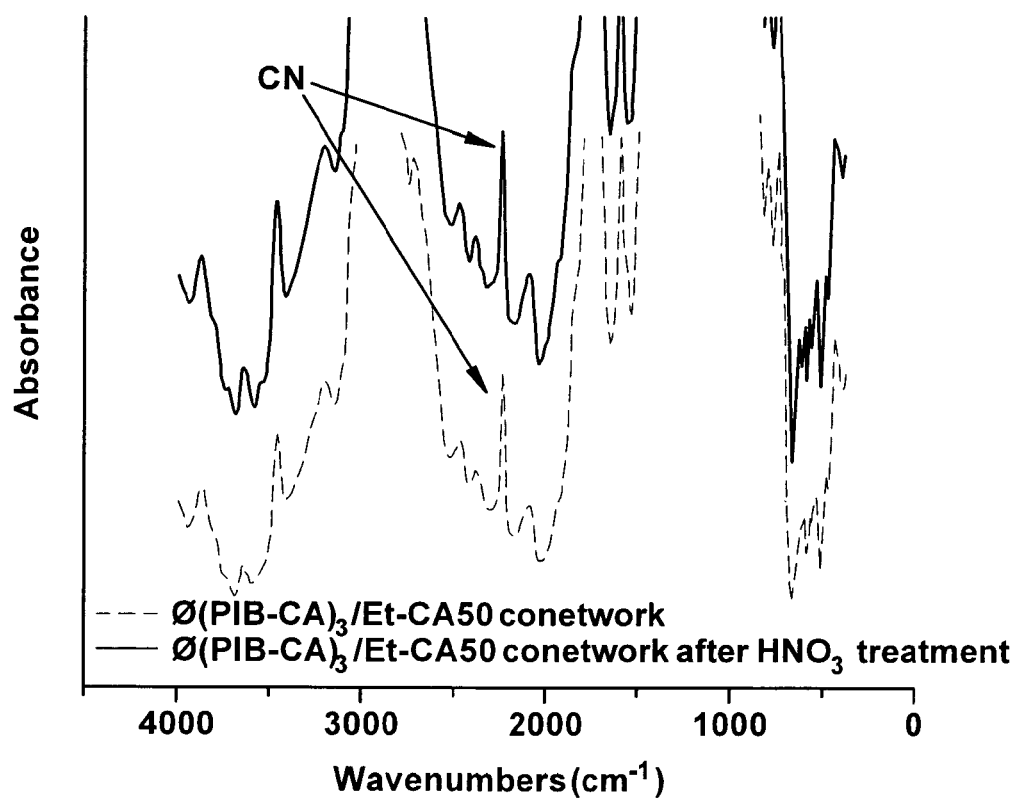
FIG. 10 is an FTIR spectra of the Ø(PIB-CA)$_3$/Et-CA50 co-network before and after nitric acid treatment.

Results and Discussion—Oxidative Resistance:

FIG. 10 shows FTIR spectra of the Ø(PIB-CA)$_3$/Et-CA50 co-network before and after nitric acid treatment. The co-network is prepared with high concentration of Et-CA (50 weight percent Et-CA), so that the —C≡N group can be easily observed the effect of concentrated nitric acid. The sharp —C≡N stretching vibration at 2240 cm⁻¹ of the co-network did not change after nitric acid treatment, which indicates the absence of oxidative degradation. The visual appearance of the samples remained unchanged.

Figure 11:
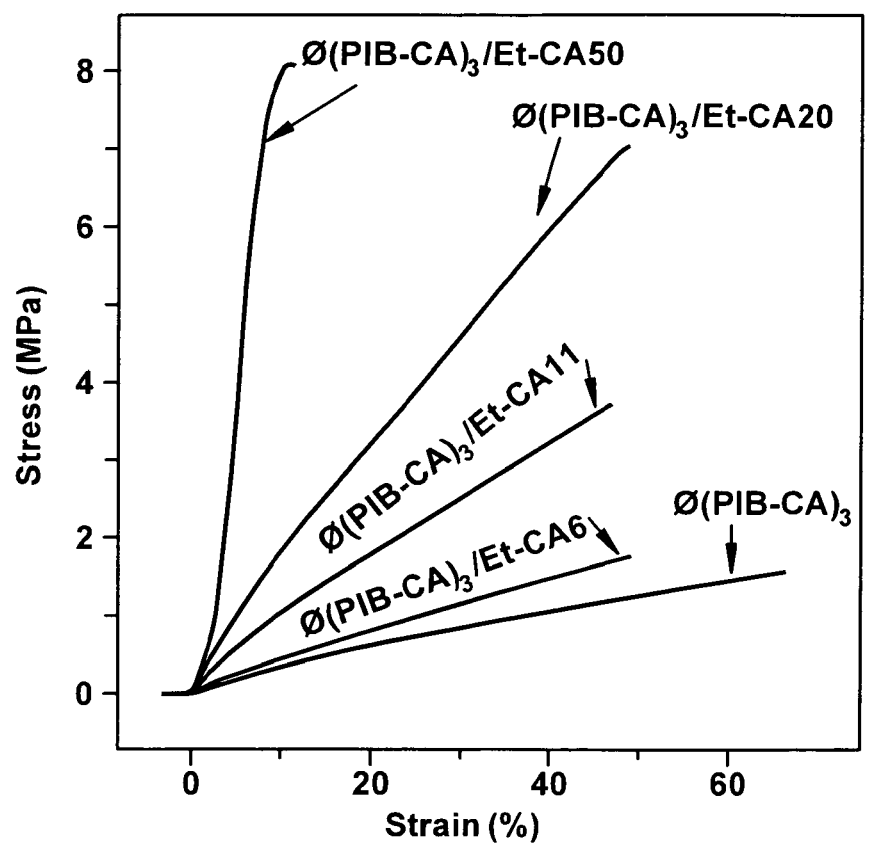
FIG. 11 is a graph illustrating stress-strain traces for various Ø(PIB-CA)3 and Ø(PIB-CA)3/EtCA co-networks from Table 4.

Results and Discussion—Mechanical Properties of Networks and Co-Networks:

Table 4 and FIG. 11 summarize $T_g$'s and select mechanical properties of a Ø(PIB-CA)$_3$ network and three Ø(PIB-CA)$_3$/Et-CA co-networks prepared with 6, 11, 20, 50 weight percent of Et-CA. The samples are optically transparent, homogeneous slightly yellow films. The co-networks of Ø(PIB-CA)$_3$ with 6 to 20 weight percent Et-CA are soft rubbery materials, while that obtained with 50 weight percent of Et-CA is leathery.

Relative to a network prepared of Ø(PIB-CA)$_3$ in the absence of Et-CA, co-networks obtained with Ø(PIB-CA)$_3$ plus Et-CA exhibit significantly enhances tensile strengths and moduli, and somewhat lower elongations. Interestingly, in spite of the different Et-CA concentrations, the elongations of the co-networks obtained with 6 to 20 weight percent Et-CA remain constant at approximately 48% in the range investigated. A crosslinked nitrile rubber and SBR show similar percent elongation, approximately 1000%, with various crosslink densities of the networks.

Figure 12:
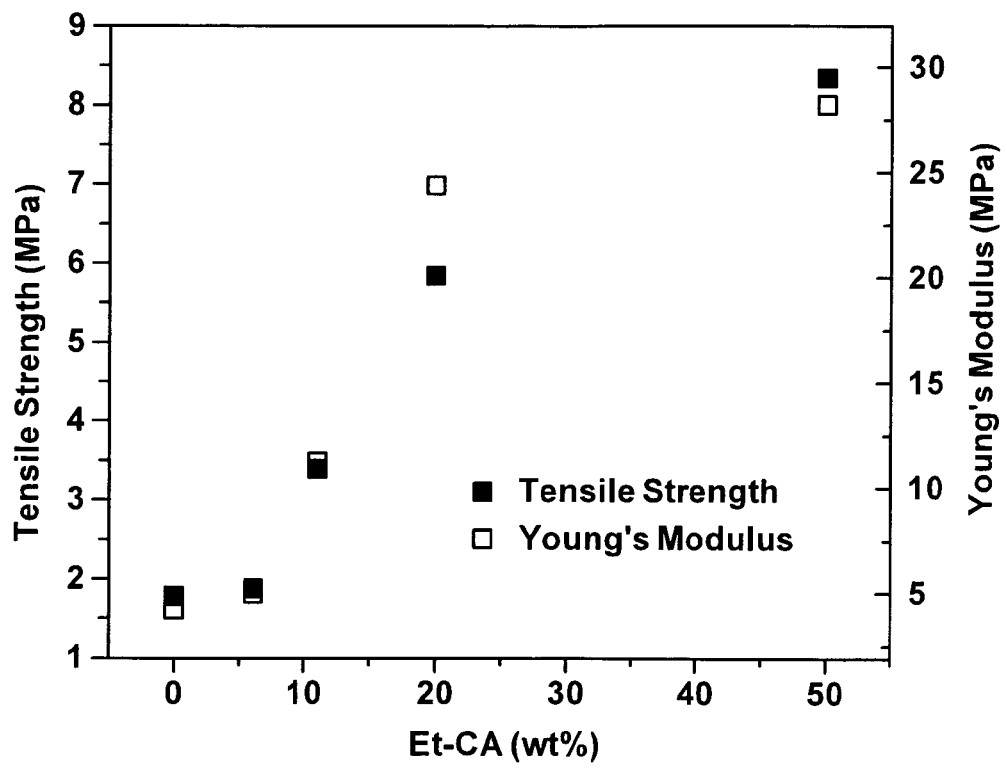
FIG. 12 is a graph illustrating the tensile strengths and moduli of co-networks as the function of Et-CA concentration from Table 4.

FIG. 12 shows both the tensile strengths and moduli increase as function of the concentration of Et-CA used for co-network. This indicates that the co-network with Et-CA improves the network formation and crosslink density. Ø(PIB-CA)$_3$ homo-network shows 1.6 MPa ultimate tensile strength, and 4.9 MPa Young's modulus, while Ø(PIB-CA)$_3$/Et-CA50 co-network shows 8 MPa ultimate tensile strength, and 29.5 Young's modulus. The tensile strength and Young's modulus of the co-networks are almost saturated at Ø(PIB-CA)$_3$/Et-CA50 co-network.

TABLE 4

Mechanical Properties and $T_g$'s

| Networks | EtCA Added Wt % | Mole | Tensile (MPa) | Elongation (%) | Young's Modulus (MPa) | $T_g$ (° C.)*** low/high |
|---|---|---|---|---|---|---|
| Ø(PIB-CA)$_3$ | 0 | 0 | 1.6 | 70 | 4.9 | −12/76° C. |
| Ø(PIB-CA)$_3$/EtCA6 | 6 | 0.47 | 1.8 | 52 | 5.3 | |
| Ø(PIB-CA)$_3$/EtCA11 | 11 | 0.91 | 3.5 | 48 | 11.0 | |
| Ø(PIB-CA)$_3$/EtCA20 | 20 | 1.65 | 7 | 50 | 20.2 | −12/127° C. |
| Ø(PIB-CA)$_3$/EtCA50 | 50 | 4.53 | 8 | 11 | 29.5 | |

***$T_g$'s from tan δ traces.

The last digit in the network codes of column 1 above indicates the weight percent of EtCA used therein. The molecular weights of the Ø(PIB-CA)$_3$ is 2,800 g/mol. The Mol column above is relative to the CA in Ø(PIB-CA)$_3$.

FIG. 11 is a graph illustrating the stress-strain traces of Ø(PIB-CA)$_3$ and Ø(PIB-CA)$_3$/EtCA co-networks of Table 4. Co-networks formed with Ø(PIB-CA)$_3$ plus EtCA exhibit significantly enhanced mechanical properties relative to a control network prepared in the absence of EtCA. Specifically, as shown by the plot in FIG. 12, the tensile strengths and moduli of the co-networks increase linearly with the amount of EtCA. Interestingly, in spite of the different EtCA concentrations, the elongations of the co-networks remain constant at approximately 48% in the range investigated.

Figure 13:
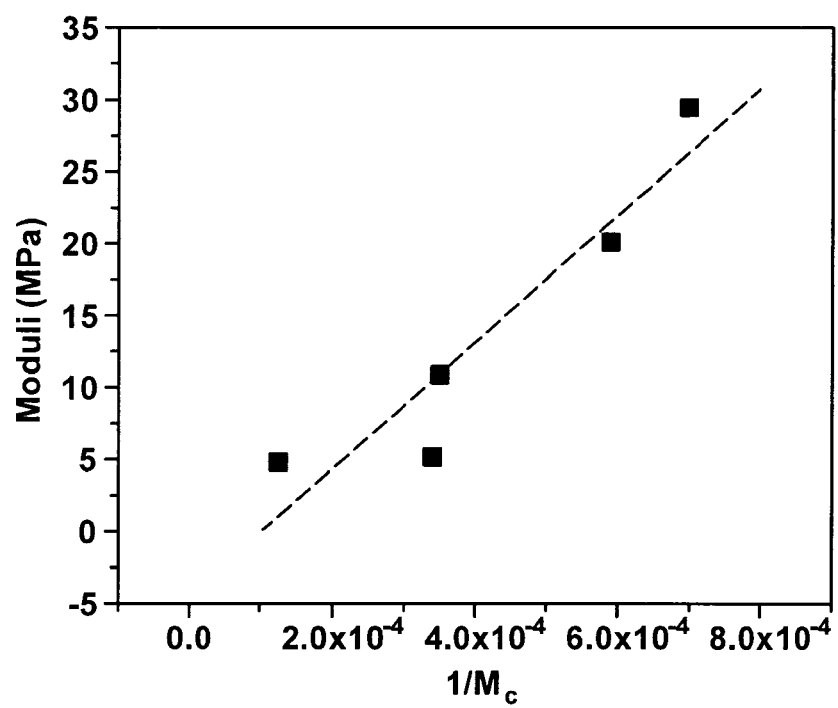
FIG. 13 is a graph illustrating moduli as the function of 1/$M_c$.

FIG. 13 shows the moduli of one Ø(PIB-CA)$_3$ and three Ø(PIB-CA)$_3$/Et-CA co-networks as a function of $1/M_c$. The moduli increase with increasing of crosslink density ($1/M_c$)

Figure 14:
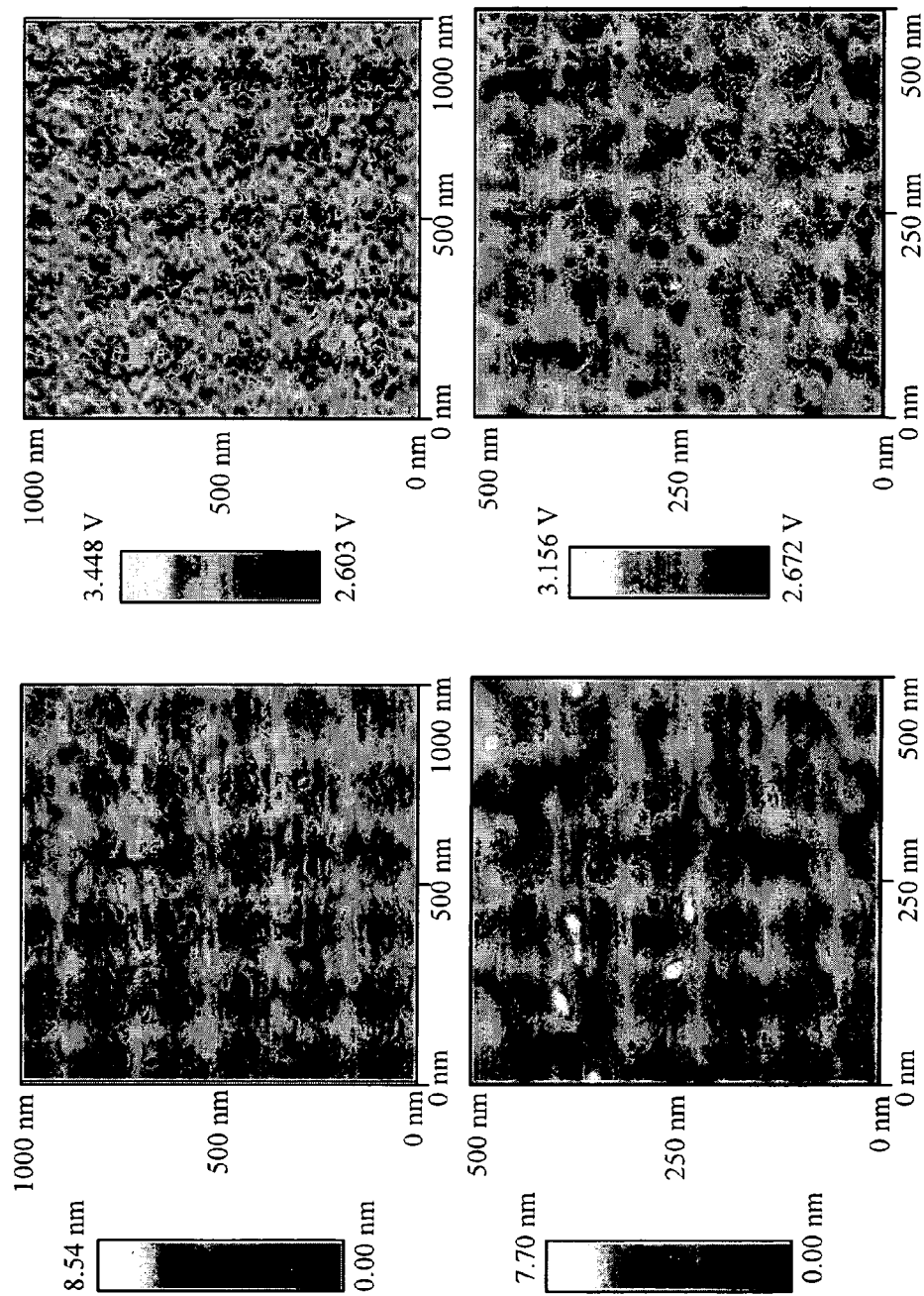
FIG. 14 is a set of AFM images of a Ø(PIB-CA)$_3$/Et-CA50 co-network (left: height image; right: phase image) with the bottom set of images being a close-up of the top set of images.

Results and Discussion—AFM Characterization of Ø(PIB-CA)$_3$/Et-CA Co-Networks:

The surface morphology of Ø(PIB-CA)$_3$/Et-CA co-networks is studied by AFM. FIG. 14 shows the images obtained with the Ø(PIB-CA)$_3$/Et-CA50 co-network at different magnifications. The co-network exhibits segregated two phases of soft PIB and glassy poly(Et-CA) with domain sizes of PIB (light domain) in the 30 to 40 nm range and heights of 2 to 3 nm. The dark poly(Et-CA) domain appear as low phase, valleys, co-continuous phase in the lighter continuous PIB phase, similarly to that reported for styrene-b-butadiene-b-styrene and styrene-b-isoprene-b-styrene, and styrene-b-isobutylene-b-styrene. It is argued that the hills and valleys observed in block copolymers may be artifacts, however TEM studies of the same sample showed a similar co-continuous morphology.

According to this evidence, there is phase separation between the hard poly(Et-CA) and the soft PIB domains. The hard domains desirably reinforce and/or stiffen the rubbery network.

Results and Discussion—DMTA of Networks and Co-Networks:

FIG. 5 shows DMTA traces of a representative Ø(PIB-CA)$_3$ network and the Ø(PIB-CA)$_3$/Et-CA20 co-network. At lower temperatures (below −75° C.), there is little difference between the storage moduli of the Ø(PIB-CA)$_3$ network and the Ø(PIB-CA)$_3$/Et-CA20 co-network, due to higher resistance to deformation of the co-network. By increasing the temperature from −100 to 0° C., the materials soften and the moduli decrease dramatically. The Ø(PIB-CA)$_3$/Et-CA20 co-network, due to its higher crosslink density, exhibits slower relaxation in the glassy transition zone (−75° C. to 0° C.) than the Ø(PIB-CA)$_3$ network. The loss factor of the co-network is lower than that of the network at −25° C. because of the interaction between the PIB and poly(Et-CA) phases. The plateau modulus starts at approximately 0° C. and extends up to approximately 50° C., where the mechanical relaxation of the poly(Et-CA) phase starts.

The prominent loss factor peaks at approximately 76° C. and approximately 127° C. are most likely due to the $T_g$'s of the hard polyCA phases in the Ø(PIB-CA)$_3$ network and Ø(PIB-CA)$_3$/Et-CA20 co-network, respectively. The glass transition temperature of poly(Et-CA) is reported to be 140° C. The difference in the $T_g$'s is possibly due to the lower molecular weights of the CA domains in the networks. The size of the CA domains is expected to increase by the use of higher concentrations of Et-CA.

Figure 15:
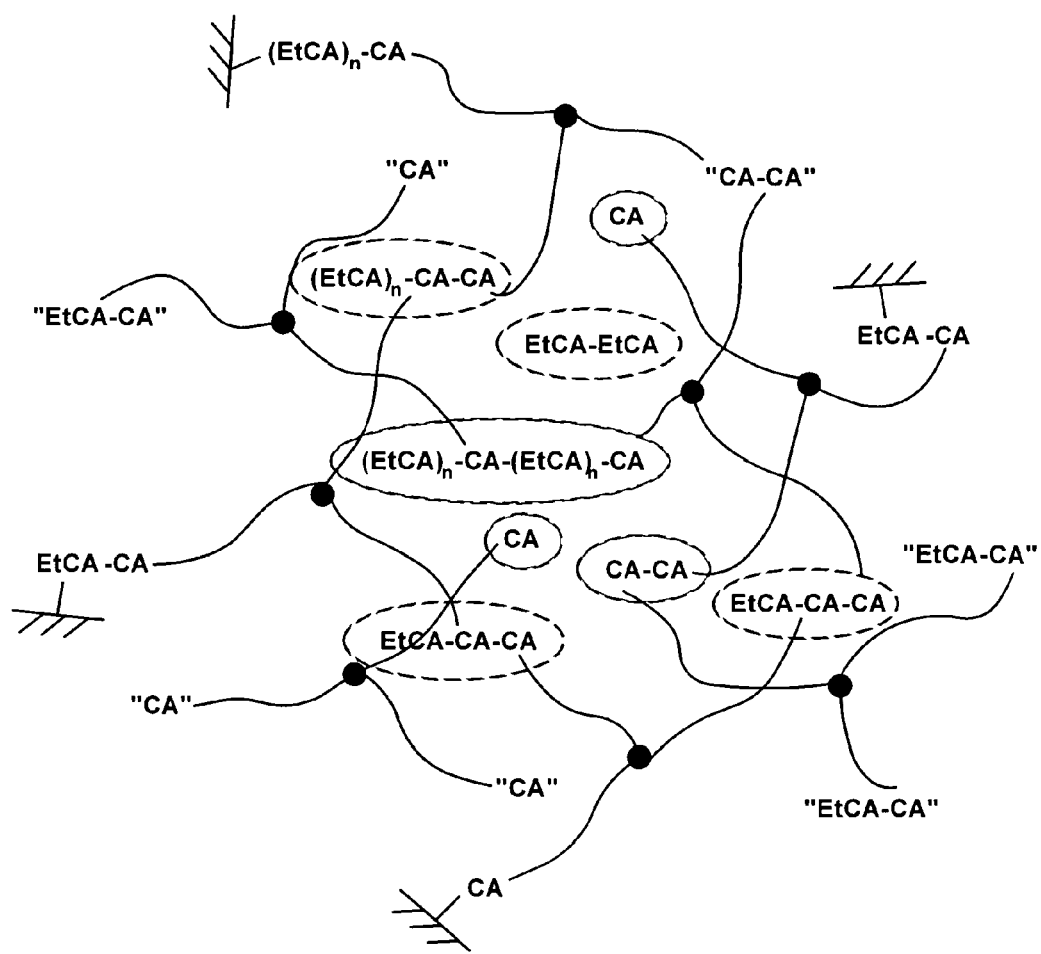
FIG. 15 is an illustration of another idealized structure of a co-network formed of Ø(PIB-CA)$_3$ and Et-CA upon reaction with nucleophiles.

Results and Discussion—Mechanical Structure:

On the basis of the chemistry and the above physical property data, one is able to propose a model for the molecular structure of Ø(PIB-CA)$_3$/Et-CA co-networks. FIG. 15 helps to visualize the microstructure of co-networks that may form upon contacting a mixture of Ø(PIB-CA)$_3$ and Et-CA with proteinaceous tissue. This model reflects the copolymerization expected to occur between the CA groups, and is in line with swelling and DMTA results. Overall, this model accounts for the fact that the strength (and modulus) of co-networks can be increased by increasing the $M_{c,PIB}$ without increasing the molecular weight of the Ø(PIB-CA)$_3$. Copolymerization of Ø(PIB-CA)$_3$ with the small Et-CA increases the molar concentration of CA groups in the charge, and thus reduces the number of useless/buried/dangling PIB chains, and increases the number of covalently linked PIB segments. By incorporating the dangling PIB chains into the co-networks, the $M_{e,PIB}$ of the PIB increases above approximately 7300 g/mol and thus the load-bearing capacity of the co-network increases.

In FIG. 15, "CA" and "EtCA-CA" indicate unattached and/or "useless" groups (e.g., HOCH$_2$CH(CN)COO-PIB); circles and ovals indicate buried CA or EtCA-CA groups; and the

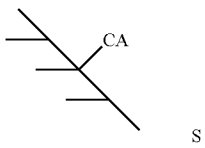

indicate CA or EtCA-CA groups attached to surfaces.

Moreover, the copolymerization of Ø(PIB-CA)$_3$ with large amounts of Et-CA yields glassy poly(Et-CA) domains (T$_g$ equal to 140° C.) covalently attached to and randomly-dispersed in the PIB matrix; these hard domains would desirably reinforce/stiffen the rubbery network. The size and concentration of the reinforcing poly(Et-CA) domains can be controlled by the amount of Et-CA in the copolymerization.

Conclusions:

In one embodiment, the present invention relates to an efficient new strategy for the synthesis of CA-telechelic PIBs in general, and for Ø(PIB-CA)$_3$ in particular. The products, and the intermediates of the synthesis process, are characterized by $^1$H NMR spectroscopy. Ø(PIB-CA)$_3$ of $M_n$ approximately 3,000 g/mol is a free-flowing viscous liquid syringible with slight manual pressure through a 18 gauge hypodermic needle. When Ø(PIB-CA)$_3$ is contacted with proteins (e.g., fresh egg), a bolus of rubber covalently linked to the initiating proteinaceous tissue is produced.

In another embodiment, the copolymerization of Ø(PIB-CA)$_3$ with Et-CA initiated by nucleophiles (i.e., DMT, and proteinaceous tissue) yields co-networks, consisting of glassy poly(Et-CA) domains crosslinked by 3-arm star rubbery PIB domains. The composition, and therefore the properties, of the co-networks can be varied by controlling the relative amounts of the starting materials. The swelling behavior of co-network suggests co-continuity of poly(Et-CA) and PIB domains. AFM also indicates phase segregation between the two phases. The oxidative resistance of the Ø(PIB-CA)$_3$/Et-CA co-network to concentrated nitric acid is demonstrated by tensile test and FTIR spectroscopy. On the basis of the chemistry and the physical property data obtained with swelling, AFM, and tensile-elongation study, we proposed a model for the molecular structure of Ø(PIB-CA)$_3$/Et-CA co-networks.

Additional Embodiments

Section I

In this section the following items are addressed and/or discussed:

(1) A new cyanoacrylate monomer, 1-cyanoacryl-2,4,4-trimethylpentane (TMP-CA), which contains the di-isobutylene unit is synthesized;

(2) Contact of N,N-dimethyl-p-toluidine (DMT) with Ø(PIB-CA)$_3$+TMP-CA mixtures instantaneously produces soft rubbery copolymers. The rubbers swell but do not dissolve in THF, which indicates co-network formation;

(3) The swelling behavior of Ø(PIB-CA)$_3$/TMP-CA rubbers also indicates the existence of co-networks;

(4) Ø(PIB-CA)$_3$/TMP-CA rubbers with different mole % of TMP-CA are synthesized and their mechanical properties are investigated;

(5) The polymerizability of Ø(PIB-CA)$_3$ initiated with PIBs fitted with terminal —NH$_2$, —NHR (R equals butyl, propyl), and —OH groups is demonstrated. Three rubbers are new patentable compositions;

(6) Meticulously dry Ø(PIB-CA)$_3$ is stable for long periods of time; and (7) Two methods have been developed for the rapid production of in situ crosslinked PIB rubbers: (a) copolymerization of Ø(PIB-CA)$_3$ with TMP-CA, and (b) polymerization of Ø(PIB-CA)$_3$ with the macroinitiator Ø(PIB-NH$_2$)$_3$. Both methods are being evaluated for in vivo delivery by double-barreled syringe.

Synthesis of TMP-CA

By copolymerizing cyanoacrylate-telechelic 3-arm star polyisobutylene (Ø(PIB-CA)$_3$) with Et-CA a new molecule is produced: trimethylpentane cyanoacrylate (TMP-CA) in which the CA group is attached to isobutylene dimer. This molecule yields superior performance versus Et-CA because: (1) TMP-CA is highly compatible with Ø(PIB-CA)$_3$; (2) TMP-CA readily copolymerizes with Ø(PIB-CA)$_3$; and (3) Ø(PIB-CA)$_3$/TMP-CA copolymers are more biocompatible/biostable than copolymers with other small CAs.

Reaction Scheme 3 illustrates the steps, in one instance, that can be used for the synthesis of TMP-CA: (1) 2,2,4-trimethylpent-1-ene (TMP) is converted to 2,2,4-trimethylpent-1-ol (TMP-OH) by hydroboration/oxidation, (2) the TMP-OH is esterified with (pre-made) anthracene-protected cyanoacrylic acid (pCA) to protected 2,2,4-trimethylpent-1-cyanoacrylate (pTMP-CA), and (3) finally the pTMP-CA is de-protected with excess maleic anhydride to produce TMP-CA. TMP-CA is a clear high boiling liquid.

Reaction Scheme 3: Synthetic Strategy for the preparation TMP-CA

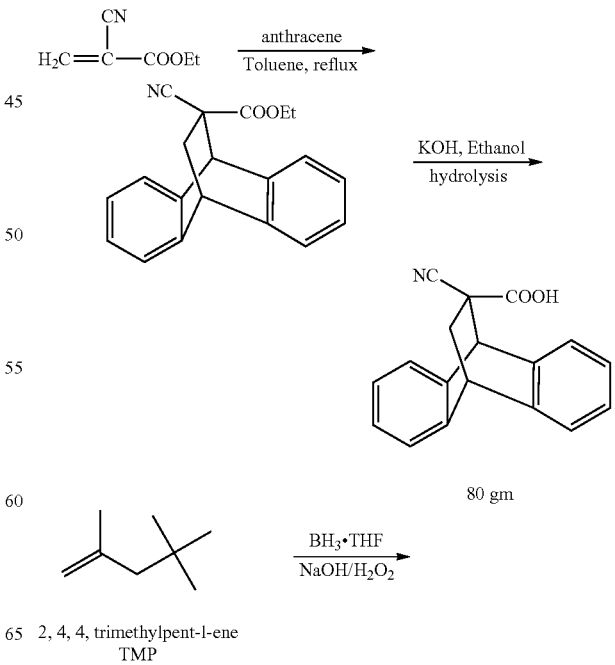

2, 4, 4, trimethylpent-l-ene
TMP

-continued

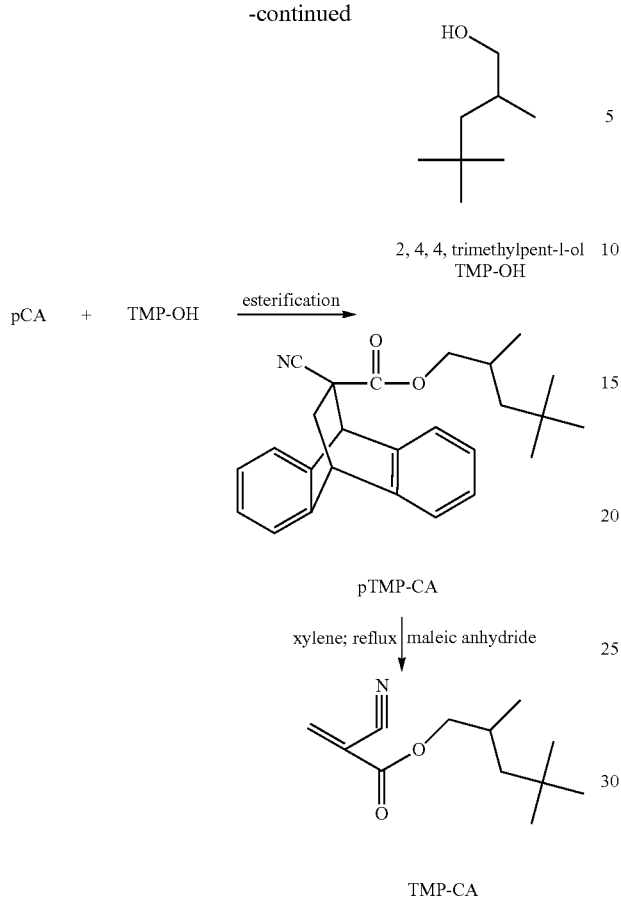

2,4,4,trimethylpent-l-ol TMP-OH pCA + TMP-OH →(esterification) pTMP-CA xylene; reflux | maleic anhydride

TMP-CA

Figure 16:
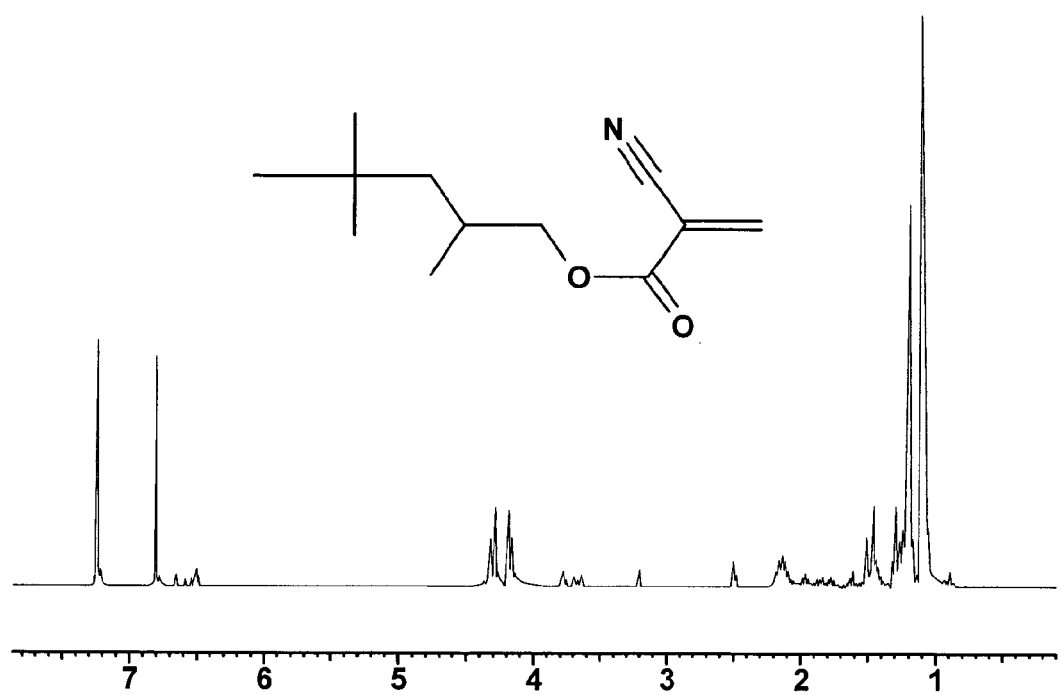
FIG. 16 is a $^1$H NMR spectrum of TMP-CA.

FIG. 16 shows the NMR spectrum of TMP-CA. According to this evidence the product is 99% pure.

Synthesis of Ø(PIB-CA)$_3$/TMP-CA Co-Networks

The copolymerization of Ø(PIB-CA)$_3$/TMP-CA charges is carried out by adding 2 drops (approximately 0.03 mL) of DMT to mixtures of Ø(PIB-CA)$_3$ and TMP-CA in toluene. All the co-polymerizations ensue, in one embodiment, essentially instantaneously upon DMT addition.

The rate of homopolymerization of Ø(PIB-CA)$_3$ is rather low because of the relatively low molar concentration of CA groups in the polymeric ($M_n$ is approximately 3,000 g/mol) starting material. Assuming that the reactivity ratios of Ø(PIB-CA)$_3$ and TMP-CA are identical, and that the rate of copolymerization follows second order kinetics, i.e.; $R_{cop}=k_{cop}\{[Ø(PIB-CA)_3]+[TMP-CA]\}[DMT]$, increasing the [TMP-CA] will increase the $R_{cop}$. Thus, the rate of copolymerization will be controllable by controlling the relative molar concentrations of starting materials and the initiator.

Experiments are carried out in which Ø(PIB-CA)$_3$+TMP-CA is contacted with living tissue (e.g., fresh chicken egg) to obtain co-networks and the mechanical properties of the products obtained are studied.

Extractables and Swelling Behavior:

Preliminary extractables and swelling results are summarized in Table 5. The swelling of Ø(PIB-CA)$_3$/TMP-CA co-networks of different compositions is studied by the use of hexanes, THF, and acetone solvents. The hexanes extractables are low (less than about 10%), which indicates satisfactory crosslinking. Swelling in hexanes (a good solvent for PIB and poor solvent for poly(TMP-CA)) decreases with increasing TMP-CA in the charge. In contrast, swelling in acetone (a non-solvent for PIB but good solvent for poly(TMP-CA)) increases with increasing TMP-CA in the charge. These trends indicate the existence of co-continuous co-networks. Swelling in THF (a good solvent for both PIB and poly(TMP-CA)) increases with increasing TMP-CA in the charge, which indicates decreasing crosslink density of the co-networks.

TABLE 5

Summary of Extractables and Swelling of a Ø(PIB-CA)$_3$ Homo-Network and Three Ø(PIB-CA)$_3$/TMP-CA Co-Networks

| Network* | TMP-CA Wt % | TMP-CA Mole % | Extractables** (%) | Swelling (%) Hexane | Swelling (%) THF | Swelling (%) Acetone |
|---|---|---|---|---|---|---|
| Ø(PIB-CA)$_3$ | 0 | 0 | 9 | 79 | 126 | 8 |
| Ø(PIB-CA)$_3$/TMP-CA5 | 7 | 33 | 6 | 77 | 134 | 12 |
| Ø(PIB-CA)$_3$/TMP-CA10 | 12 | 47 | 7 | 72 | 153 | 18 |
| Ø(PIB-CA)$_3$/TMP30 | 30 | 74 | 3 | 71 | 196 | 35 |

*The $M_n$ of Ø(PIB-CA)$_3$ is 2,800 g/mol
**in hexanes.

Mechanical Properties:

Stress strain properties of micro-dumbbell shaped samples are determined by the use of an Instron 5543 tester with 1 kN force and a crosshead speed of 5 mm/min, following the ISO 527 S2 method. The samples are 0.2 to 0.3 mm thick films prepared in Teflon molds.

Table 6 summarizes stress strain data of a Ø(PIB-CA)$_3$ homo-network and three Ø(PIB-CA)$_3$/TMP-CA co-networks. All the products are soft rubbery solids.

The relatively low stresses are most likely due to the relatively low molecular weight copolymer produced by the relatively large molar amount of initiator (0.03 mL equal to $2.08 \times 10^{-4}$ mol DMT) used i.e., assuming $PD_n=\{[Ø(PIB-CA)_3]+[TMP-CA]\}/[DMT]=(2.33\times10^{-4}+14.4\times10^{-4})/2\times10^{-4}$=approximately 9.

TABLE 6

Mechanical Properties of a Ø(PIB-CA)$_3$ Homo-Network and Three Ø(PIB-CA)$_3$/TMP-CA Co-Networks

| Network | TMP-CA Wt % | TMP-CA Mole % | Stress MPa | Strain % |
|---|---|---|---|---|
| Ø(PIB-CA)$_3$ | 0 | 0 | 0.55 | 48 |
| Ø(PIB-CA)$_3$/TMPCA5 | 5 | 33 | 0.8 | 45 |
| Ø(PIB-CA)$_3$/TMP-CA12 | 12 | 47 | 1.2 | 98 |
| Ø(PIB-CA)$_3$/TMP30 | 30 | 74 | 2.3 | 195 |

Synthesis of Ø(PIB-CA)$_3$ Networks by the use of Ø(PIB-NH$_2$)$_3$ and Similar PIB-Based Nucleophiles Molecular contact between Ø(PIB-CA)$_3$ and the small highly polar initiator DMT may be difficult because of the incompatibility between Ø(PIB-CA)$_3$ and DMT. We theorized that compatibility between Ø(PIB-CA)$_3$ and the initiating moiety could be increased, and initiation facilitated, by the use of a PIB of $M_n$ of approximately 3,000 g/mole fitted with a terminal strong nucleophile, e.g., Ø(PIB-NH$_2$)$_3$.

Thus, the preparation Ø(PIB-NH$_2$)$_3$ of $M_n$ of approximately 3,000 g/mole (of this new compound see more later), subsequent manual blending of it in bulk (no solvent) with an equal weight (approximately 1 gram) of Ø(PIB-CA)$_3$ of $M_n$ of approximately 3,000 g/mole. As soon as the two viscous liquids come into contact with one another in a Teflon mold, a soft slightly yellow rubbery solid forms. The rubber exhibited the consistency of a high MW PIB swelled but did not dissolve in THF.

Reaction Scheme 4 helps to visualize the reaction between Ø(PIB-CA)$_3$ and Ø(PIB-NH$_2$)$_3$.

Reaction Scheme 4: Co-Network Formation of Between Ø(PIB-CA)$_3$ and Ø(PIB-NH$_2$)$_3$

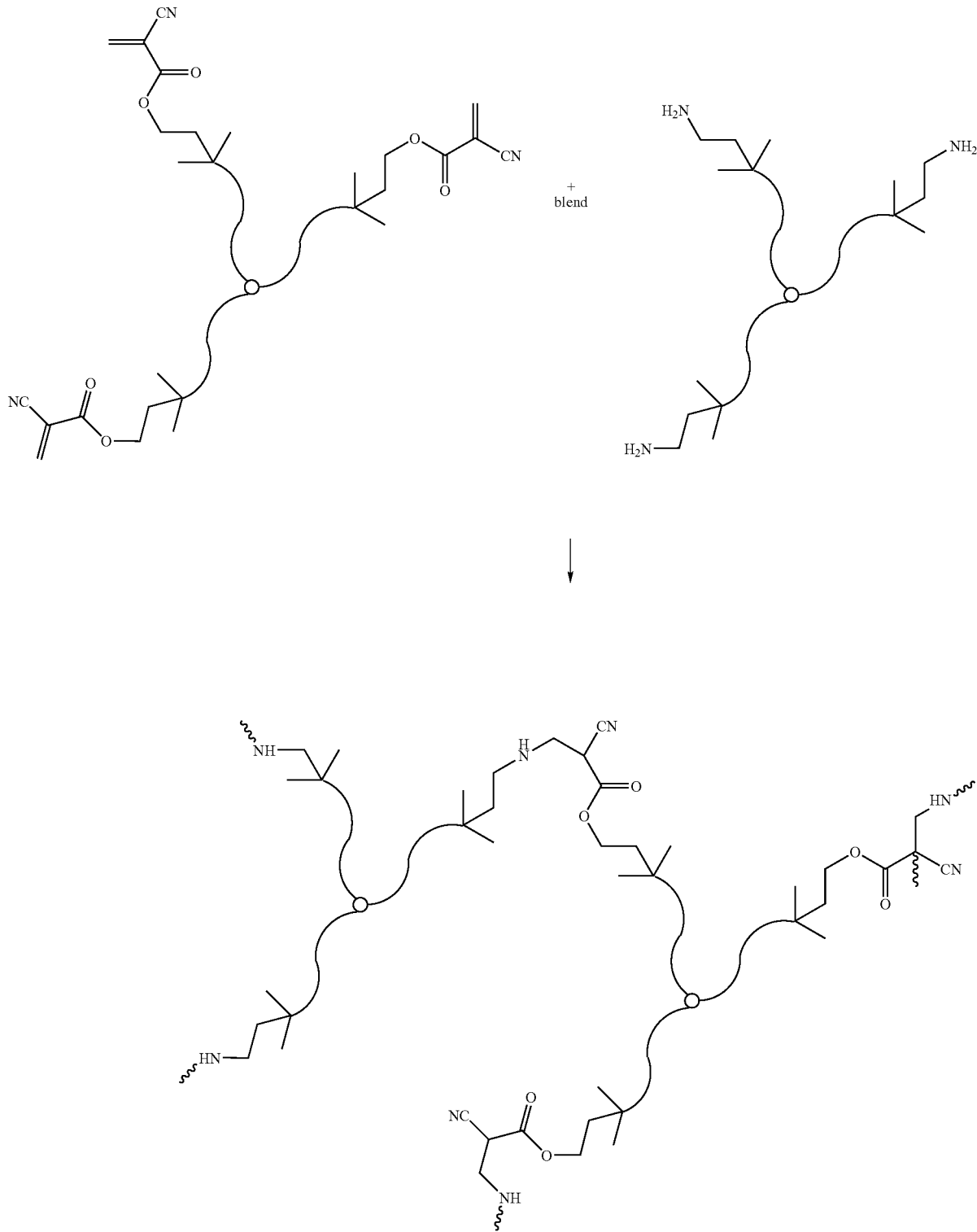

Encouraged by the above results we blended Ø(PIB-CA)₃ with similar other PIB-based nucleophiles, i.e., HO-PIB-OH, O(PIB-NH—CH₂—CH(OH)—CH₂—OH)₃, and obtained soft solid rubbers.

Figure 17:
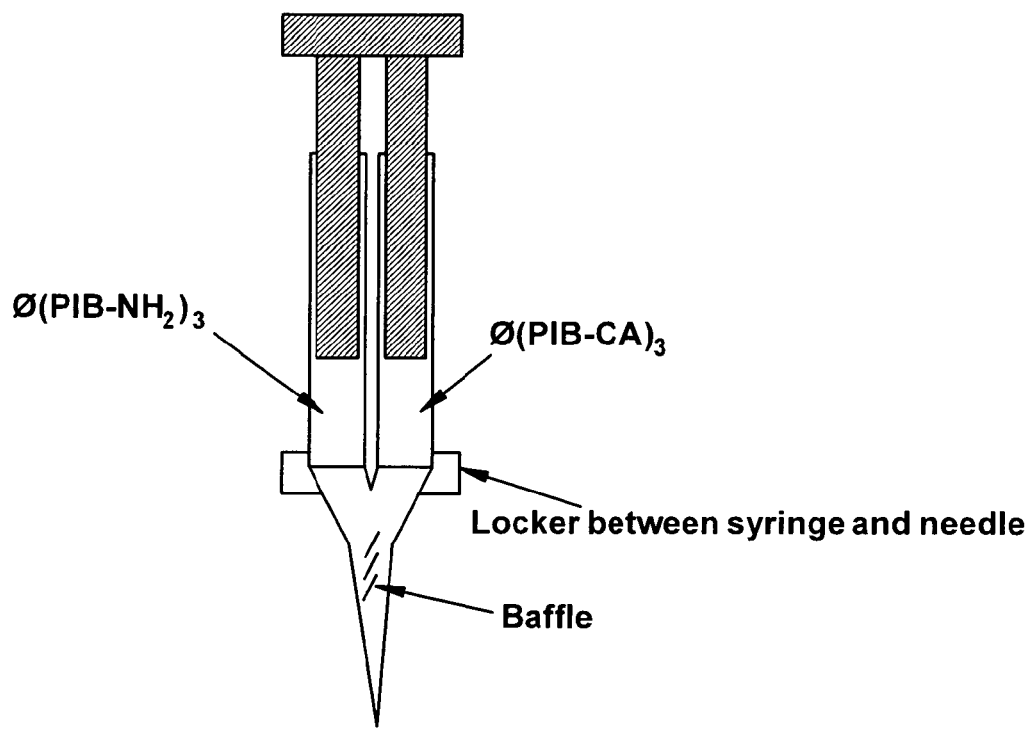
FIG. 17 is an illustration of a dual syringe filled with Ø(PIB-CA)$_3$ and Ø(PIB-NH$_2$)$_3$ for the in situ production of crosslinked PIB rubber.

Preliminary experiments are carried out to study the bulk polymerization of Ø(PIB-CA)₃ initiated by the macroinitiator, Ø(PIB-NH₂)₃ in a double barrel syringe. Thus one barrel of the syringe is filled with approximately 1 grams of Ø(PIB-CA)₃ and the other with approximately 1 grams of Ø(PIB-NH₂)₃. When the two ingredients are pushed into the blending tip, they reacted and produced a soft extrudable rubber. The product swells but does not dissolve in THF indicating the formation of crosslinked PIB. FIG. 17 is an illustration of the experimental setup. Further experiments will be carried out with Ø(PIB-CA)₃ and other PIB-based macroinitiators parameters (i.e., length of blending tip, transit time in tip, concentrations etc.) to obtain in situ PIB rubbers of desirable mechanical properties.

The Significance and Synthesis of Ø(PIB-NH₂)₃:

Amine-terminated PIBs, particularly NH₂-telechelic-PIBs, are of great scientific and practical interest, and continuous efforts are made for their synthesis. While, the syntheses of several such products have been described, the known procedures for producing such compounds are economically unattractive. As mentioned above, it is postulated that Ø(PIB-NH₂)₃ would be an efficient initiator for the polymerization of Ø(PIB-CA)₃. Therefore, a effective synthesis route for such a molecule, and the molecule itself, would be highly desirable.

Reaction Scheme 5 summarizes the steps that are undertaken for the synthesis of Ø(PIB-NH₂)₃.

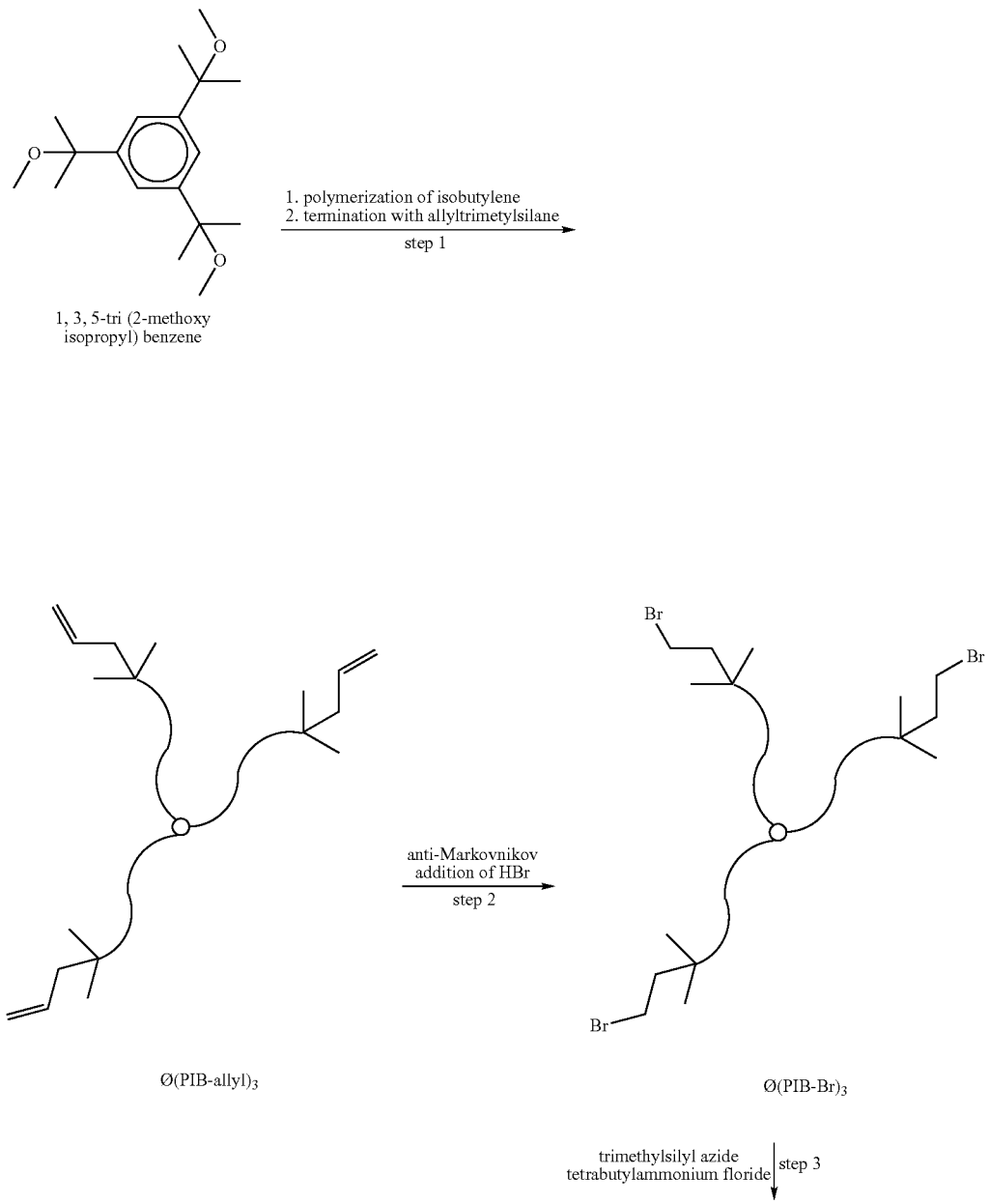

Reaction Scheme 5: The Synthesis of Ø(PIB-NH₂)₃

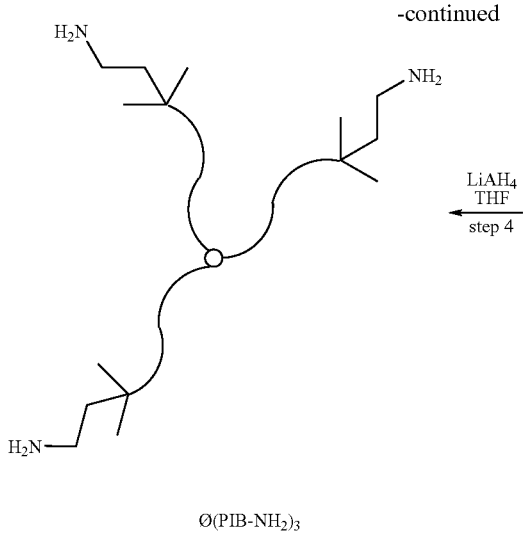

Ø(PIB-NH$_2$)$_3$

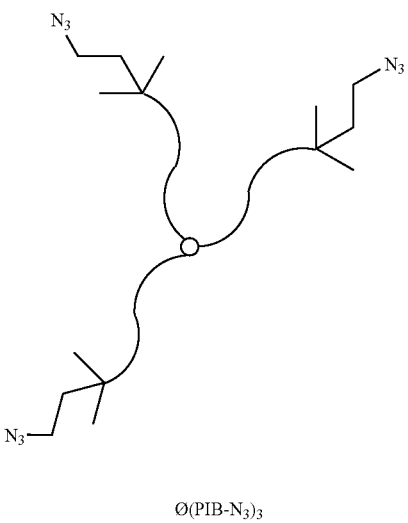

Ø(PIB-N$_3$)$_3$

Starting with Ø(PIB-Br)$_3$ one prepares three-arm star azido functionalized PIB [Ø(PIB-N$_3$)$_3$] as shown above. A 500 mL 3-neck round bottom flask equipped with a stirrer and a condenser, is charged with Ø(PIB-Br)$_3$ (10 grams, 3,000 g/mol, 0.0033 moles), trimethylsilyl azide (5 grams, 0.043 moles), and tetrabutylammonium fluoride (10 grams, 0.038 moles) in 100 mL of THF. The solution is stirred at 50° C. for 2 hours, and the solvent and excess trimethylsilyl azide are removed under reduced pressure (rotavap). The polymer is dissolved in hexanes, washed with water 3 times, dried with MgSO$_4$, filtered, and the solvent is evaporated by a rotavap at 50° C. The product Ø(PIB-N$_3$)$_3$ is a clear, colorless, transparent, viscous liquid. The reaction is essentially quantitative. The total yield is 9 grams (90% of theory).

Figure 18:
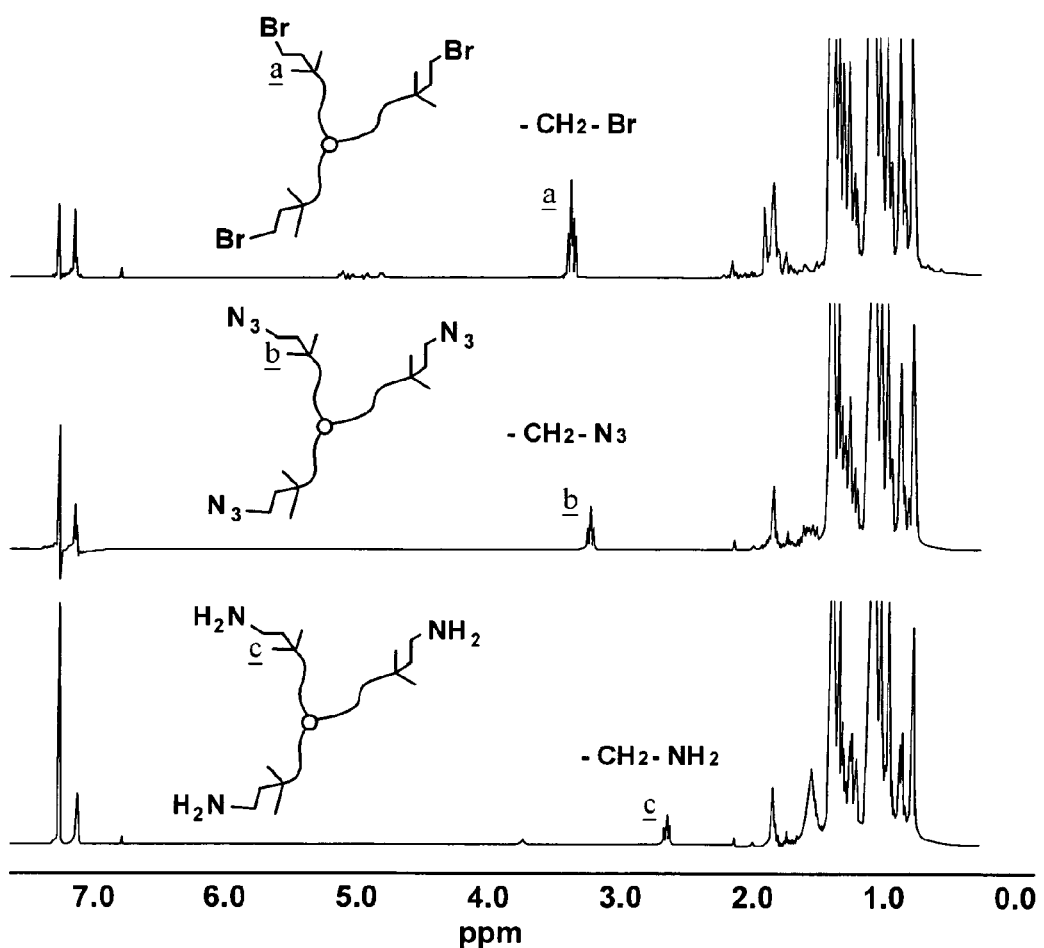
FIG. 18 is a $^1$H NMR Spectra of Ø(PIB-Br)$_3$, Ø(PIB-N$_3$)$_3$, and Ø(PIB-NH$_2$)$_3$.

Subsequently, the Ø(PIB-N$_3$)$_3$ is reduced by LiAlH$_4$ in dry THF. Thus, a 500 mL 3-neck round bottom flask equipped with a stirrer and dropping funnel is charged with Ø(PIB-N$_3$)$_3$ (7 grams, 0.035 moles) in 100 mL of THF, and excess LiAlH$_4$ (5 grams, 0.13 moles) in 50 ml of THF is added dropwise. After 1 hour, the solvent is removed, the product is dissolved in hexanes, washed with water 3 times, dried with MgSO$_4$, filtered, and the solvent is evaporated by a rotavap at 50° C. The product Ø(PIB-NH$_2$)$_3$ is a clear, colorless, transparent, viscous liquid. The reaction is essentially quantitative. The total yield is 6 grams (86% of theory). FIG. 18 shows the $^1$H NMR spectra of Ø(PIB-Br)$_3$, Ø(PIB-N$_3$)$_3$, and Ø(PIB-NH$_2$)$_3$, together with assignments.

Additional Embodiments

Section II

In this section the following items are addressed and/or discussed:

(1) Co-injection of Ø(PIB-CA)$_3$ "monomer" and Ø(PIB-NEt$_2$)$_3$ macroinitiator by dual-syringes produces soft crosslinked rubbery extrudates by in situ bulk polymerization, and yields polymers with promising mechanical properties;

(2) Similarly, the co-injection of Ø(PIB-CA)$_3$/TMP-CA mixtures and Ø(PIB-NEt$_2$)$_3$ macroinitiator yields crosslinked rubbers. The properties of these new rubbers are, in one instance, controlled by the stoichiometry of the ingredients;

(3) The stress/strain properties of these novel rubbers are investigated in separate experiments; the sheets needed for Instron testing are prepared by casting; and (4) Ø(PIB-CA)$_3$/TMP-CA co-networks containing various quantities of TMP-CA are prepared with the small molecule initiator N,N-dimethyl-p-toluidine (DMT), and the stress/strain properties of the crosslinked rubbers are determined. The tensile strength and elongation of the network made with Ø(PIB-CA)$_3$ and DMT are 1.1 MPa and 56%, respectively. Co-networks obtained with various amounts (up to 42 weight percent) of TMP-CA are made, and their properties are determined. For example, a Ø(PIB-CA)$_3$/TMP-CA co-network containing 42 weight percent TMP-CA exhibited 3.7 MPa tensile stress and 207% elongation.

The Ø(PIB-NEt$_2$)$_3$ Macroinitiator: Rationale for the use of the Ø(PIB-NEt$_2$)$_3$ Macroinitiator:

The polymerization of Ø(PIB-CA)$_3$ of M$_n$ equal to 3,000 g/mol by moisture and proteinacious tissue (simulated by fresh egg white) is relatively slow (hours, days) for the envisioned clinical applications. While not wishing to be bound to any one theory, it is speculated that the low rate of polymerization is most likely due to the low rate of initiation by water, a relatively weak nucleophile. Indeed, in one embodiment, the strong nucleophile N,N-dimethyl-p-toluidine (DMT) instantaneously initiated the polymerization of Ø(PIB-CA)$_3$ and the copolymerization of Ø(PIB-CA)$_3$/TMP-CA mixtures at room temperature. In line with this, in one embodiment the chain ends of a three arm-star PIB are each "fitted" with a tertiary amine group (-NEt$_2$). This new compound, Ø(PIB-NEt$_2$)$_3$, is then used to initiate the polymerization of Ø(PIB-CA)$_3$, and Ø(PIB-CA)$_3$/TMP-CA mixtures. In one instance, it is noted that the Ø(PIB-NEt$_2$)$_3$ macroinitiator essentially instantaneously polymerizes Ø(PIB-CA)$_3$ and copolymerizes Ø(PIB-CA)$_3$/TMP-CA mixtures to rubbers. Evidently the Ø(PIB-NEt$_2$)$_3$ is a highly reactive new macroinitiator, and desirably, the tertiary amine group cannot cause termination of the polymerization reaction because of the absence of protons on the nitrogen.

The chemical equations in Reaction Schemes 6 and 7 below illustrate the initiation step, and the overall structure of the polymer formed from Ø(PIB-CA)$_3$ plus Ø(PIB-NEt$_2$)$_3$:

Reaction Scheme 6: Initiation and Propagation of Ø(PIB-CA)$_3$ with Ø(PIB-NEt$_2$)$_3$
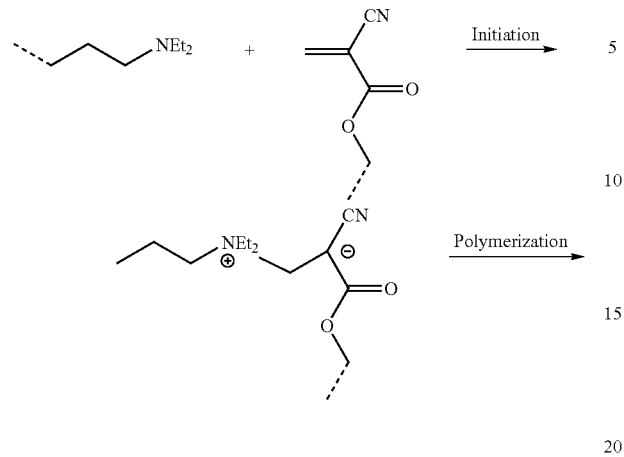

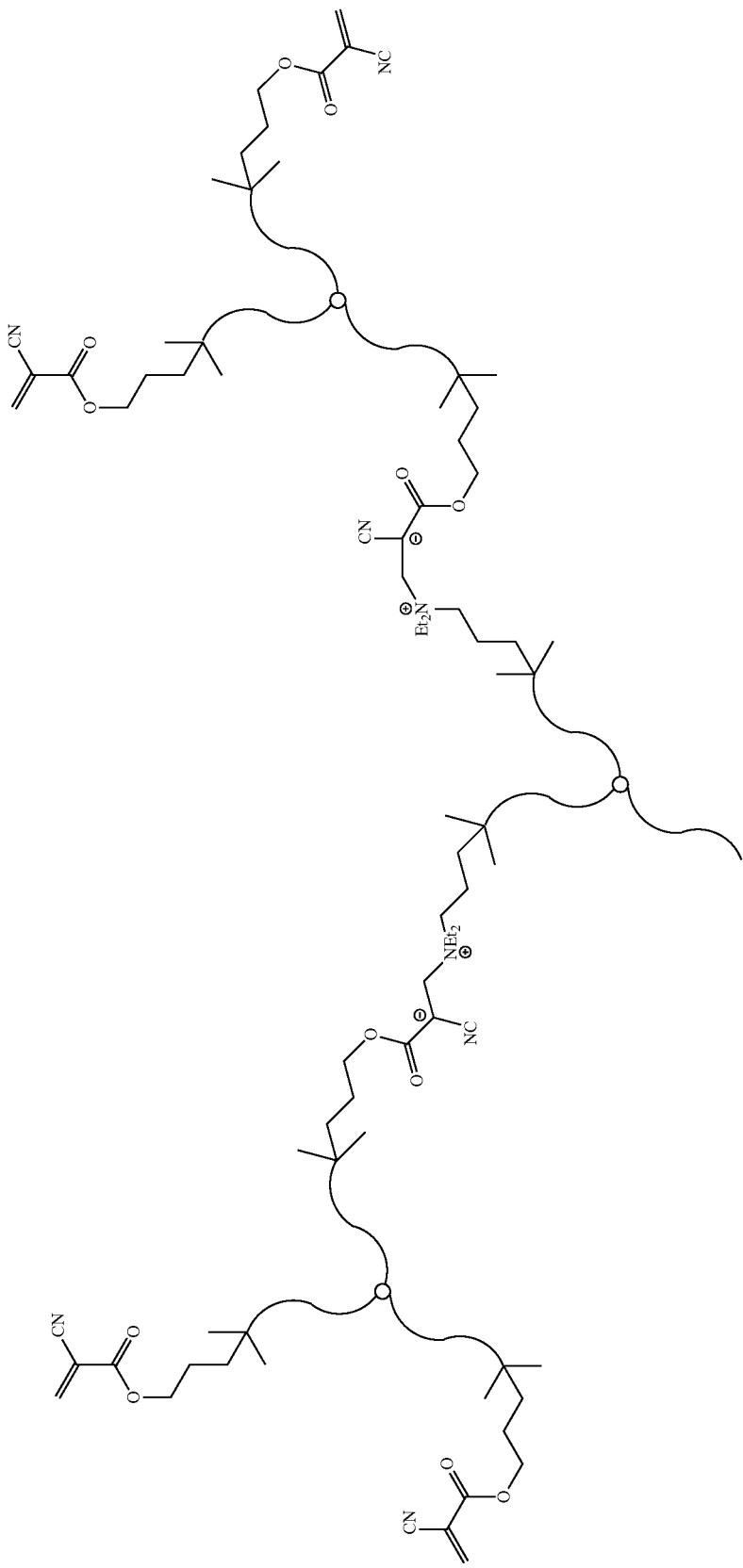
Reaction Scheme 7: Idealized structure of the crosslinked PIB formed from Ø(PIB-CA)₃ plus Ø(PIB-NEt₂)₃. The -CA and -NEt₂ groups sustain additional reactions. The dotted circle indicates polymerization of -CA groups.

-continued
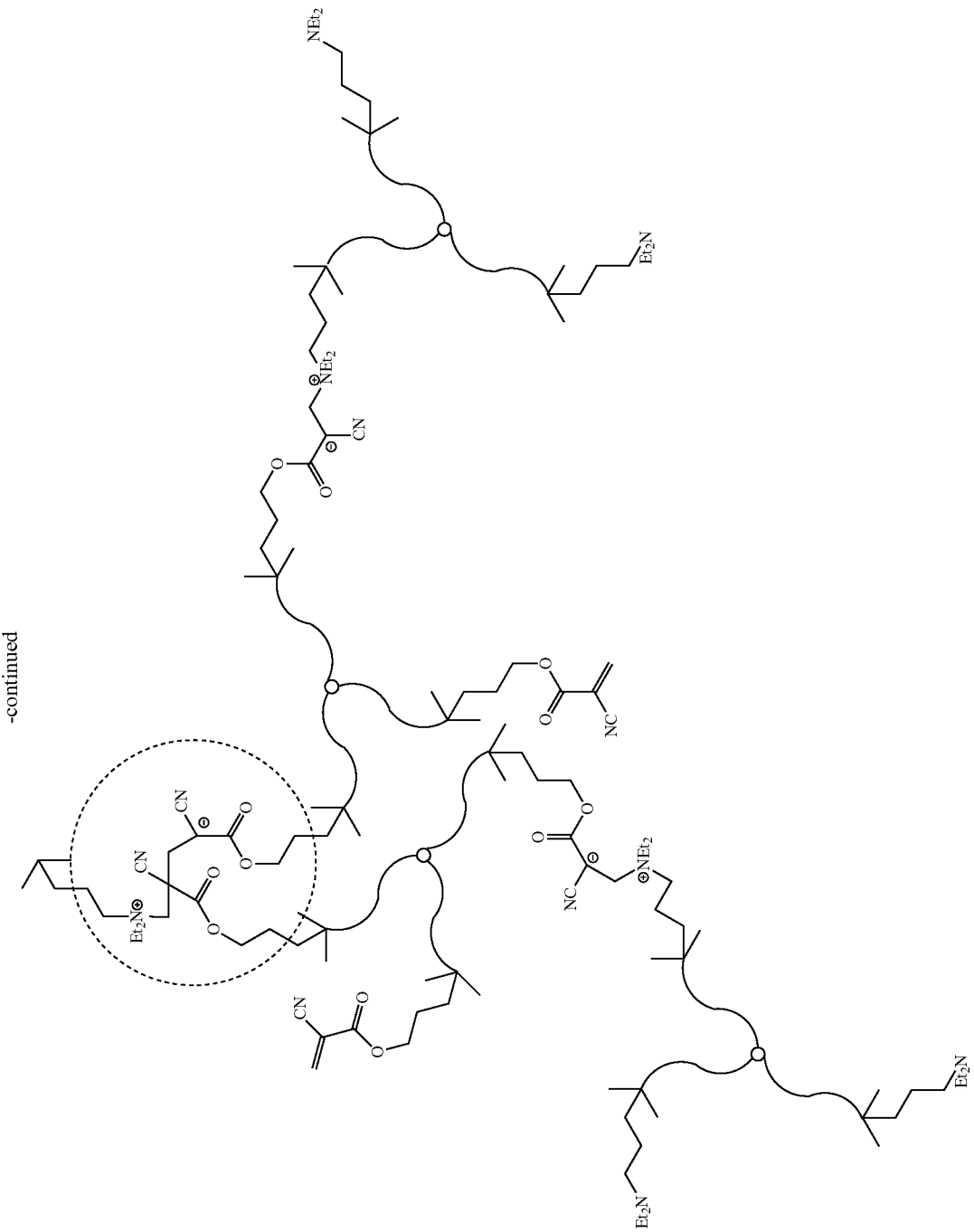

Figure 19:
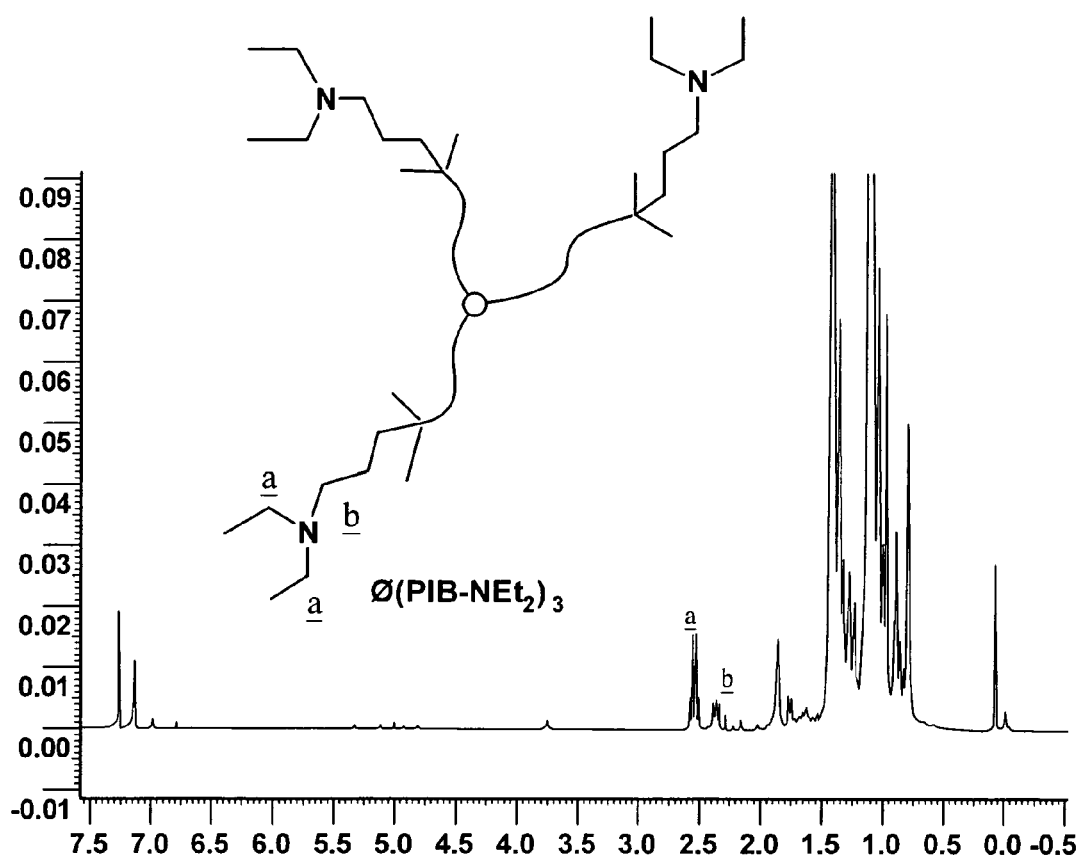
FIG. 19 is a $^1$H NMR spectrum of Ø(PIB-NEt$_2$)$_3$.

The Synthesis and Characterization of Ø(PIB-NEt$_2$)$_3$:

The following procedure is used for the preparation of the three-arm tertiary amine-telechelic PIB, Ø(PIB-NEt$_2$)$_3$. A 500 mL three-neck flask with a magnetic stirrer and condenser is charged with 200 mL dry THF, 40 mL DMF, 15 grams Ø(PIB-Br)$_3$ (3,000 g/mol; 0.005 mole), 12 grams (0.16 moles) diethylamine, and 0.3 grams NaHCO$_3$. After stirring overnight at reflux the solvent is evaporated by a rotavap. Then 100 mL hexanes are added, the system is washed with 100 mL water 3 times, dried over MgSO$_4$, filtered, and the solvent is evaporated by a rotavap at 50° C. The product, Ø(PIB-NEt$_2$)$_3$, is a clear, colorless, transparent, viscous liquid. The yield is 14 grams and the absence of —CH$_2$—Br indicates a quantitative reaction. FIG. 19 shows the $^1$HNMR spectrum of Ø(PIB-NEt$_2$)$_3$ together with assignments.

Dual-Syringe Experiments: Polymerization of Ø(PIB-CA)$_3$ and Copolymerization of Ø(PIB-CA)$_3$ Plus TMP-CA, by the Macroinitiator Ø(PIB-NEt$_2$)$_3$:

(a) The Dual-Syringe

To obtain materials of promising mechanical/chemical etc. properties experiments are conducted by the use of dual-syringes (volume ratio of the barrels 4/1) that deliver injectible Ø(PIB-CA)$_3$ in combination with the designed highly reactive tertiary amine macroinitiator, Ø(PIB-NEt$_2$)$_3$. The primary purpose of these exploratory experiments is to demonstrate acceleration of Ø(PIB-CA)$_3$ polymerization by the use of simultaneously ejected "monomer"/macroinitiator systems and, in general, to assess the feasibility of in situ bulk polymerization by dual-syringe delivery.

Figure 20:
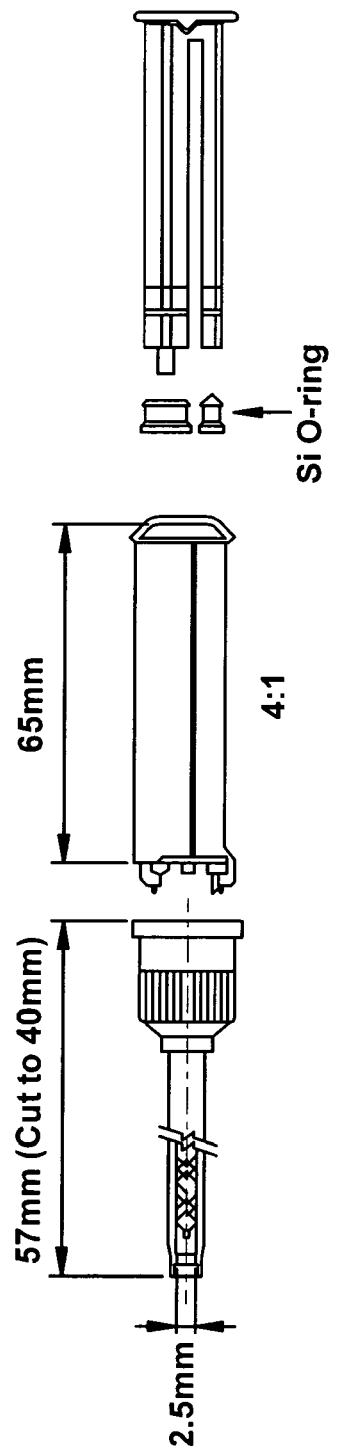
FIG. 20 is an illustration of a dual syringe according to one embodiment of the present invention.

FIG. 20 is a sketch of the dual-syringe used for the various polymerization experiments. The dual-syringes are provided by Medmix systems AG, Switzerland; Syringe (2.5 mL, 4:1, PP natural), and 1.6 inch-long Mixer (DN 2.5×16×4:1, brown, med) with Lure-Tip. The mixing tip is cut to 1 inch (approximately 40 mm) to facilitate injection.

(b) In Situ Polymerization and Copolymerization with the Dual Syringe Technique:

Table 7 summarizes the quantities used and observations made. In the first experimental syringes filled under a nitrogen atmosphere (dry box) one of the barrels of the dual-syringe is filled with Ø(PIB-CA)$_3$ "monomer" and the second barrel is filled with a macroinitiator (Ø(PIB-NEt$_2$)$_3$), both having a M$_w$ equal to 3,000 g/mole. The contents of both barrels are ejected simultaneously onto a glass plate at room temperature. The mole ratio of the starting materials is Ø(PIB-CA)$_3$/Ø(PIB-NEt$_2$)$_3$ is equal to 64/36.

TABLE 7

In situ bulk Polymerization by Simultaneous Injection of Ø(PIB-CA)$_3$, TMP-CA, and Ø(PIB-NEt$_2$)$_3$ Mixtures from a Dual Syringe

| Components | First | | Second | | Third | |
|---|---|---|---|---|---|---|
| | Grams | g/mole | Grams | g/mole | Grams | g/mole |
| Ø(PIB-CA)$_3$* | 0.7 | 0.0007 | 0.7 | 0.0007 | 0.7 | 0.0007 |
| TMP-CA | 0 | 0 | 0.3 | 0.0015 | 0.3 | 0.0015 |
| Ø(PIB-NEt$_2$)$_3$ | 0.4 | 0.0004 | 0.2 | 0.0002 | 0.04 | 0.00004 |
| Mineral Oil** | | | | 0.2 | | 0.36 |
| ΣCA/Ø(PIB-NEt$_2$)$_3$ | | 64/36 | | 90/10 | | 98/2 |
| [ΣCAs+ Ø(PIB-NEt$_2$)$_3$]/mineral oil | 100/0 | | 86/14 | | 74/26 | |
| Ø(PIB-CA)$_3$/ TMP-CA/ Ø(PIB-NEt$_2$)$_3$ | 64/0/36 | 64/0/36 | 58/25/ 17 | 30/62/8 | 67/29/4 | 31/67/2 |

TABLE 7-continued

In situ bulk Polymerization by Simultaneous Injection of Ø(PIB-CA)$_3$, TMP-CA, and Ø(PIB-NEt$_2$)$_3$ Mixtures from a Dual Syringe

| Components | First | | Second | | Third | |
|---|---|---|---|---|---|---|
| | Grams | g/mole | Grams | g/mole | Grams | g/mole |
| Observations | Hard to push the plunger Immediate network formation; soft rubbery product | | Immediate network formation Leathery product Insoluble in THF | | Network formed slowly Weak, soft product Insoluble in THF | |

*M$_n$ = 3000 g/mol
**Mineral oil to dilute Ø(PIB-NEt$_2$)$_3$

Polymerization ensued essentially instantaneously and a very soft slightly yellow rubber formed exhibiting reasonable mechanical properties by manual manipulation. While not wishing to be bound to any one theory, evidently the tertiary amine end groups induce the polymerization of the Ø(PIB-CA)$_3$ and a crosslinked rubber is formed. The product is insoluble in THF, which indicates network formation; due to the insolubility of the product one cannot determine the M$_w$. Since both the Ø(PIB-CA)$_3$ and Ø(PIB-NEt$_2$)$_3$ are mostly PIB, incompatibility of the ingredients is not an issue.

After having ascertained that the dual-syringe delivery method is suitable for in situ bulk polymerization, further experiments are carried out in which one of the barrels is filled with a mixture of "monomers", i.e., Ø(PIB-CA)$_3$ plus TMP-CA, and the other with the macroinitiator Ø(PIB-NEt$_2$)$_3$. TMP-CA is a liquid and therefore functions as a solvent for Ø(PIB-CA)$_3$ and, desirably, reduces its viscosity. To increase the volume of the small amount of the macroinitiator needed, the Ø(PIB-NEt$_2$)$_3$ is diluted with mineral oil laxative (Nujol) in the smaller barrel. Simultaneous ejection of the contents of the two barrels onto a glass plate results in immediate polymerization. Table 7 summarizes the quantities used and the observations made. Polymerization is essentially instantaneous in the presence of 8 mole percent of Ø(PIB-NEt$_2$)$_3$, whereas it is somewhat slower with 2 mole percent. The mechanical properties of the products are noticeably different.

These experiments indicate that crosslinked PIB with promising mechanical properties are prepared in situ in bulk extremely rapidly (within seconds or minutes) by the dual-syringe technique.

Polymerization of Ø(PIB-CA)$_3$ to Networks and Copolymerization of Ø(PIB-CA)$_3$/TMP-CA Mixtures to Co-Networks by DMT:

DMT is a highly reactive initiator for the polymerization of Ø(PIB-CA)$_3$ and copolymerization of Ø(PIB-CA)$_3$/TMP-CA mixtures. Table 6 summarizes composition and stress/stain properties of the polymers and copolymers obtained under certain conditions. Analysis of the data suggests that the mechanical properties could be improved by decreasing the concentration of the DMT. Subsequent experiments carried out with a lower DMT concentration corroborate this theory. Table 8 combines this data and specifies experimental conditions. The relative quantities of TMP-CA in the copolymers are essentially the same; however, the corresponding stress/strain properties obtained are noticeably improved over those summarized above.

TABLE 8

Mechanical Properties of a Ø(PIB-CA)$_3$ Network
and Three Ø(PIB-CA)$_3$/TMP-CA Co-Networks*

| Network | TMP-CA Wt % | Mole % | Stress MPa | Strain % |
|---|---|---|---|---|
| {[Ø(PIB-CA)$_3$] + [TMP-CA]}/[DMT] = approximately 9 | | | | |
| Ø(PIB-CA)$_3$ | 0 | 0 | 0.55 | 48 |
| Ø(PIB-CA)$_3$/TMP-CA5 | 5 | 33 | 0.8 | 45 |
| Ø(PIB-CA)$_3$/TMP-CA12 | 12 | 39 | 1.2 | 98 |
| Ø(PIB-CA)$_3$/TMP-CA30 | 30 | 70 | 2.3 | 195 |
| {[Ø(PIB-CA)$_3$] + [TMP-CA]}/[DMT] = approximately 30 | | | | |
| Ø(PIB-CA)$_3$ | 0 | 0 | 1.1 | 56 |
| Ø(PIB-CA)$_3$/TMP-CA5 | 5 | 33 | 1.5 | 95 |
| Ø(PIB-CA)$_3$/TMP-CA15 | 15 | 46 | 2.3 | 150 |
| Ø(PIB-CA)$_3$/TMP-CA42 | 42 | 76 | 3.7 | 207 |

*Average of three determinations

Figure 21:
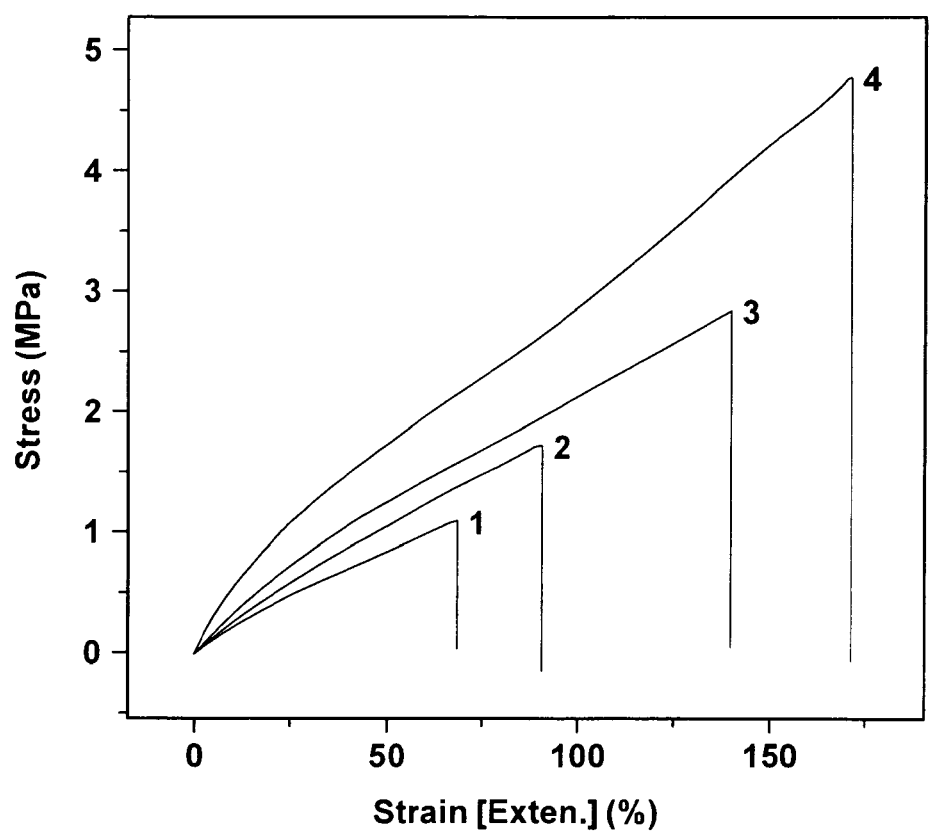
FIG. 21 is a graph of stress versus strain plots: (1) 0 mole percent TMP-CA; (2) 33 mole percent TMP-CA; (3) 47 mole percent TMP-CA; and (4) 76 mole percent TMP-CA.

FIG. 21 is a graph illustrating stress/strain plots of the various materials prepared. The Ø(PIB-CA)$_3$ network exhibits 1.1 MPa stress and 56% strain. The addition of increasing amounts (i.e., 5, 15 and 42 weight percent) of TMP-CA produces co-networks with improved stress/stain values. Specifically, FIG. 21 is a stress versus strain plots for: (1) 0 mole percent TMP-CA; (2) 33 mole percent TMP-CA; (3) 47 mole percent TMP-CA; and (4) 76 mole percent TMP-CA.

barrel syringe technique. Co-network formation is instantaneous and soft light tan rubbers are obtained. The color of the products deepened to rust upon heating/drying. Visual and manual examination of the rubbers show promising properties. Samples 2, 3, and 4 in Table 9 provide details;

(3) The T$_g$'s of the various materials are determined and can be controlled based on the starting materials; and (4) The thermal stability of various products is studied by TGA.

Bulk Preparation of Ø(PIB-CA)$_3$ Homo-Networks and Ø(PIB-CA)$_3$/TMP-Co-Networks:

Polymerization of Ø(PIB-CA)$_3$ (M$_n$ equal to 2850 g/mole) to homo-networks and the copolymerization of Ø(PIB-CA)$_3$/TMP-CA mixture to co-networks, both reactions mediated by the Ø(PIB-NEt$_2$)$_3$ (M$_n$ equal to 3,000 g/mol) macroinitiator and using the double-barreled syringe technique, are continued.

Figure 22:
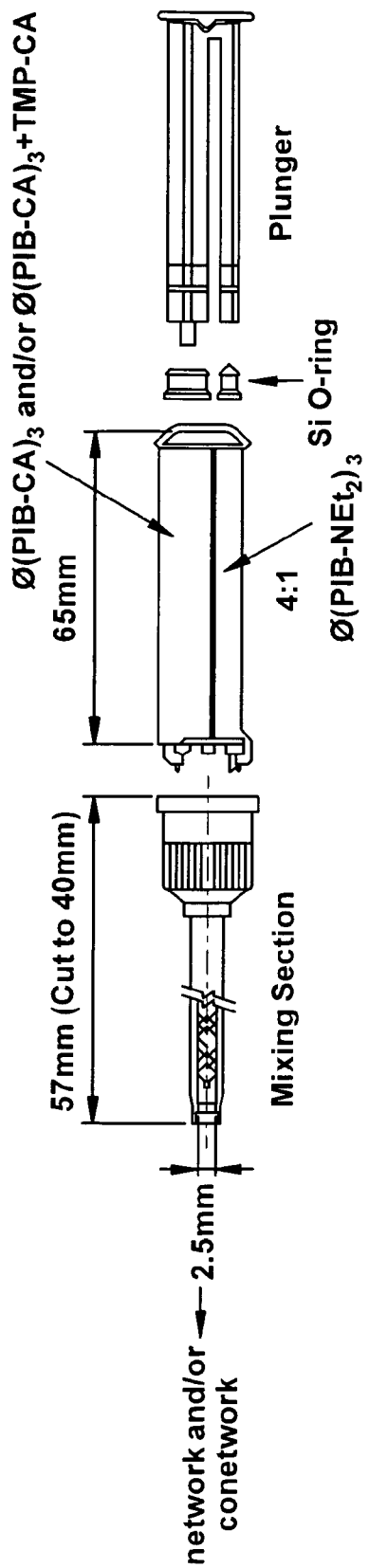
FIG. 22 is an illustration of one embodiment of a dual syringe system used for the bulk polymerization of Ø(PIB-CA)$_3$ and copolymerization of Ø(PIB-CA)$_3$/TMP-CA by the Ø(PIB-NEt$_2$)$_3$ macroinitiator.

The objective is to find conditions for convenient manual siringibility, and instantaneous polymerizations, i.e., homo- and co-network formation. FIG. 22 shows the scheme of the double-barrel syringe and the placement of the ingredients in the barrels, and Table 9 summarizes initial results.

The consistencies of both Ø(PIB-CA)$_3$ and Ø(PIB-NEt$_2$)$_3$ are similar to honey, however, they are readily miscible. Pushing these two ingredients into the mixing chamber instantaneously produces the target PIB homo-network, and the product emerges as a strip of soft rubber at the tip of the mixing needle. The needle is cut to 40 mm (from the original 57 mm) to shorten the passage of the rubber in the mixing needle and to facilitate the collection of the product.

TABLE 9

In situ Bulk Polymerization by Simultaneous Injection of
Ø(PIB-CA)$_3$, and Ø(PIB-CA)$_3$/TMP-CA Mixtures,
by the Ø(PIB-NEt$_2$)$_3$ Macroinitiator Using a Dual-Barrel Syringe

| Reactants | Sample 1 g | g/mol | Sample 2 g | g/mol | Sample 3 g | g/mol | Sample 4 g | g/mol |
|---|---|---|---|---|---|---|---|---|
| Ø(PIB-CA)$_3$* | 0.90 | 0.0009 | 0.85 | 0.00085 | 0.7 | 0.0007 | 0.7 | 0.0007 |
| TMP-CA | 0 | 0 | 0.15 | 0.00073 | 0.3 | 0.0015 | 0.5 | 0.0024 |
| Ø(PIB-NEt$_2$)$_3$** | 0.2 | 0.0002 | 0.25 | 0.00025 | 0.28 | 0.00028 | 0.3 | 0.0003 |
| Ø(PIB-CA)$_3$/TMP-CA/ Ø(PIB-NEt$_2$)$_3$ | 82/0/18 | 82/0/18 | 68/12/20 | 47/39/14 | 55/24/21 | 28/60/12 | 46/33/21 | 20/71/9 |
| THF Extractables (%) | 5.3 | | 3.2 | | 3 | | 4.8 | |
| Observations | Hard to push the plunger manually; Immediate network formation; Soft, light tan, non-tacky rubber, Color does not change upon drying in vacuum for one day at 100° C. | | Immediate network formation, Mild manual pressure sufficient to push the plunger; Light tan, soft rubber, color changes to reddish light brown upon drying in vacuum for one day at 100° C. | | Immediate network formation, Mild manual pressure sufficient to push the plunger; Light tan, soft rubber, color changes to reddish light brown upon drying in vacuum for one day at 100° C. | | Immediate network formation, Mild manual pressure sufficient to push the plunger; Light tan, soft tan color changes to reddish light brown upon drying in vacuum for one day at 100° C. | |

*M$_n$ = 2850 g/mole, and
**M$_n$ = 3000 g/mole

Additional Embodiments

Section III

In this section the following items are addressed and/or discussed:

(1) Conditions are developed for the preparation of PIB networks by in situ bulk polymerization of Ø(PIB-CA)$_3$ mediated by the Ø(PIB-NEt$_2$)$_3$ macroinitiator by the double-barrel syringe. Co-injection of these ingredients essentially instantaneously yields soft rubbers;

(2) A series of co-networks are prepared in bulk by contacting various compositions of Ø(PIB-CA)$_3$/TMP-CA mixtures with the Ø(PIB-NEt$_2$)$_3$ macroinitiator using the double- The ejecting of the co-network from the syringe is easier than that of the homo-network because the TMP-CA is a liquid and acts as a solvent and lowers the viscosity of the Ø(PIB-CA)$_3$/TMP-CA charge. The charge is united with the Ø(PIB-NEt$_2$)$_3$ macroinitiator by mild manual pressure, and copolymerization is instantaneous.

THF extraction of both the homo- and the co-networks yielded less than approximately 5% extractables, indicating a high degree of crosslinking (see Table 9). Prior to shipment, the products are extracted by THF and water, and dried.

Oxidative Stability Studies:

Rubbery sheets are prepared by contacting Ø(PIB-CA)$_3$ in toluene with DMT initiator and pouring the charge in Teflon molds at room temperature. Similarly, Ø(PIB-CA)$_3$/TMP- CA mixtures are copolymerized with DMT to yield co-networks. The sheets are dried, washed with water and dried in a vacuum oven for 48 hours at 70° C. Representative samples are placed in boiling concentrated nitric acid for one hour. Table 10 shows sample compositions and visual observations.

TABLE 10

Visual Observations after Contact with Boiling Nitric Acid for One Hour

| Network | TMP-CA | | Visual observations |
|---|---|---|---|
| Solution cast films | Wt % | Mole % | |
| Ø(PIB-CA)$_3$ | 0 | 0 | Elongation unchanged; Sample integrity maintained |
| Ø(PIB-CA)$_3$/TMP-CA20 | 20 | 47 | Elongation increases; Sample integrity maintained |
| Ø(PIB-CA)$_3$/TMP-CA35 | 35 | 76 | Elongation increases; Sample integrity maintained |

All the samples retain their shape integrity. The elongation of the homo-network does not change upon manual stretching. In contrast, the co-networks exhibited increased elongation after boiling in concentrated HNO$_3$ for 1 hour.

Figure 23:
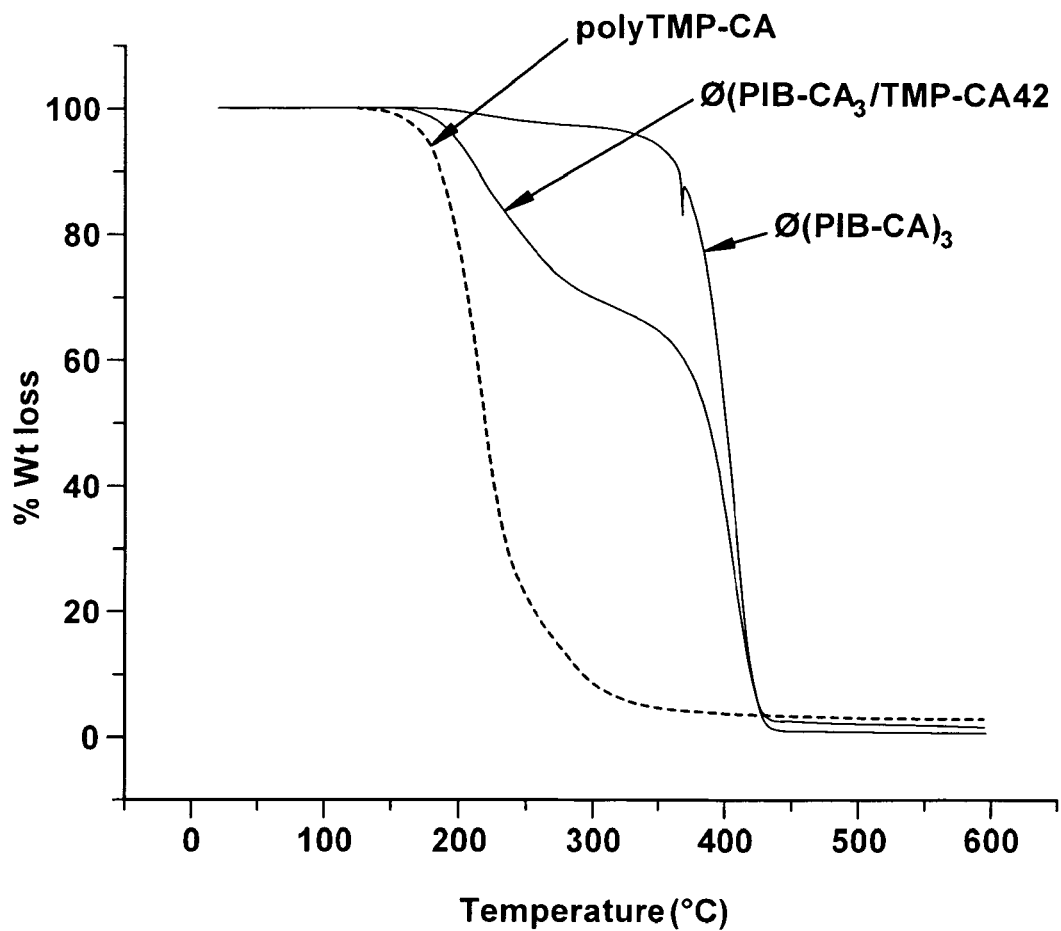
FIG. 23 is a graph illustrating TGA thermograms of poly (TMP-CA, a homo-network and a co-network (10° C./min, N$_2$ atm)

Thermal Stability:

The thermal stability of the poly(TMP-CA), the homo-network obtained with Ø(PIB-CA)$_3$, and the Ø(PIB-CA)$_3$/TMP-CA42 co-network are compared by TGA. FIG. 23 shows the results. Evidently, the thermal stability profile of the homo-network is far superior to poly(TMP-CA). The thermal stability of the Ø(PIB-CA)$_3$/TMP-CA42 co-network is in between that of the poly(TMP-CA) and the homo-network.

T$_g$ Studies:

The knowledge of the T$_g$s of the products of the present invention is important to the design of appropriate materials for the intended applications (sub-dermal or inter-vertebral). Table 11 summarizes the T$_g$s of a homo-network obtained from Ø(PIB-CA)$_3$, two co-networks prepared with Ø(PIB-CA)$_3$/TMP-CA mixtures (15 and 42 weight percent TMP-CA), and a poly(TMP-CA) homo-polymer. The last column in Table 11 shows T$_g$'s calculated by the Fox equation. The T$_g$ of the co-network made with 15% TMP-CA is very close to the theoretical value, indicating that the copolymer is statistical, and that our view of the polymerization mechanism is correct. The T$_g$ of the copolymer made with 42% TMP-CA is also within the expected range, however, in this case the experimental T$_g$ range is broad indicating the presence of a mixture of products.

The poly(TMP-CA), a new polymer, is synthesized by adding 0.01 mL N,N-dimethyl-p-toluidine (DMT) to 2 grams TMP-CA dissolved in 8 mL dry toluene, and stirring the mixture for 1 hour. The solvent is evaporated and the product dried under vacuum for 2 days.

TABLE 11

Glass Transition Temperatures of the Ø(PIB-CA)$_3$ Homo-Network, Two Ø(PIB-CA)$_3$/TMP Co-Networks, and Poly(TMP-CA)

| Network/polymer | TMP-CA Wt % | Mole % | T$_g$ (experimental) ° C. | Calculated by the Fox Equation |
|---|---|---|---|---|
| Ø(PIB-CA)$_3$* | 0 | 0 | −38 | — |
| Ø(PIB-CA)$_3$/TMP-CA15* | 15 | 47 | −34 | −30 |
| Ø(PIB-CA)$_3$/TMP-CA42* | 42 | 76 | −35 to 35 broad range | −15 |
| polyTMP-CA** | — | — | 35 | — |

*by DMTA,
**by DSC

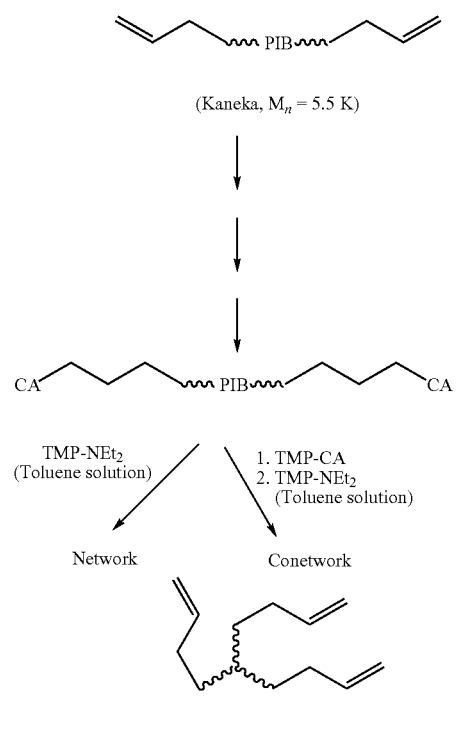

Reaction Scheme 8

Orienting Experiments for Bulk Polymerization

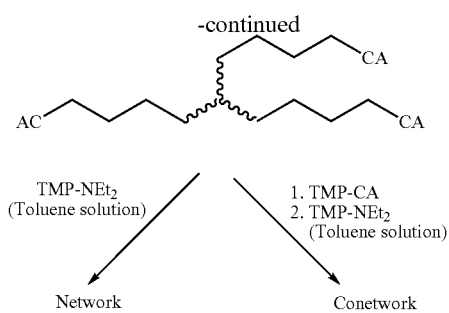

Additional Embodiments

Section IV

In this section the following items are addressed and/or discussed:

(1) It appears that, in one embodiment, the Ø(PIB-CA)$_3$+ Ø(PIB-NEt$_2$)$_3$ macroinitiator system, possibly in conjunction with less than about 15% TMP-CA produces an injectible, essentially instantaneously bulk polymerizable, biocompatible, biostable, rubbery, spinal prosthesis—bulking agent with good mechanical properties;

(2) Experiments show that this combination of ingredients can be delivered by an 18 gauge twin-barrel syringe, and that the bulk polymerization of the system yields, within seconds-to-minutes, rubbers of promising mechanical properties (manual examination);

(3) The oxidative-acid resistance of Ø(PIB-CA)$_3$ networks and Ø(PIB-CA)$_3$/TMP-CA co-networks are studied by exposure to concentrated (65%) nitric acid at room temperature and at 100° C. (boiling acid). While commercial polyether- and PDMS-based polyurethane samples (controls) degraded/dissolved within seconds to minutes under these conditions and therefore their mechanical properties could not be determined, the mechanical properties of Ø(PIB-CA)$_3$-based networks and co-networks declined only moderately; and (4) According to IR spectra, the absorption associated with the —CN group in a Ø(PIB-CA)$_3$/TMP-CA-30% co-network remains unchanged even after 1 hr exposure to boiling concentrated nitric acid. Evidently, the integrity of the co-network is protected by the PIB chains.

Experiments:

Experimentation is conducted on two fronts: (a) to optimize the bulk preparation of homo-networks of Ø(PIB-CA)$_3$ ($M_n$ equal to 3,000 g/mol), and co-networks, both mediated by the Ø(PIB-NEt$_2$)$_3$ ($M_n$ equal to 3,000 g/mol) macroinitiator; and (b) orienting experiments are carried out by conventional (solution) laboratory technique to gather information as to the rate of the crosslinking, and the mechanical properties of networks. Solution experiments provide rate information and sheets for Instron testing; the samples ("worms") obtained by crosslinking in bulk with the twin-barrel syringe are unsuitable for routine physical property measurements.

Table 12 summarizes the experiments performed.

TABLE 12

Summary of Variation of Hardness and Rate of Polymerization with Type of Initiator and Initiator Concentration

| Network/Co-Network Orienting Solution Experiments | TMP-CA Wt % | Mole % | Initiator | [-CA]/[I]* | Hardness (Durometer) | Rate of polymerization (Visual) |
|---|---|---|---|---|---|---|
| Ø(PIB-CA)$_3$ | 0 | 0 | DMT | 30 | 21 | Slow (4-5 h) Promising properties |
| Ø(PIB-CA)$_3$/TMP-CA20 | 20 | 47 | DMT | 30 | 36 | Slow (4-5 h) Promising properties |
| Ø(PIB-CA)$_3$/TMP-CA35 | 35 | 76 | DMT | 30 | 45 | Slow (4-5 h) Promising properties |
| Ø(PIB-CA)$_3$ | 0 | 0 | Ø(PIB-NEt$_2$)$_3$. | 20 | 9 | Slow (4-5 h) Promising properties |
| Ø(PIB-CA)$_3$/TMP-CA20 | 20 | 47 | Ø(PIB-NEt$_2$)$_3$. | 40 | 20 | Slow (4-5 h) Promising properties |
| Ø(PIB-CA)$_3$/TMP-CA35 | 35 | 76 | Ø(PIB-NEt$_2$)$_3$. | 44 | 34 | Slow (4-5 h) Promising properties |
| Ø(PIB-CA)$_3$ | 0 | 0 | Ø(PIB-NEt$_2$)$_3$. | 40 | 6 | Very slow Weak network |
| Ø(PIB-CA)$_3$/TMP-CA20 | 20 | 47 | Ø(PIB-NEt$_2$)$_3$. | 30 | 15 | Slow(2-3 h) Weak network |
| Ø(PIB-CA)$_3$/TMP-CA35 | 35 | 76 | Ø(PIB-NEt$_2$)$_3$. | 30 | 22 | Immediate Weak network |
| Bulk experiments using the twin-barrel syringe | | | | | | |
| Ø(PIB-CA)$_3$ | 0 | 0 | Ø(PIB-NEt$_2$)$_3$ | 4.5 | 10-18* | immediate network formation |
| Ø(PIB-CA)$_3$/TMP-CA-20 | 20 | 47 | Ø(PIB-NEt$_2$)$_3$. | 6.2 | 20-28* | immediate co-network formation |

TABLE 12-continued

Summary of Variation of Hardness and Rate
of Polymerization with Type of Initiator and Initiator Concentration

| Network/Co-Network Orienting Solution Experiments | TMP-CA Wt % | TMP-CA Mole % | Initiator | [-CA]/[I]* | Hardness (Durometer) | Rate of polymerization (Visual) |
|---|---|---|---|---|---|---|
| Ø(PIB-CA)$_3$/TMP-CA-35 | 35 | 76 | Ø(PIB-NEt$_2$)$_3$. | 10.3 | 30-35* | immediate co-network formation |
| Ø(PIB-CA)$_3$ | 0 | 0 | Fresh chicken egg | — | 8-12* | THF insoluble slow polymerization |

*Approximate values of virgin un-extracted samples obtained by manually pressing crosslinked materials to plugs and measuring hardness. Wide range of data are due to sample inhomogeneity.

The information generated is now summarized and briefly discussed:

(i) The Ø(PIB-CA)$_3$+Ø(PIB-NEt$_2$)$_3$ macroinitiator combination, under suitable conditions, yields the target injectible spine prosthesis/bulking agent. Orienting experiments suggest that, in one embodiment, the mole ratio of cyano-acrylate (CA) to initiator (I) is in the range of about 15 to about 30. Although, the present invention is not limited to just this range. This mole ratio is obtained by adjusting the ingredient concentrations and molecular weights.

(ii) The CA/I ratio can be increased (i.e., the I portion is lowered) by the use lower molecular weight (approximately 1,500 to 2,000 g/mol) Ø(PIB-CA)$_3$, or by use of linear (not three-arm) NEt$_2$-PIB-NEt$_2$ of a relatively high molecular weight ($M_n$ is at least about 5,000 g/mol). Because of the telechelic nature of this macroinitiators dangling chain ends will be absent and the macroinitiator is part of the networks.

(iii) The mechanical properties of the networks are controlled by the molecular weight of the ingredients, possibly together with the amount of TMP-CA added.

(iv) Experiments show that Ø(PIB-CA)$_3$/TMP-CA mixtures containing up to approximately 15% TMP-CA are optically clear and homogeneous. Above approximately 15% TMP-CA the mixtures become slightly hazy. Thus, we can use up to approximately 15% TMP-CA to stiffen (harden) our bulk delivered products.

(v) TMP-CA is a liquid and up to approximately 15% of it is a diluent for Ø(PIB-CA)$_3$, thus it facilitates siringibility of Ø(PIB-CA)$_3$/TMP-CA mixtures. In contrast, optically hazy mixtures are obtained when even small amounts of Et-CA are added to Ø(PIB-CA)$_3$ of $M_n$ equal to 3,000 g/mol in the bulk. While not wishing to be bound to any one theory, evidently Et-CA is incompatible with PIB.

(vi) TMP-CA polymerizes in contact with proteins. Therefore, TMP-CA injected onto fresh chicken eggs polymerizes rapidly.

(vii) TMP-CA is expected to be bio-acceptable. Polymers of Me- and Et-CA are cytotoxic, however, the toxicity of CA polymers decreases and their biocompatibility increases with increasing molecular weight and branching of the pendant alkyl group.

(viii) The long PIB moiety insures that the viscosities of this macroinitiator and that of Ø(PIB-CA)$_3$ are similar; this is important for twin-barrel syringe delivery.

Figure 24:
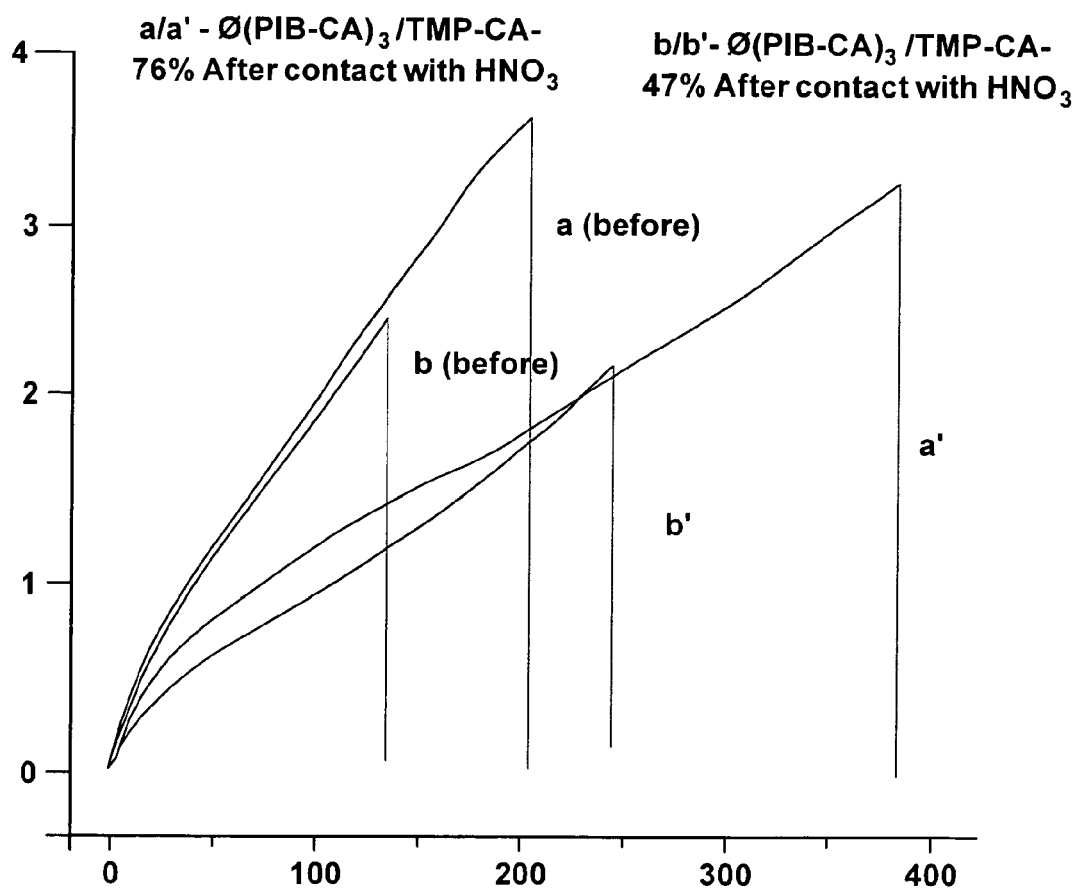
FIG. 24 is a graph illustrating stress versus strain of two co-networks before and after contact with boiling nitric acid for 1 hour

Oxidative Stability of Networks:

The oxidative stability of networks and co-networks is investigated by exposure to concentrated nitric acid. Thus dumbbells (2.5 cm long, 0.35 cm width at the neck) are prepared by solution casting films of Ø(PIB-CA)$_3$ and various co-networks of Ø(PIB-CA)$_3$/TMP-CA (and crosslinked with DMT initiator). The samples are immersed in boiling concentrated nitric acid for 1 hour and after washing with water and vacuum drying, THF extractables, stress-strain properties and hardness are determined. Table 13 and FIG. 24 show the data before and after contact with nitric acid. The controls (a crosslinked PDMS and a commercially available PU) dissolve within minutes and yield oily droplets after 15 minutes contact with the acid at room temperature. Independent experiments show that P(Et-CA) also dissolved (probably degraded) upon a few minutes contact with concentrated nitric acid at room temperature.

TABLE 13

Oxidative Degradation Tests of Network and
Co-Networks with Concentrated Boiling Nitric Acid (1 h)
in terms of Mechanical Properties and Extractables

| Network* | TMP-CA Wt % | TMP-CA Mole % | Stress (MPa) Before Oxidation | Stress (MPa) After Oxidation | Strain (%) Before Oxidation | Strain (%) After Oxidation | THF Extractables (%) After Oxidation |
|---|---|---|---|---|---|---|---|
| Ø(PIB-CA)$_3$ | 0 | 0 | 1 | 0.7 | 65 | 45 | 5 |
| Ø(PIB-CA)$_3$/TMPCA5 | 5 | 33 | 1.3 | 0.9 | 80 | 90 | 4 |
| Ø(PIB-CA)$_3$/TMP-CA15 | 15 | 47 | 2.6 | 2.2 | 140 | 250 | 4.5 |
| Ø(PIB-CA)$_3$/TMP42 | 42 | 74 | 3.6 | 3.0 | 170 | 380 | 6 |
| Crosslinked PDMS and PDMS-polyurethane (RT, >15 min.) | | | Dissolves within minutes, oily droplets form | | | | |

*prepared by using DMT initiator in toluene solution.

The stresses decrease and elongations increase suggesting a small extent of lowering of the crosslink density. The small amounts of extractables also suggest a small degree of degradation.

Table 14 shows the hardness of a representative network and two co-networks before and after oxidative degradation with boiling and room temperature nitric acid.

TABLE 14

Summary of Hardness Before and After Contact with $HNO_3$

| Network/ polymer Solution cast films | TMP-CA | | Hardness (Microshore) | | |
|---|---|---|---|---|---|
| | Wt % | Mole % | Before ox. | After contact with boiling $HNO_3$ for 1 h | After contact with r.t. $HNO_3$ for 1 day |
| Ø(PIB-CA)$_3$ | 0 | 0 | 21 | 12 | 18 |
| Ø(PIB-CA)$_3$/TMP-CA20 | 20 | 47 | 36 | 17 | 27 |
| Ø(PIB-CA)$_3$/TMP-CA35 | 35 | 76 | 45 | 32 | 38 |

Figure 25:
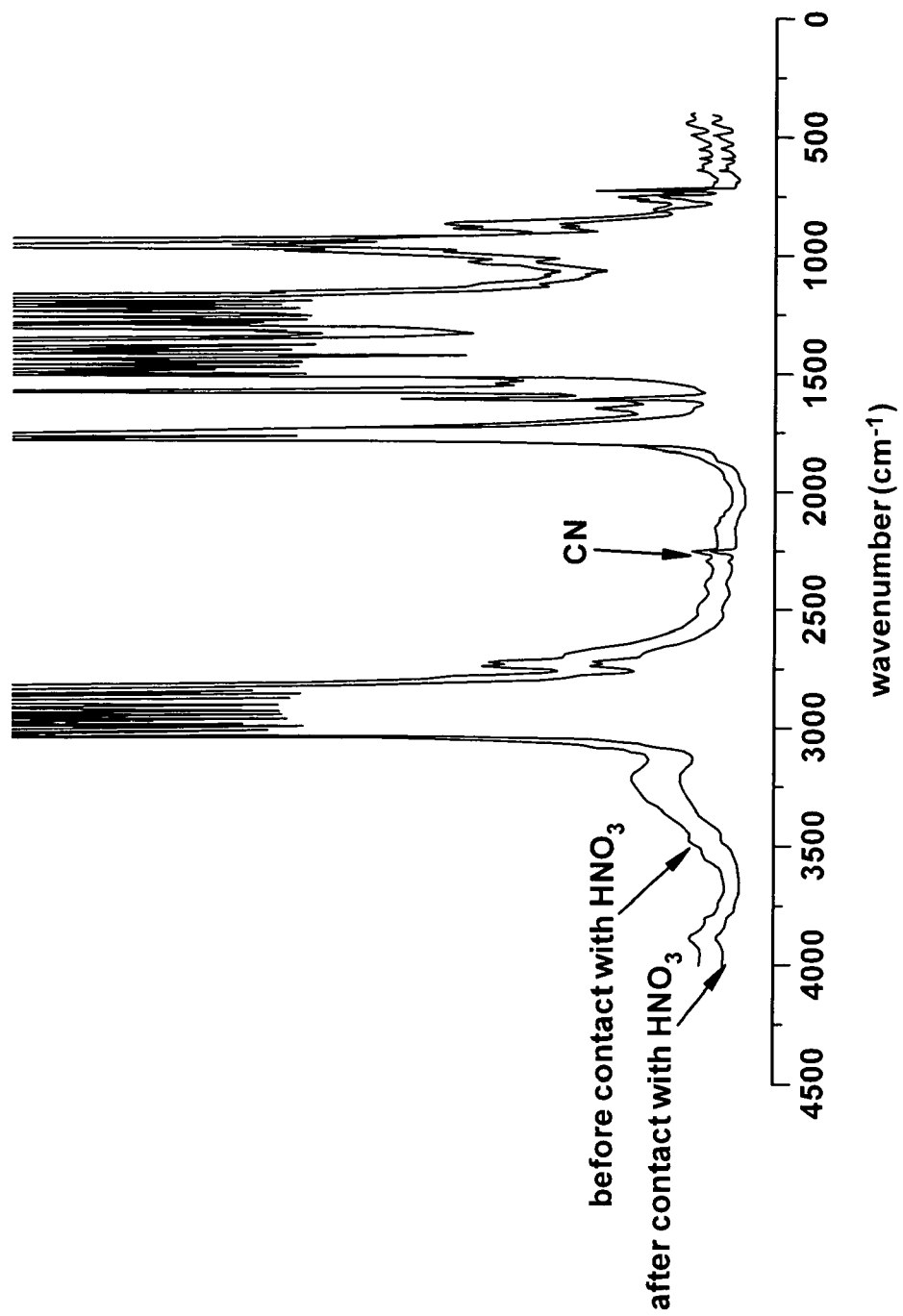
FIG. 25 is an FTIR spectra of a Ø(PIB-CA)$_3$/TMP30 co-network before and after contact with boiling nitric acid for 1 hour.

The oxidative-acid resistance of Ø(PIB-CA)$_3$/TMP-CA co-networks is demonstrated by IR spectroscopy. Thus a Ø(PIB-CA)$_3$/TMP-CA30 co-network is exposed to boiling concentrated nitric acid for 1 hour, and the —CN absorption is examined before and after acid contact. The —CN group readily hydrolyzes to —CCOH by acids. As shown by the spectra in FIG. 25, the —CN absorption does not change after $HNO_3$ exposure, indicating the protection of —CN groups by PIB moieties.

Additional Embodiments

Section V

In this section the following items are addressed and/or discussed:

(1) Ø(PIB-CA)$_3$+Ø(PIB-NEt$_2$)$_3$ combinations essentially instantaneously yield in the bulk upon injection with a double-syringe rubbery products with promising mechanical properties for select medical applications, e.g., inter-vertebral discs, subcutaneous anti-wrinkle bulking agent;

(2) The molecular weights of the starting materials and the monomer/initiator ratio, i.e., [-CA]/[-NEt$_2$], control the rate of polymerization and the properties of the rubber. With $M_n$ approximately 3,000 g/mole starting materials the best balance of rates and properties are obtained with [-CA]/[-NEt$_2$]= 16;

(3) Both the rate and mechanical properties of the rubbers are enhanced by the use of up to 15% TMP-CA co-monomer; and (4) The objective is to obtain preliminary bio-acceptability data of the starting materials [Ø(PIB-CA)$_3$, Ø(PIB-NEt$_2$)$_3$ and TMP-CA] and the instantaneously bulk polymerized rubber.

Instantaneous Bulk Polymerization of Ø(PIB-CA)$_3$ and Ø(PIB-CA)$_3$+TMP-CA Mixtures by the Ø(PIB-Net$_2$)$_{2\ or\ 3}$ Initiator Using the Double-Syringe Technique:

Reactions between Ø(PIB-CA)$_3$ plus Ø(PIB-NEt$_2$)$_{2\ or\ 3}$, and Ø(PIB-CA)$_3$/TMP-CA plus Ø(PIB-NEt$_2$)$_{2\ or\ 3}$ are effected in the bulk by the use of double-syringes (barrel ratios 4:1 and 10:1). Thus, Ø(PIB-CA)$_3$ or Ø(PIB-CA)$_3$/TMP-CA mixtures are placed into the larger barrel of the double-syringe, and the Ø(PIB-NEt$_2$)$_{2\ or\ 3}$ initiator are placed in the smaller barrel, and reactions are initiated by propelling the charges into the mixing tip of the syringe, in fact the reactor. Reaction (i.e., zwitter-ion formation, and possible polymerization and copolymerization of the CA groups) is essentially instantaneous and the products emerged as strips at the end of the mixing tip.

Because the products that emerge at the mixing tip of the syringe are heterogeneous and crosslinked, and most likely may have suffered some stress fracture upon extrusion, the options for product characterization are limited. The extent of extractables (sol fractions) are determined and visual/manual examinations are preformed.

Table 15 summarizes the results of bulk polymerization experiments. Depending on the barrel ratio of 4:1 and 10:1 of the double-syringe used, the data are subdivided into two groups.

The first group of four experiments in Table 15 shows the effect of increasing amounts of TMP-CA on the products. In these experiments the TPM-CA is mixed with the Ø(PIB-CA)$_3$ and the mixture placed in the larger barrel of the syringe and is injected together with the Ø(PIB-NEt$_2$)$_3$ placed in the smaller barrel.

TABLE 15

Summary of Bulk Polymerizations of Ø(PIB-CA)$_3$ and Co-Polymerizations of Ø(PIB-CA)/TMP-CA Mixtures by the Use of Double Syringes

| | | TMP-CA | | | | | Remarks, observations | |
|---|---|---|---|---|---|---|---|---|
| No. | Network/Co-Network | Wt % | Mole % | Initiator | [-CA]/[-NEt$_2$] | Extractables* (%) | Rate of pzn (visual obs.) | Mech. Props. (manual exam.) |
| Barrel ratio 4:1 | | | | | | | | |
| 1 | Ø(PIB-CA)$_3$(3K) | 0 | 0 | Ø(PIB-NEt$_2$)$_3$(3K) | 4.5 | 13 | Immediate network formation | Weak, elastic, pulls apart easily, cheesy |
| 2 | Ø(PIB-CA)$_3$(3K)/TMP-CA15 | 15 | 47 | Ø(PIB-NEt$_2$)$_3$(3K) | 6.2 | 13 | Immediate network formation | Soft rubbery, cheesy |
| 3 | Ø(PIB-CA)$_3$(3K)/TMP-CA20 | 20 | 55 | Ø(PIB-NEt$_2$)$_3$(3K) | 9 | 13 | Immediate network formation | Soft rubbery, smells of TMP-CA |
| 4 | Ø(PIB-CA)$_3$(3K)/TMP-CA35 | 35 | 73 | Ø(PIB-NEt$_2$)$_3$(3K) | 12 | 16 | Immediate network formation | Soft rubbery, strong smells of TMP-CA |

TABLE 15-continued

Summary of Bulk Polymerizations of Ø(PIB-CA)$_3$ and
Co-Polymerizations of Ø(PIB-CA)/TMP-CA Mixtures by the Use of Double Syringes

| | | TMP-CA | | | | | Remarks, observations | |
|---|---|---|---|---|---|---|---|---|
| No. | Network/Co-Network | Wt % | Mole % | Initiator | [-CA]/[-NEt$_2$] | Extractables* (%) | Rate of pzn (visual obs.) | Mech. Props. (manual exam.) |
| 5 | Ø(PIB-CA)$_3$(3K) | 0 | 0 | Ø(PIB-NEt$_2$)$_2$(5K) | 11 | 11 | Immediate network formation | Soft rubbery |
| 6 | Ø(PIB-CA)$_3$(3K)/TMP-CA15 | 15 | 47 | Ø(PIB-NEt$_2$)$_2$(5K) | 16 | 11 | Immediate network formation | Strong, odorless, colorless elastic |
| 7 | Ø(PIB-CA)$_3$(5K) | 0 | 0 | Ø(PIB-NEt$_2$)$_2$(5K) | 4 | — | Immediate network formation | Weak, elastic, pulls apart easily, |
| 8 | Ø(PIB-CA)$_3$(5K)/TMP-CA15 | 15 | 47 | Ø(PIB-NEt$_2$)$_2$(5K) | 13 | — | Immediate network formation | Soft rubbery |
| 9 | Ø(PIB-CA)$_3$(3K) | 0 | 0 | Ø(PIB-NEt$_2$)$_3$(3K) Injected in fresh chicken egg | 4.5 | 9 | Immediate network formation | Weak, elastic, pulls apart easily |
| 10 | Ø(PIB-CA)$_3$(3K)/TMP-CA15 | 15 | 47 | Ø(PIB-NEt$_2$)$_{2(5K)}$ Injected in fresh chicken egg Barrel ratio 10:1 | 16 | 9 | Immediate network formation | Strong, colorless elastic |
| 11 | Ø(PIB-CA)$_3$(3K) | 0 | 0 | Ø(PIB-NEt$_2$)$_2$(5K) | 27 | — | Very slow | Remains sticky after 3 days |
| 12 | Ø(PIB-CA)$_3$(3K)/TMP-CA15 | 15 | 47 | Ø(PIB-NEt$_2$)$_3$(5K) | 40 | — | slow | Remains sticky after 3 days |

*Averages of 3 determinations

TMP-CA is a clear liquid and up to 15% TMP-CA gives homogenous solutions with Ø(PIB-CA)$_3$; in the presence of more than 15% TMP-CA the system becomes hazy indicating phase separation. Warming of mixtures containing 20-35% TMP-CA produces homogeneous clear solutions, however, phase separation returns upon cooling to room temperature. Above 35% TMP-CA, the system remains heterogeneous even after prolonged heating to approximately 50° C.

As suggested by the relatively low levels of extractables (13%), crosslinking is efficient in Experiments 1 to 3. The best result in this series of experiments is obtained with [-CA]/[-NEt$_2$] equal to 6.2 (Experiment 2).

The characteristic odor of TMP-CA is noticeable in the product of Experiment 3, and is quite strong in that of Experiment 4. Evidently, TMP-CA is only partially consumed in these experiments. The amount of extractables is largest (16%) in Experiment 4, which is most likely due to the presence of unconverted TPM-CA. Upon air drying for approximately 5 days the smell of TMP-CA decreases.

In Experiments 5 and 6 the [-CA]/[-NEt$_2$] ratio is increased to 11 and 16, respectively, by increasing the molecular weight of the initiator. Increasing the [-CA]/[-NEt$_2$] is expected to increase the molecular weights, i.e., yield better mechanical properties. Indeed, the extractables decreased to 11% and the properties of the products definitively improved as judged by manual examination. The product obtained in Experiment 6 exhibits the best mechanical properties obtained in the 12 experiments summarized in Table 15.

In Experiments 7 and 8 the molecular weight of the Ø(PIB-CA)$_3$ is increased to 5,000 g/mole. However, the mechanical properties obtained are judged to be inadequate (similar to those obtained in Experiment 1 and 2). While not wishing to be bound to any one theory, the higher viscosity of the system most likely reduced the rate of the reaction.

Experiments 9 and 10 are carried out by co-injecting Ø(PIB-CA)$_3$ plus Ø(PIB-NEt$_2$)$_3$, and Ø(PIB-CA)$_3$/TMP-CA15 plus Ø(PIB-NEt$_2$)$_3$ charges into fresh chicken eggs. Earlier experiments show that in the absence of Ø(PIB-NEt$_2$)$_3$, the Ø(PIB-CA)$_3$ or Ø(PIB-CA)$_3$/TMP-CA15 charges when injected into eggs gave relatively slow polymerizations. In Experiments 9 and 10 polymerization reactions to colorless masses are instantaneous and the extent of extractables decreased. Evidently, the moisture in the eggs affected only little the reactions induced by the strong nucleophile Ø(PIB-NEt$_2$)$_3$.

In the last two Experiments, 11 and 12, the [-CA]/[-NEt$_2$] ratio is increased to 27 and 40, respectively. Under these conditions the polymerization reactions are slow and unacceptable sticky products are obtained most likely due to the relatively low initiator concentration.

Preparation of Films of Networks and Co-Networks by Solution Casting to Aid Property Evaluation:

Because polymerizations in the bulk by the use of double syringes provide only subjective/qualitative observations, conventional solution experiments are carried out that provide well-defined films for mechanical property evaluation. In these experiments, solutions of reactants having relative concentrations similar to those used in bulk experiments are mixed, and then films are cast for mechanical property evaluation.

Table 16 summarizes experimental conditions, extractables, mechanical properties and hardness (obtained by Instron and by micro-Shore, respectively,) of films obtained under conditions approximating those used in bulk experiments.

The amounts of extractables in these experiments (5 to 9.5%) are substantially lower than those obtained in bulk, and indicate high degrees of crosslinking.

The first group of three experiments is carried out with the small molecule TMP-NEt$_2$ initiator, expressly prepared for these investigations. According to the data the mechanical properties of the films are good and increase by increasing the [-CA]/[-NEt$_2$] ratio and/or by increasing the TMP-CA concentration in the 12 to 30 range. Because in these experiments the initiator (TMP-NEt$_2$) is mono-functional, the low extractables (5 to 7%) indicate the "polymerization" of CA groups and a high degree of crosslinking. Chemical Structure 1 below shows a likely structural element present in these networks.

TABLE 16

Properties of Films of Networks and Co-Networks Prepared by Solution Casting

| No. | Network/Co-Network | TMP-CA Wt % | TMP-CA Mole % | Initiator | [-CN]/[-NEt$_2$] | Extractables* (%) | Stress (MPa) | Strain (%) | Hardness (Micro shore) |
|---|---|---|---|---|---|---|---|---|---|
| 1 | Ø(PIB-CA)$_3$(3K) | 0 | 0 | TMP-NEt$_2$ | 12 | 7 | 0.7 | 45 | 18 |
| 2 | Ø(PIB-CA)$_3$(3K)/TMP-CA15 | 15 | 47 | TMP-NEt$_2$ | 16 | 5 | 1.4 | 125 | 25 |
| 3 | Ø(PIB-CA)$_3$(3K)/TMP-CA35 | 35 | 73 | TMP-NEt$_2$ | 30 | 5 | 2.6 | 180 | 32 |
| 4 | Ø(PIB-CA)$_3$(3K) | 0 | 0 | Ø(PIB-NEt$_2$)$_2$(5K) | 6 | 9 | 0.3 | 50 | 12 |
| 5 | Ø(PIB-CA)$_3$(3K) | 0 | 0 | Ø(PIB-NEt$_2$)$_2$(5K) | 11 | 7 | 0.6 | 55 | 15 |
| 6 | Ø(PIB-CA)$_3$(3K) | 0 | 0 | Ø(PIB-NEt$_2$)$_2$(5K) | 30 | — | | | Sticky, weak network |
| 7 | Ø(PIB-CA)$_3$(3K)/TMP-CA15 | 15 | 47 | Ø(PIB-NEt$_2$)$_2$(5K) | 8 | 6 | 0.7 | 90 | 16 |
| 8 | Ø(PIB-CA)(3K)/TMP-CA15 | 15 | 47 | Ø(PIB-NEt$_2$)$_2$(5K) | 16 | 8 | 1.2 | 115 | 20 |
| 9 | Ø(PIB-CA)$_3$(3K)/TMP-CA15 | 15 | 47 | Ø(PIB-NEt$_2$)$_2$(5K) | 30 | 7 | 1.0 | 102 | 19 |
| 10 | Ø(PIB-CA)$_3$(3K)/TMP-CA35 | 35 | 73 | Ø(PIB-NEt$_2$)$_2$(5K) | 30 | 5 | 2.1 | 160 | 28 |
| 11 | Ø(PIB-CA)$_3$(3K) | 0 | 0 | Ø(PIB-NEt$_2$)$_3$(3K) | 11 | 9.5 | 0.5 | 57 | 14 |
| 12 | Ø(PIB-CA)$_3$(3K)/TMP-CA15 | 15 | 47 | Ø(PIB-NEt$_2$)$_3$(3K) | 16 | 7 | 1.1 | 120 | 18 |
| 13 | Ø(PIB-CA)$_3$(5K) | 0 | 0 | Ø(PIB-NEt$_2$)$_3$(3K) | 11 | 8 | 0.6 | 60 | 14 |
| 14 | Ø(PIB-CA)$_3$(5K)/TMP-CA15 | 15 | 47 | Ø(PIB-NEt$_2$)$_3$(3K) | 16 | 5 | 1.1 | 130 | 18 |

*Averages of 3 determinations

Chemical Structure 1: Possible Structure Formed of Ø(PIB-CA)$_3$ plus 3 TMP-NEt$_2$s. Out of the Three Zwitter-Ions Formed One Becomes "Buried" (Unit in Dotted Circle), and Two React with Additional CA Groups Leading to Network

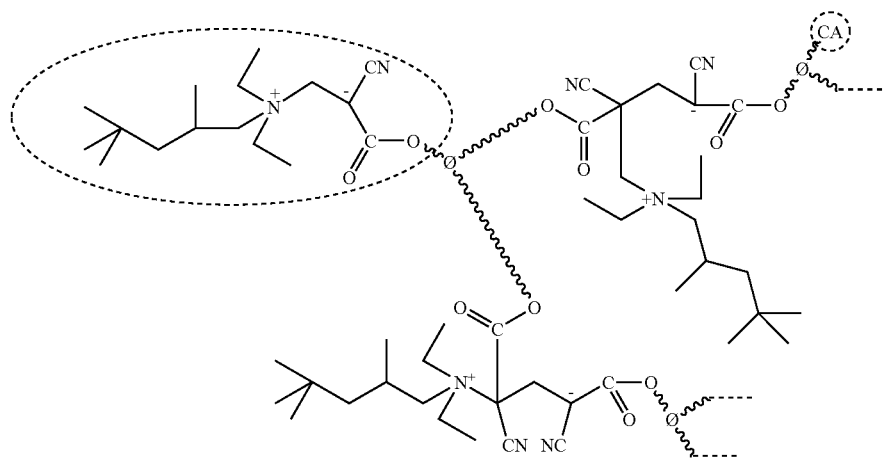

The sketch shows a one possible structure that arises by the reaction involving one Ø(PIB-CA)$_3$ and three TMP-NEt$_2$ molecules of the three zwitter-ions that arise one is lost to further reaction by becoming buried in the PIB matrix, while the other two react with CA groups of other Ø(PIB-CA)$_3$ molecules ("propagation"). In view of the tri-functional nature of the Ø(PIB-CA)$_3$ prepolymer, one such propagation step per Ø(PIB-CA)$_3$ is sufficient to yield networks.

The next group of experiments (Experiments 4 to 6) concerned the preparation of a series of networks by the use of Ø(PIB-CA)$_3$ (i.e., in the absence of TPM-CA) and the polymeric initiator Ø(PIB-NEt$_2$)$_3$. Modest mechanical properties are obtained with [-CA]/[-NEt$_2$] equal to 6 and 11. At [-CA]/[-NEt$_2$] equal to 30 the polymerization is relatively slow and the product is weak most likely due to the low initiator concentration.

Next a group of copolymerization experiments is carried out with Ø(PIB-CA)$_3$ and TMP-CA charges (Experiments 7 to 10). Experiment 8 with 15% TMP-CA and [-CA]/[-NEt$_2$] equal to 16 yields a relatively strong film with good elongation (tensile stress 1.2 MPA, 115% elongation). Increasing the [-CA]/[-NEt$_2$] to 30 results in a small decrease in properties (Experiment 9). Increasing the TMP-CA concentration to 35% (Experiment 10) yields 2.1 MPa tensile stress and 160% elongation, however, at this TMP-CA level bulk charges become heterogeneous (see above).

The rest of the experiments (Experiments 11 to 14) is carried out by using an expressly prepared -NEt$_2$-telechelic three-arm star initiator. However, the properties of the products do not show improvement over that obtained with the linear bifunctional initiator Ø(PIB-NEt$_2$)$_2$ (Experiment 8).

In sum, the parameters for the synthesis of injectible PIB networks have been established (i.e., molecular weights, [-CA]/[-NEt$_2$] ratios) and prototype networks and co-networks of promising mechanical properties are prepared.

Network Reinforcement with Colloidal Silica:

Butyl rubber is reinforced with silica for the production of colorless/white medical stoppers, tubing, etc. In view of this technology a scouting experiment is carried out to explore the possibility of reinforcing Ø(PIB-CA)$_3$ networks by colloidal silica.

Thus, the bulk polymerization of Ø(PIB-CA)$_3$ is initiated by a blend prepared of Ø(PIB-NEt$_2$)$_3$ plus 10% colloidal SiO$_2$. The blend is prepared by dissolving Ø(PIB-NEt$_2$)$_3$ in heptane, adding 10% SiO$_2$, mixing the system, and evaporating the solvent. The blend is used to initiate the bulk polymerization of Ø(PIB-CA)$_3$ under conditions of Experiment 6 of Table 16. The mechanical properties of the product obtained by the double syringe technique do not exhibit promising properties.

Further Embodiments

Various embodiments discussed above are concerned the preparation of novel networks and co-networks for possible medical applications by the polymerization of cyanoacrylate-telechelic three-arm polyisobutylene stars [Ø(PIB-CA)$_3$], and co-polymerizations of Ø(PIB-CA)$_3$/ethyl cyanoacrylate (Et-CA) mixtures. Ø(PIB-CA)$_3$ polymerizations are initiated in the bulk by injecting liquid Ø(PIB-CA)$_3$ into proteinacious tissue (chicken eggs), and the copolymerization of Ø(PIB-CA)$_3$/Et-CA mixtures by strong nucleophiles (e.g., N,N-dimethyl-p-toluidine, DMT) in THF solvent. The co-polymerizations initiated by DMT are much faster and yield superior mechanical properties than those initiated in the bulk by proteinacious tissue. In spite of the high molecular weight of the Ø(PIB-CA)$_3$, typically M$_n$ approximately 3,000 g/mol, and therefore low molar concentration of CA, co-polymerizations initiated by DMT are essentially instantaneous and produce rubbery polymers exhibiting mechanical properties promising for the intended applications (subcutaneous bulking agents, inter-vertebral discs).

Accordingly, it is believed that the essentially instantaneous bulk polymerizations of Ø(PIB-CA)$_3$, and of course co-polymerizations of Ø(PIB-CA)$_3$/Et-CA mixtures can be effected by the use of strongly nucleophilic linear and 3-arm star NEt$_2$-telechelic initiators Ø(PIB-NEt$_2$)$_{2\ or\ 3}$. Because both the Ø(PIB-CA)$_3$ "monomer" and the Ø(PIB-NEt$_2$)$_{2\ or\ 3}$ initiator are predominantly of PIB they are expected to mix readily, and the reaction between the polar -NEt$_2$ and -CA groups in the non-polar PIB continuum, i.e., nucleophilic Michaels attack of -NEt$_2$ on the CA group leading to zwitter-ions, would be facilitated:

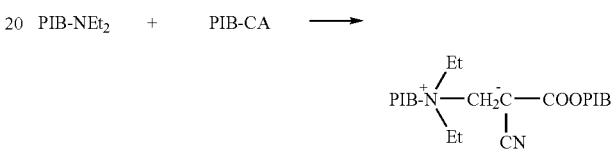

Because the chemical (hydrolytic/oxidative/enzymatic/biological) stability of poly(Et-CA) is limited, and this stability is important for medical applications, in the present research Et-CA in the copolymers is replaced with 2,4,4-trimethylpentane-cyanoacrylate (TMP-CA) which is expected to provide superior chemical resistance:

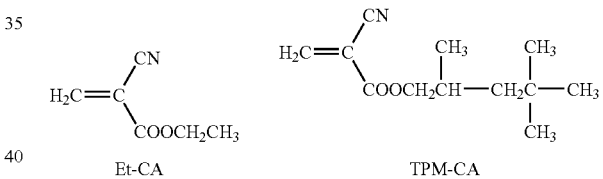

Due to this replacement, it is demonstrated (see below) that the TMP group protects the vulnerable CA group in the copolymer from hydrolytic/oxidative attack. Given this, the present invention encompasses a synthesis route to yield TMP-CA since this molecule is novel.

This portion of the present invention concerns the synthesis and characterization of novel PIB networks and PIB/poly(TMP-CA) co-networks prepared by combining Ø(PIB-CA)$_3$ "monomer" and Ø(PIB-CA)$_3$/TMP-CA "co-monomer" charges, respectively, with strongly nucleophilic Ø(PIB-NEt$_2$)$_{2\ or\ 3}$ "initiators". Among some of the objectives are instantaneous polymerization, and the preparation of rubbery networks and co-networks in the bulk for possible biomedical applications.

Experimental:

Materials:

2,4,4-trimethyl-1-pentene (TMP, 98%), 2,4,4-trimethyl-1-pentanol (TMP-OH, 98%), diethylamine (99.5%), sodium bicarbonate, N,N-dicyclohexyl-carbodiimide (DCC, 1 molar solution in dichloromethane) and 4-dimethylaminopyridine (DMAP) are from Aldrich, and are used as received, dichloromethane (DCM), N,N-dimethylformamide (DMF), p-xylene, hexanes (Aldrich) are distilled over CaH$_2$ prior to use.

The controls for oxidative/acid stability tests are a PDMS-containing polyurethane from AorTech Biomaterials Pty Ltd Australia, and a PDMS network made by crosslinking vinyl di-telechelic PDMS of $M_n$ equal to 5,000 g/mole with polymethylhydrosiloxane obtained from Gelest.

Instruments and Procedures:

Details of NMR and FTIR spectroscopies, GPC, equilibrium swelling, DMTA and Instron measurements are described earlier. Hardness (Microshore) of network and co-network films of 0.5 mm thickness is determined by using a Micro-O-Ring Hardness Tester. Averages of three determinations are reported. TGA is carried out by a TGA Q 500 instrument (TA Instruments) from 30 to 600° C. with an aluminum pan with a heating rate of 5° C./min.

A DSC-TA (DSC Q 200, TA Instruments) working under a nitrogen atmosphere is used. The instrument is calibrated with indium for each set of experiments. Approximately 10 mg samples are placed in aluminum pans sealed by a quick press, and heated at a scanning rate of 10° C./min. The glass-transition temperature ($T_g$) is obtained from the second heating scan.

Network and co-network samples (5×5×0.01-0.04 cm) are dried in vacuum for 48 hours at 60° C., weighed, placed in approximately 100 mL distilled THF and gently stirred for 24 hours. Subsequently, the samples are removed from the THF, dried in vacuum for 24 hours at room temperature and weighed.

The weight percent of the extractables (E) is calculated by:

$$E = 100(m_{dry} - m_{ex})/m_{dry}$$

where $m_{dry}$ and $m_{ex}$ are the masses of the virgin and extracted samples, respectively. Averages of three determinations are reported.

The oxidative/acid stability of networks and co-networks is investigated by exposure to concentrated nitric acid. Thus dumbbells (2.5 cm long, 0.35 cm width at the neck) of solution cast films are immersed in boiling concentrated nitric acid for 1 hour. After washing with water and vacuum drying, THF extractables, stress-strain properties and hardness are determined.

Syntheses

Synthesis of Cyanoacrylate Terminated Tri-Arm Star PIB Ø(PIB-CA)$_3$

The synthesis of PIB (Ø(PIB-CA)$_3$) of $M_n$ equal to 3,000 and 5,000 g/mole is described.

Synthesis of 1-Cyanoacryl-2,4,4-Trimethylpentane (TMP-CA)

Scheme 1 outlines the strategy for the synthesis of TMP-CA. Thus TMP-OH is esterified with (pre-made) anthracene-protected cyanoacrylic acid (pCA) to afford protected 2,2,4-trimethylpent-1-cyanoacrylate (pTMP-CA), and the latter is de-protected with maleic anhydride.

To 25 grams (0.20 mole) TMP-OH and 71 grams (0.26 mole) anthracene-protected cyanoacrylic acid (pCA) dissolved in a mixture of 200 mL dry dichloromethane, are added 260 mL (0.26 moles) DCC and 0.01 grams DMAP, and the mixture is stirred for 16 hours at 30° C. The charge is filtered, the solvents evaporated, and the crude product dissolved in hexanes to separate the unreacted pCA. Finally the hexanes solution of pTMP-CA is purified by passing the solution through a 35 cm silica and a neutral alumina column. Rotary evaporation yielded 61 grams (80%) of the protected ester.

The pTMP-CA is de-protected with excess maleic anhydride to produce TMP-CA as follows: 30 grams (0.077 moles) pTMP-CA, 22 grams (0.23 moles) maleic anhydride, 0.1 grams phosphorous pentoxide and 0.02 grams hydroquinone are dissolved in about 150 mL of anhydrous xylene. Into the mixture is bubbled a stream of $SO_2$ inhibitor for about 5 minutes, and the mixture is heated with stirring for 15 hours at reflux (146° C.). The mixture is cooled to room temperature, the xylene is removed by a rotavap at 60° C., and the crude TMP-CA is dissolved in dry hexanes. The unreacted pCA, the maleic anhydride/anthracene adduct, and the maleic anhydride is precipitated, and the mixture is filtered under a nitrogen atmosphere. The hexanes are evaporated by rotavap to give TMP-CA, a slightly yellow liquid. The residual xylene is removed by repeated addition of hexanes and the TMP-CA is concentrated by a rotavap at 60° C. The yield is 10.4 grams (63%). $^1$H NMR (300 Mz, $CDCl_3$): δ (ppm) δ=4.1 to 4.4 (q, 2H)—O—$CH_2$—, δ=2 (1H)—O—$CH_2CH$ ($CH_3$), δ=1.1 (s, 3H)—O—$CH_2$—CH($CH_3$), δ=1 (9H)—O—$CH_2$—CH($CH_3$)$CH_2C(CH_3)$ and δ=6.9 and 7.1 —CH=C(CN).

Synthesis of poly(1-cyanoacryl-2,4,4-trimethylpentane) [poly(TMP-CA)]

Poly(TMP-CA) is synthesized by adding 0.01 grams N,N-diethylamine-2,4,4-trimethylpentane (TMP-NEt$_2$) to 2 grams TMP-CA dissolved in 8 mL dry toluene, and stirring the mixture for 1 hour at room temperature. The solvent is evaporated and the product dried under vacuum for 2 days. The yield is 1.95 grams (97.5%).

Synthesis of 1-N,N-Diethylamine-2,4,4-Trimethylpentane (TMP-NEt$_2$), N,N-Diethylamine Terminated Di-Arm Linear PIB [Ø(PIB-NEt$_3$)$_2$] and Tri-Arm Star PIB [Ø(PIB-NEt$_3$)$_3$]

A representative synthesis of Ø(PIB-NEt$_3$)$_3$ is as follows. First, allyl-telechelic PIB of $M_n$ equal to 3,000 g/mole is converted to Br-telechelic 3-arm star PIB [Ø(PIB-Br)$_3$] by the procedure described above. Next, a 500 mL three-neck flask equipped with a magnetic stirrer and condenser is charged with 200 mL dry THF, 40 mL DMF, 15 grams (3,000 g/mol; 0.005 mole) Ø(PIB-Br)$_3$, 12 grams (0.16 mole) diethylamine, and 0.3 grams NaHCO$_3$, and the charge is refluxed for approximately 8 hours. The solvents are evaporated by a rotavap, 100 mL hexanes are added, the system is washed 3 times with 100 mL water, dried over MgSO$_4$, filtered, and the solvent is evaporated by a rotavap at 50° C. The product, Ø(PIB-NEt$_2$)$_3$, is a clear, colorless, transparent, viscous liquid. $^1$H NMR (300 Mz, $CDCl_3$): δ (ppm) δ=2.5 (q, 4H) —N—$CH_2$—$CH_3$, (s, 3H) δ=1.6 —N—$CH_2$—$CH_3$, δ=0.8 to 1.5 PIB backbone and δ=7.1 to 7.3 aromatic proton (initiator core).

TMP-NEt$_2$ is synthesized starting from 2,4,4-trimethyl-1-pentene (TMP). First TMP is converted to 2,4,4-trimethyl-1-bromopentane (TMP-Br) using the procedure used for the conversion of allyl-telechelic PIB to Br-telechelic PIB. TMP-Br is subsequently converted to TMP-NEt$_2$ by reacting TMP-Br with excess diethyl amine as described above.

Synthesis of Networks and Co-Networks in Bulk and in Solution

Synthesis in the Bulk (Reaction Injection Molding (RIM))

Figure 26:
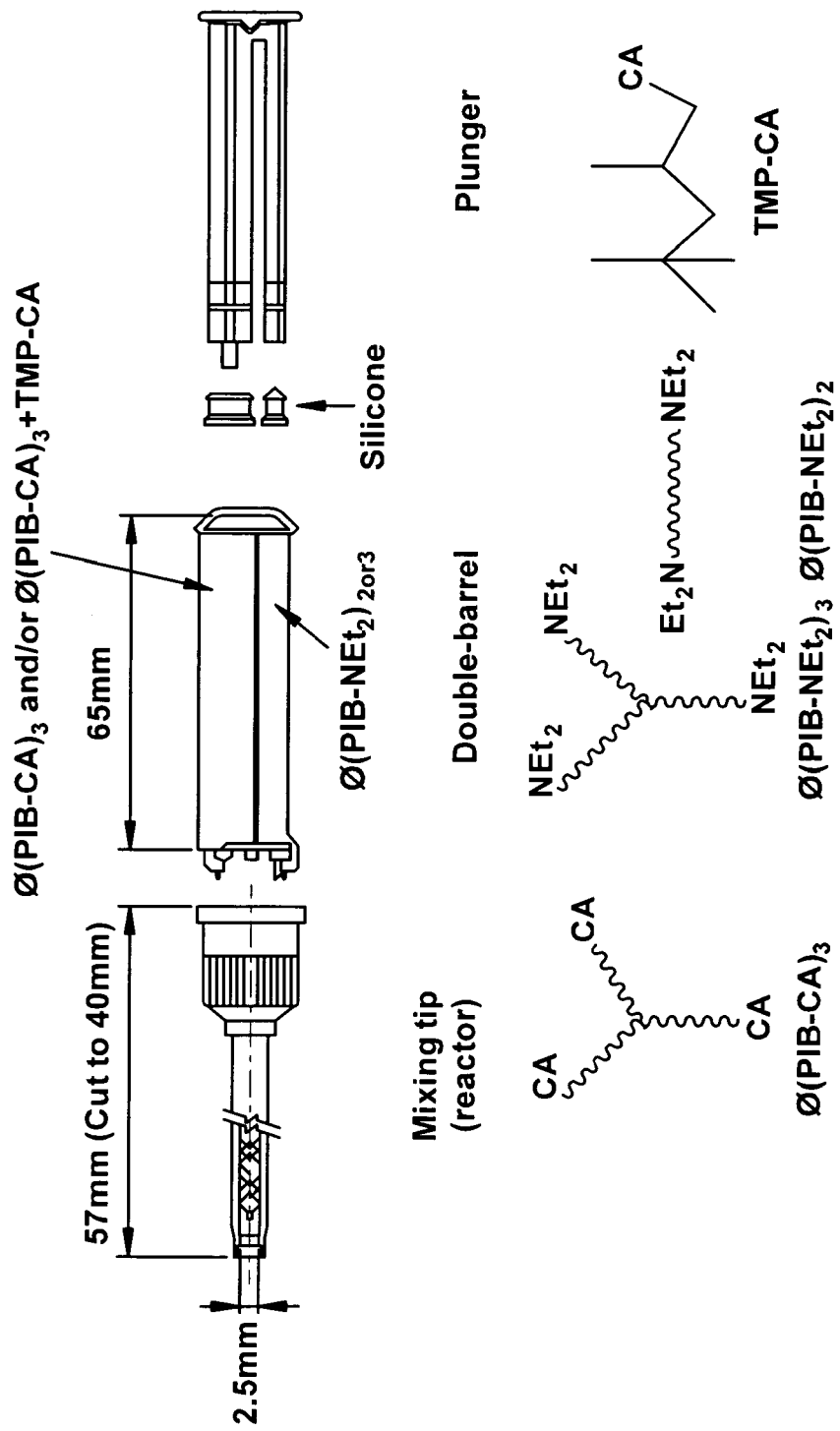
FIG. 26 is an illustration of another embodiment of a dual syringe system used for the bulk polymerization process of the present invention.

FIG. 26 is a sketch of the double-syringe and its components used for various bulk polymerization and copolymerization experiments. Double-syringes of barrel ratios 4:1 (2.5 mL) and 10:1 (11 mL) (Medmix systems AG, Switzerland) with a 58 mm mixer (DN 2.5×16×4:1, brown, med) and Lure-Tip are used. The length of the mixing tip is cut to approximately 40 mm to facilitate injection.

A representative bulk polymerization is carried out as follows: 0.45 grams Ø(PIB-NEt$_2$)$_2$ of M$_n$ equal to 5,000 g/mole (0.00018 moles) is poured into the small barrel of a double-syringe (1:4). The larger barrel of the syringe is purged with argon and 2 grams Ø(PIB-CA)$_3$ of M$_n$ equal to 3,000 g/mole (0.002 moles) is poured into it with the help of a hydrophobized glass rod. This system yields [-CA]/[-NEt$_2$] equal to 11. The Ø(PIB-CA)$_3$ and Ø(PIB-NEt$_2$)$_2$ level is adjusted by inserting the common plunger. The mixing tip is attached and the reaction partners are manually rapidly pushed into it. The product that emerges from the tip is a bolus of crosslinked PIB rubber.

Synthesis in Solution

Ø(PIB-CA)$_3$ networks and Ø(PIB-CA)$_3$/TMP-CA co-networks are prepared in solution by the use of TMP-NEt$_2$, Ø(PIB-NEt$_2$)$_3$ and Ø(PIB-NEt$_2$)$_2$ initiators. A representative synthesis of a network and/or co-network is as follows: One gram Ø(PIB-CA)$_3$ (0.001 moles) or a mixture of 0.85 grams Ø(PIB-CA)$_3$ (0.00085 moles) and 0.15 grams (0.0073 moles) TMP-CA is dissolved in 5 mL toluene and 0.25 grams Ø(PIB-NEt$_2$)$_2$ (0.0001 moles) dissolved in 1 mL toluene is added. The solution is homogenized by shaking and immediately poured into a 5×5 cm square Teflon mold, covered with alumina foil, and the solvent is evaporated in a fume hood for 2 days. Finally, the film (0.3 mm thick) is vacuum dried at 100° C. to constant weight. Sol fractions and swelling are determined, and Instron, DSC, TGA and DMTA characterizations are carried out.

Results and Discussion:

Some main objectives of the present invention are the synthesis, characterization and evaluation for possible biomedical applications of PIB networks and PIB/poly(TMP-CA) co-networks formed by instantaneous bulk polymerization and copolymerization, respectively. Experiments using conventional solution polymerizations are also carried out to obtain cast films for mechanical property evaluation.

Preliminary experimentation shows that instantaneous polymerizations could be obtained by combining syringible Ø(PIB-CA)$_3$ and Ø(PIB-CA)$_3$+TMP-CA charges with strongly nucleophilic non-terminating tert-amine initiators, i.e., Ø(PIB-NEt$_2$)$_2$ $_{or\ 3}$ by means of a double-syringe. The fundamental reaction between the ingredients is a Michael addition of -NEt$_2$ and -CA groups, and leads to zwitter-ions between two PIB moieties:

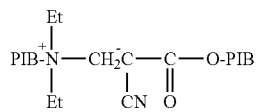

The molecular weight (viscosity) limit for convenient manual siringibility of PIB-based liquids through 18 gauge hypodermic needles is determined to be in the about 3,000 to about 5,000 g/mole range. However, the present invention is not limited to just manual siringibility embodiments. As such, higher molecular weights are within the scope of the present invention.

The reactants are combined in the bulk by means a double-syringe. The two (twin) barrels of the double-syringe are filled with the monomer(s) and initiator, and are propelled simultaneously by a common plunger into the mixing tip (in fact the reactor) where the bulk polymerization occurs. This technique is essentially reaction injection molding (RIM), a method used for the manufacture of polyurethanes.

Previous studies show that CA polymerizations initiated in the bulk by proteinacious matter (i.e., chicken eggs) are not instantaneous and yield relatively weak materials. To increase the rates and to obtain stronger materials highly nucleophilic tert-amines are utilized herein to induce instantaneous non-terminating polymerization of cyanoacrylates. Preliminary experiments show that the tert-amine-telechelic PIBs, Ø(PIB-NEt$_2$)$_2$ $_{or\ 3}$ of M$_n$, equal 3,000 to 5,000 g/mole, are completely miscible with and instantaneously polymerized Ø(PIB-CA)$_3$ and Ø(PIB-CA)$_3$/TMP-CA15 charges of the same molecular weight in the bulk.

In some of the embodiments above, Et-CA as the co-monomer to improve the mechanical properties of Ø(PIB-CA)$_3$/Et-CA co-networks. In the following embodiments Et-CA is replaced with TMP-CA because: (1) in contrast to Et-CA which is immiscible with Ø(PIB-CA)$_3$ in the bulk TMP-CA is miscible (at least 15%) with Ø(PIB-CA)$_3$, and Ø(PIB-CA)$_3$/TMP-CA15 charges yield homogeneous clear syringible solutions; (2) on account of the reasonably high T$_g$ of poly(TMP-CA) (35° C., see Table 21), poly(TMP-CA) segments are expected to strengthen/stiffen/harden the copolymer; and (3) the toxicity of CA-polymers decreases and their biocompatibility increases with increasing molecular weight and branching, the bio-acceptability of TMP-CA units is expected to be superior to those of Et-CA units.

Instantaneous Bulk Polymerization of Ø(PIB-CA)$_3$ and Ø(PIB-CA)$_3$+TMP-CA Mixtures by Ø(PIB-NEt$_2$)$_2$ $_{or\ 3}$ Initiators Using the Double-Syringe:

Instantaneous reactions between Ø(PIB-CA)$_3$ plus Ø(PIB-NEt$_2$)$_2$ $_{or\ 3}$, and Ø(PIB-CA)$_3$/TMP-CA plus Ø(PIB-NEt$_2$)$_2$ $_{or\ 3}$ are effected in the bulk by the use of double-syringes. Ø(PIB-CA)$_3$ or Ø(PIB-CA)$_3$/TMP-CA charges are placed into the larger barrel of double-syringes, the Ø(PIB-NEt$_2$)$_2$ $_{or\ 3}$ initiator is placed in the smaller barrel, and reactions are initiated by propelling both charges into the mixing chamber. Reaction (i.e., zwitter-ion formation, followed by polymerization and copolymerization of the CA groups) is essentially instantaneous and the products emerged as strips at the end of the mixing tip. Considerable preliminary experimentation is carried out to develop suitable conditions (reagent viscosities, ratios of ingredients, speed and force of injection, etc.) to obtain instantaneous polymerizations and satisfactory products by this uncommon technique.

Because the reactants undergo rapid crosslinking upon injection in the mixing chamber, and the networks that exit may undergo stress fracture during extrusion, quantitative product characterization options are limited. The extent of extractables (sol fractions) and extent of swelling is determined as noted herein, and a detailed visual/manual examinations of the co-networks is preformed.

Table 17 summarizes the results of bulk polymerizations. Depending on the type of the double-syringe, the data are subdivided to experiments carried out with a 4:1 and a 10:1 syringe.

The first group of four experiments in Table 17 shows the effect of increasing amounts of TMP-CA on the products. In these experiments Ø(PIB-CA)$_3$/TPM-CA mixtures are placed in the larger barrel of the syringe and are co-injected with the Ø(PIB-NEt$_2$)$_3$ placed in the smaller barrel.

TABLE 17

Summary of Bulk Polymerizations of Ø(PIB-CA)$_3$ and
Co-Polymerizations of Ø(PIB-CA)/TMP-CA Mixtures by the Use of Double Syringes

| No. | Network/Co-Network | TMP-CA wt % | TMP-CA mole % | Initiator | [-CA]/[-NEt$_2$] | Swelling (%) Hexanes | Swelling (%) Acetone | Extractables* (%) | Rate of pzn (visual obs.) | Mech. Props. (manual) |
|---|---|---|---|---|---|---|---|---|---|---|
| | | | | | Barrel ratio 4:1 | | | | | |
| 1 | Ø(PIB-CA)$_3$(3K) | — | — | Ø(PIB-NEt$_2$)$_3$(3K) | 4.5 | 72 | 5 | 13 | Immediate network formation | Weak, elastic, pulls apart easily, cheesy |
| 2 | Ø(PIB-CA)$_3$(3K)/TMP-CA15 | 15 | 47 | Ø(PIB-NEt$_2$)$_3$(3K) | 6.2 | 70 | 9.5 | 13 | Immediate network formation | Soft rubbery, cheesy |
| 3 | Ø(PIB-CA)$_3$(3K)/TMP-CA20 | 20 | 55 | Ø(PIB-NEt$_2$)$_3$(3K) | 9 | — | — | 13 | Immediate network formation | Soft rubbery, smell of TMP-CA |
| 4 | Ø(PIB-CA)$_3$(3K)/TMP-CA35 | 35 | 73 | Ø(PIB-NEt$_2$)$_3$(3K) | 12 | 71 | 30 | 16 | Immediate network formation | Soft rubbery, strong smell of TMP-CA |
| 5 | Ø(PIB-CA)$_3$(3K) | — | — | Ø(PIB-NEt$_2$)$_2$(5K) | 11 | 74 | 6 | 11 | Immediate network formation | Soft rubbery |
| 6 | Ø(PIB-CA)$_3$(3K)/TMP-CA15 | 15 | 47 | Ø(PIB-NEt$_2$)$_2$(5K) | 16 | 72 | 11 | 11 | Immediate network formation | Strong, odorless, colorless elastic |
| 7 | Ø(PIB-CA)$_3$(5K) | — | — | Ø(PIB-NEt$_2$)$_2$(5K) | 4 | — | — | — | Immediate network formation | Weak, elastic, pulls apart easily, |
| 8 | Ø(PIB-CA)$_3$(5K)/TMP-CA15 | 15 | 47 | Ø(PIB-NEt$_2$)$_2$(5K) | 13 | — | — | — | Immediate network formation | Soft rubbery |
| 9 | Ø(PIB-CA)$_3$(3k) | — | — | Ø(PIB-NEt$_2$)$_3$(3K) Injected on fresh chicken egg | 4.5 | — | — | 9 | Immediate network formation | Weak, elastic, pulls apart easily |
| | | | | | Barrel ratio 10:1 | | | | | |
| 10 | Ø(PIB-CA)$_3$(3k)/TMP-CA15 | 15 | 47 | Ø(PIB-NEt$_2$)$_{2(5K)}$ Injected in fresh chicken egg | 16 | — | — | 9 | Immediate network formation | Strong, colorless elastic |
| 11 | Ø(PIB-CA)$_3$(3K) | — | — | Ø(PIB-NEt$_2$)$_2$(5K) | 27 | — | — | — | Very slow | Remains sticky after 3 days |
| 12 | Ø(PIB-CA)$_3$(3K)/TMP-CA15 | 15 | 47 | Ø(PIB-NEt$_2$)$_3$(5K) | 40 | — | — | — | slow | Remains sticky after 3 days |

*Average of 3 determinations

TMP-CA is a clear liquid, and up to 15% TMP-CA mixed with Ø(PIB-CA)$_3$ of M$_n$ equal to 3,000 to 5,000 g/mole gives homogenous clear solutions. In the presence of more than 15% TMP-CA, the system becomes hazy indicating phase separation. Warming mixtures to approximately 50° C. containing 20 to 35% TMP-CA produces homogeneous clear solutions. However, phase separation returns upon cooling to room temperature. Above 35% TMP-CA, the system remains heterogeneous even after heating to approximately 50° C.

As suggested by the relatively low levels of extractables (13%), crosslinking is quite efficient in Experiments 1 to 3. The best result in this series of experiments seems to be obtained with [-CA]/[-NEt$_2$] equal to 6.2 (Experiment 2).

The characteristic odor of TMP-CA is noticeable in the product of Experiment 3, and is quite strong in that of Experiment 4. Evidently, TMP-CA is only partially consumed in these experiments. The amount of extractables is largest (16%) in Experiment 4, most likely due to the presence of unconverted TPM-CA. After storage for 5 to 6 days at room temperature the odor of TMP-CA diminishes indicating slow homo- and/or copolymerization of TMP-CA.

The swelling data collected in Experiments 1, 2, and 4 are revealing. Swelling of all the products in hexanes is consistently 70% to 72% due to the predominating continuous PIB phase (PIB is soluble in hexanes but insoluble in acetone, while poly(TMP-CA) is soluble both in hexanes and acetone). In contrast, swelling in acetone increases with increasing poly(TMP-CA) content which is in line with the presence of increasing poly(TMP-CA) moieties. Surprisingly, all the networks, even those prepared in the absence of TMP-CA, imbibed acetone suggesting edge-to-edge cyanoacrylate phase continuity, i.e., continuous channels of CA groups in the continuous PIB matrix.

In Experiments 5 and 6 the [-CA]/[-NEt$_2$] ratio is increased to 11 and 16, respectively, by increasing the molecular weight of the initiator. Increasing [-CA]/[-NEt$_2$] is expected to increase product molecular weights, i.e., resulting in better mechanical properties. Indeed, extractables decreased to 11%, and the properties of the products definitively improved as judged by visual/manual examination. The product obtained in Experiment 6 exhibited the best mechanical properties obtained in the 12 cases summarized in Table 17.

In Experiments 7 and 8 we increased the molecular weight of the Ø(PIB-CA)$_3$ to 5,000 g/mole, however, the mechanical properties noticeably diminished. The higher viscosity of the system reduced the rate of the reaction.

Experiments 9 and 10 are carried out by co-injecting, respectively, Ø(PIB-CA)$_3$ plus Ø(PIB-NEt$_2$)$_3$, and Ø(PIB-CA)$_3$/TMP-CA15 plus Ø(PIB-NEt$_2$)$_3$ onto chicken eggs. Earlier experiments showed that in the absence of Ø(PIB-NEt$_2$)$_3$, Ø(PIB-CA)$_3$ or Ø(PIB-CA)$_3$/TMP-CA15 charges when injected into eggs undergo relatively slow polymerization reaction and yield weak products. In Experiments 9 and 10 polymerizations to colorless masses are instantaneous, the extent of extractables decreases, and the mechanical properties of the products are judged promising for the intended applications (see above). Evidently, the moisture in the eggs has only little effect on the polymerizations in the presence of the strong nucleophile Ø(PIB-NEt$_2$)$_3$.

In the last two Experiments, 11 and 12, the [-CA]/[-NEt$_2$] ratio is increased to 27 and 40, respectively. Under these conditions the polymerization reactions are slow and unacceptable sticky products are obtained most likely due to the low initiator concentration. After 5 to 6 days storage at room temperature the products become non-sticky and stronger due to slow polymerization of unreacted Ø(PIB-CA)$_3$ and/or Ø(PIB-CA)$_3$/TMP-CA.

Preparation of Solution Cast Films of Networks and Co-Networks for Mechanical Property Evaluation:

Because polymerizations in bulk by the use of double-syringes provides largely subjective/qualitative observations and objective/quantitative property information is lacking, conventional solution experiments are carried out to obtain films for mechanical property evaluation. These films are cast from solutions whose relative concentrations are similar to those used in double-syringe bulk experiments.

Table 18 summarizes experimental conditions, extractables, and mechanical properties of films cast under conditions approximating those used in bulk experiments. The amounts of extractables obtained in these experiments (5 to 9.5%) are substantially lower than those obtained in bulk, and indicate high degrees of crosslinking.

TABLE 18

Properties of solution cast Films of Networks and Co-Networks

| No. | Network/Co-Network | TMP-CA Wt % | TMP-CA Mole % | Initiator | [-CN]/[-NEt$_2$] | Extractables* (%) | Stress (MPa) | Strain (%) | Hardness (Micro shore) |
|---|---|---|---|---|---|---|---|---|---|
| 1 | Ø(PIB-CA)$_3$(3K) | — | — | TMP-NEt$_2$ | 12 | 7 | 0.7 | 45 | 18 |
| 2 | Ø(PIB-CA)$_3$(3K)/TMP-CA15 | 15 | 47 | TMP-NEt$_2$ | 16 | 5 | 1.4 | 125 | 25 |
| 3 | Ø(PIB-CA)$_3$(3K)/TMP-CA35 | 35 | 73 | TMP-NEt$_2$ | 30 | 5 | 2.6 | 180 | 32 |
| 4 | Ø(PIB-CA)$_3$(3K) | — | — | Ø(PIB-NEt$_2$)$_2$(5K) | 6 | 9 | 0.3 | 50 | 12 |
| 5 | Ø(PIB-CA)$_3$(3K) | — | — | Ø(PIB-NEt$_2$)$_2$(5K) | 11 | 7 | 0.6 | 55 | 15 |
| 6 | Ø(PIB-CA)$_3$(3K) | — | — | Ø(PIB-NEt$_2$)$_2$(5K) | 30 | — | — | — | Sticky, weak network |
| 7 | Ø(PIB-CA)$_3$(3K)/TMP-CA15 | 15 | 47 | Ø(PIB-NEt$_2$)$_2$(5K) | 8 | 6 | 0.7 | 90 | 16 |
| 8 | Ø(PIB-CA)$_3$(3K)/TMP-CA15 | 15 | 47 | Ø(PIB-NEt$_2$)$_2$(5K) | 16 | 8 | 1.2 | 115 | 20 |
| 9 | Ø(PIB-CA)$_3$(3K)/TMP-CA15 | 15 | 47 | Ø(PIB-NEt$_2$)$_2$(5K) | 30 | 7 | 1.0 | 102 | 19 |
| 10 | Ø(PIB-CA)$_3$(3K)/TMP-CA35 | 35 | 73 | Ø(PIB-NEt$_2$)$_2$(5K) | 30 | 5 | 2.1 | 160 | 28 |

TABLE 18-continued

Properties of solution cast Films of Networks and Co-Networks

| | | TMP-CA | | | | | Mechanical Properties* | |
|---|---|---|---|---|---|---|---|---|
| No. | Network/Co-Network | Wt % | Mole % | Initiator | [-CN]/[-NEt₂] | Extractables* (%) | Stress (MPa) | Strain (%) | Hardness (Micro shore) |
| 11 | Ø(PIB-CA)₃(3K) | — | — | Ø(PIB-NEt₂)₃(3K) | 11 | 9.5 | 0.5 | 57 | 14 |
| 12 | Ø(PIB-CA)₃(3K)/TMP-CA15 | 15 | 47 | Ø(PIB-NEt₂)₃(3K) | 16 | 7 | 1.1 | 120 | 18 |
| 13 | Ø(PIB-CA)₃(5K) | — | — | Ø(PIB-NEt₂)₃(3K) | 11 | 8 | 0.6 | 60 | 14 |
| 14 | Ø(PIB-CA)₃(5K)/TMP-CA15 | 15 | 47 | Ø(PIB-NEt₂)₃(3K) | 16 | 5 | 1.1 | 130 | 18 |

*Averages of 3 determinations.

The first group of three experiments is carried out with the small molecule TMP-NEt₂ initiator, expressly prepared for these investigations. The mechanical properties of the films are promising and increased by increasing the [-CA]/[-NEt₂] ratio and increasing the TMP-CA concentration in the 12 to 30 range. Because in these experiments the initiator (TMP-NEt₂) is mono-functional, the low extractables (5 to 7%) indicate "polymerization" of CA groups and a high degree of crosslinking. Chemical Structure 2 below shows a possible structure that may arise from one Ø(PIB-CA)₃ and three TMP-NEt₂ molecules. Of the three zwitter-ions that arise one may be lost to further reaction by becoming buried in the PIB matrix, while the other two react with CA groups of other Ø(PIB-CA)₃ molecules ("propagation"). In view of the tri-functional nature of Ø(PIB-CA)₃ a single propagation step per Ø(PIB-CA)₃ is sufficient to yield networks.

Next a group of co-polymerizations is carried out (Experiments 7 to 10). Experiment 8 with 15% TMP-CA and [-CA]/[-NEt₂] equal to 16 yields a relatively strong film with good elongation (tensile stress 1.2 MPa, 115% elongation). Increasing the [-CA]/[-NEt₂] to 30 results in a small decrease in properties. By increasing the TMP-CA concentration to 35% the results are 2.1 MPa tensile stress and 160% elongation. However, at this TMP-CA level, the charge in the bulk becomes heterogeneous (see above).

The products obtained with Ø(PIB-NEt₂)₃ (Experiments 11 to 14) do not show property improvement over that obtained with Ø(PIB-NEt₂)₂ (in Experiment 8).

Oxidative/Acid Stability of a Ø(PIB-CA)₃ Network and Ø(PIB-CA)₃/TMP-CA Co-Networks:

The oxidative/acid stability of networks and co-networks obtained by crosslinking with TMP-NEt₂ is investigated by exposure to concentrated nitric acid. Samples are immersed Chemical Structure 2

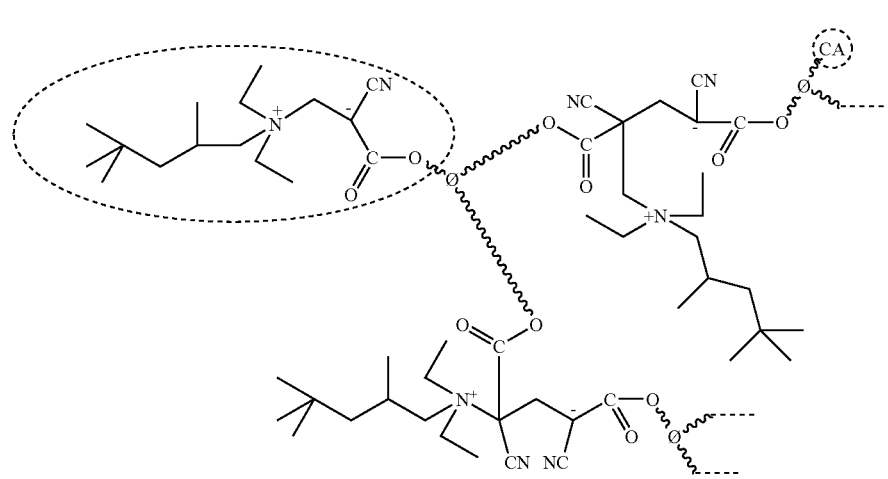

The next group of experiments (Experiments 4 to 6) are concerned with the preparation of networks by the use of Ø(PIB-CA)₃ (i.e., in the absence of TPM-CA) and the initiator Ø(PIB-NEt₂)₃. Modest mechanical properties are obtained at [-CA]/[-NEt₂] equal to 6 and 11; at [-CA]/[-NEt₂] equal to 30 the polymerization is relatively slow and the product is weak and sticky most likely due to low initiator concentration.

in boiling concentrated nitric acid for 1 hour, and the properties (THF extractables, stress-strain and hardness) before and after HNO₃ exposure are determined. Table 19 shows this data. The controls (a commercially available PDMS-containing polyurethane, developed for heightened oxidative stability, and a sample of crosslinked PDMS) disintegrate and yield oily droplets after less than 15 minutes in contact with the acid at room temperature.

TABLE 19

Oxidative/acid Degradation of a Representative Network
and Co-Networks in Terms of Extractables and Mechanical Properties
(After stirring in boiling conc. nitric acid for 1 h)

| Network | TMP-CA Wt % | Mole % | Extractables (THF) (%) | Stress (MPa) Before Ox. | Stress (MPa) After Ox. | Strain (%) Before Ox. | Strain (%) After Ox. | Hardness (Microshore) Before Ox. | Hardness (Microshore) After Ox. |
|---|---|---|---|---|---|---|---|---|---|
| Ø(PIB-CA)$_3$ | — | — | 7 | 11 | 0.7 | 0.6 | 45 | 60 | 18 | 12 |
| Ø(PIB-CA)$_3$/TMP-CA15 | 15 | 47 | 5 | 12 | 1.4 | 0.9 | 125 | 170 | 25 | 16 |
| Ø(PIB-CA)$_3$/TMP-CA35 | 35 | 73 | 5 | 14 | 2.6 | 2.0 | 180 | 250 | 32 | 21 |
| Controls: PDMS-polyurethane, crosslinked PDMS | Totally disintegrated (dissolved) in less than 15 minutes at room temperature (r.t., or RT); only oily droplets remain | | | | | | | | |

The mechanical properties (stresses, elongation, hardness) of the PIB-based networks suggest a small deficit after HNO$_3$ exposure. The small increase of extractables after contact with HNO$_3$ also suggests a small degree of degradation.

Figure 27:
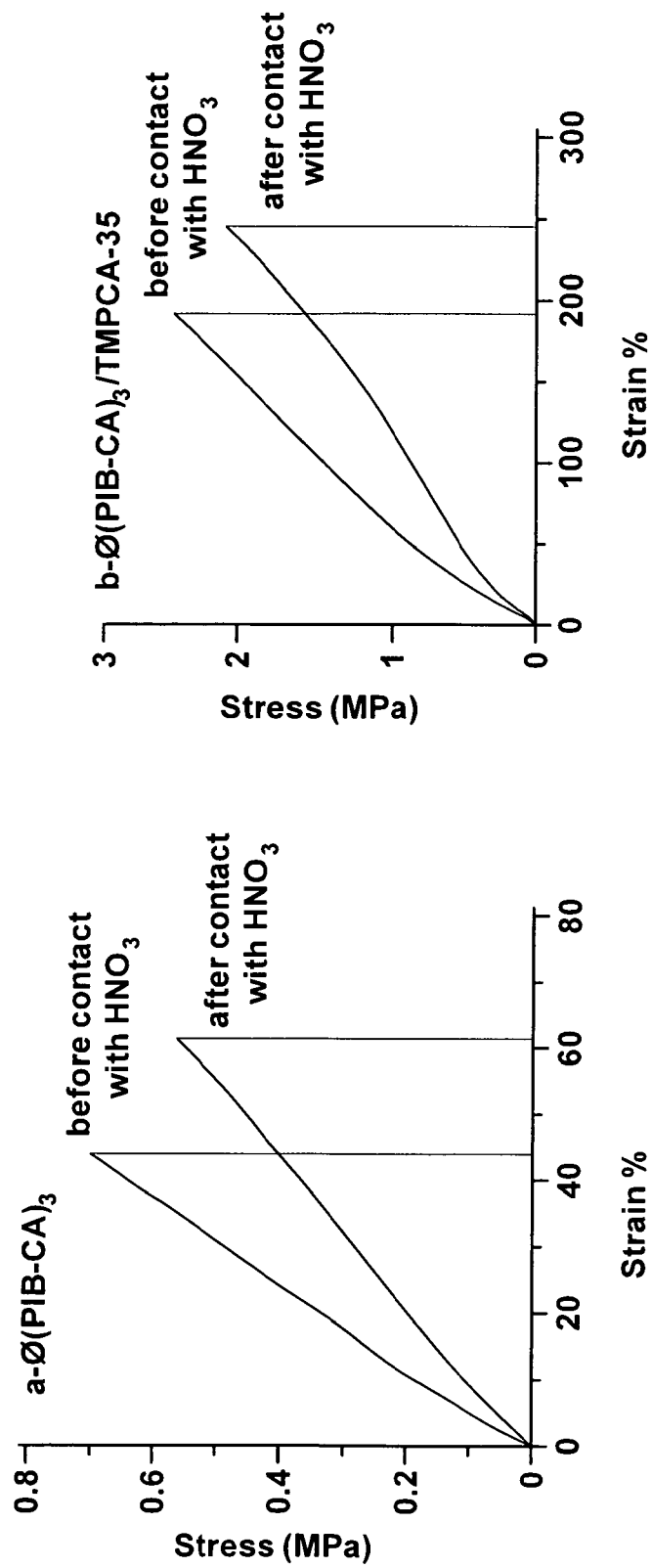
FIG. 27 are stress versus strain curves for various embodiments of the present invention.

The stress-strain traces of a representative network and co-network (Ø(PIB-CA)$_3$ and Ø(PIB-CA)$_3$/TMP-CA35) obtained before and after oxidation also indicate a small deficit in mechanical properties (see FIG. 27).

The outstanding oxidative-acid resistance of Ø(PIB-CA)$_3$/TMP-CA co-networks is also demonstrated by IR spectroscopy. Thus a Ø(PIB-CA)$_3$/TMP-CA30 co-network is exposed to boiling concentrated nitric acid for 1 hour, and the —CN absorption is examined before and after acid contact. The —CN group readily hydrolyzes to —COOH by acids. As shown by the spectra in FIG. 25, the —CN absorption did not change after HNO$_3$ exposure, indicating the protection of —CN groups by PIB moieties.

Additional Characterizations of Cast Films:

Table 20 summarizes equilibrium swelling of a network and three co-networks in hexanes, tetrahydrofuran, and acetone. PIB is soluble in both hexanes and THF but is insoluble in acetone, while poly(TMP-CA) is insoluble in hexanes but soluble in both THF and acetone. Overall, all the co-networks swell in the three solvents suggesting the existence of percolating phases (i.e., co-networks). Specifically, and expectedly, swelling decreases in hexanes while it increases in acetone with increasing TMP-CA content. Remarkably, even the homo-network (i.e., the network prepared in the absence of TMP-CA) swells in acetone indicating percolating (co-continuous) CA and PIB phases (see also above). Co-continuity becomes increasingly pronounced with increasing TMP-CA in the co-networks. Interestingly, swelling in hexanes is lower than that in THF although hexanes is a better solvent for PIB than THF. While not wishing to be bound to any one theory, most likely, the —O—CO—C(CN)—CH$_2$—, moiety reduces the hydrophobicity of the construct.

TABLE 20

Swelling of a Ø(PIB-CA)$_3$ Network and
Three Ø(PIB-CA)$_3$/TMP-CA Co-Networks

| Network | TMP-CA Wt % | TMP-CA Mole % | Swelling (%) Hexanes | Swelling (%) THF | Swelling (%) Acetone |
|---|---|---|---|---|---|
| Ø(PIB-CA)$_3$ | — | — | 79 | 126 | 8 |
| Ø(PIB-CA)$_3$/TMP-CA7 | 7 | 33 | 77 | 134 | 12 |
| Ø(PIB-CA)$_3$/TMP-CA15 | 15 | 47 | 72 | 153 | 18 |
| Ø(PIB-CA)$_3$/TMP35 | 35 | 73 | 71 | 196 | 35 |

FIG. 23 compares the thermal stabilities of poly(TMP-CA), and a representative Ø(PIB-CA)$_3$ network, and a Ø(PIB-CA)$_3$/TMP-CA42 co-network. Evidently, the thermal stability profile of the homo-network is far superior to that of poly(TMP-CA). The thermal stability of the Ø(PIB-CA)$_3$/TMP-CA42 co-network is between that of the poly(TMP-CA) and the homo-network.

Figure 28:
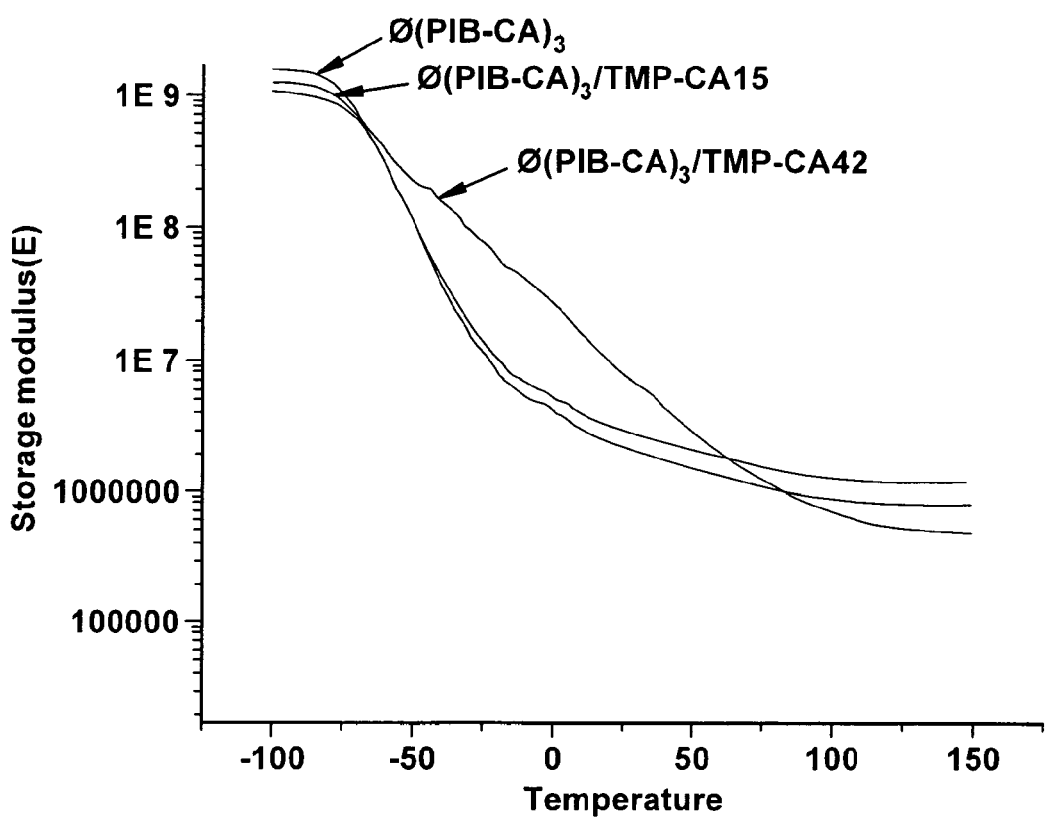
FIG. 28 is a graph illustrating the storage modulus versus temperature plot for various networks in accordance with the present invention.

The stiffness of networks and co-networks is compared by comparing the storage modulus of their films. FIG. 28 shows the storage modulus versus temperature plot for various networks. The storage moduli of the Ø(PIB-CA)$_3$ network, and the Ø(PIB-CA)$_3$/TMP-CA15 and Ø(PIB-CA)$_3$/TMP-CA42 co-networks decrease with increasing temperature. The storage moduli of the various materials is very similar at low temperatures. Due to hardening by poly(TMP-CA) sequences, the Ø(PIB-CA)$_3$/TMP-CA42 co-network exhibits a much slower relaxation in the glassy transition zone than the Ø(PIB-CA)$_3$ network and the Ø(PIB-CA)$_3$/IMP-CA15 co-network.

Figure 29:
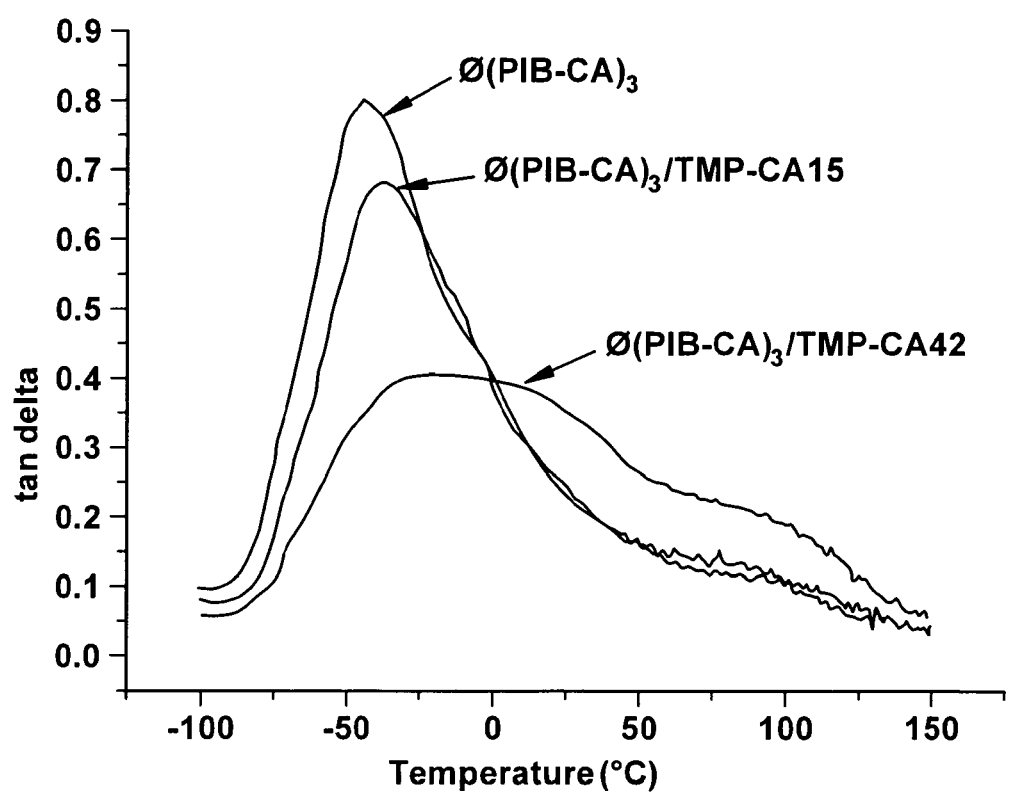
FIG. 29 is a graph illustrating tan (δ) versus temperature plots indicating the T$_g$s of a Ø(PIB-CA)$_3$ network and two Ø(PIB-CA)$_3$/TMP-CA co-networks.

FIG. 29 shows tan δ versus temperature plots indicating the T$_g$s of a Ø(PIB-CA)$_3$ network and two Ø(PIB-CA)$_3$/TMP-CA co-networks, and Table 21 summarizes the data together with theoretical T$_g$'s calculated by the Fox equation. The T$_g$ of the co-network made with 15% TMP-CA is close to the theoretical value, indicating a statistical copolymer, and corroborating our view of the polymerization mechanism. The calculated T$_g$ of the copolymer made with 42% TMP-CA is within the expected range, however, the experimental T$_g$ range is broad indicating a mixture of species.

TABLE 21

Glass Transition Temperatures of a Ø(PIB-CA)₃
Network, Two Ø(PIB-CA)₃/TMP-CA Co-Networks, and Poly(TMP-CA)

| | | | $T_g$ (° C.) | |
|---|---|---|---|---|
| | TMP-CA | | | Calculated by |
| Network/Polymer | Wt % | Mole % | Experimental | Fox Equation |
| Ø(PIB-CA)₃* | — | — | −38 | — |
| Ø(PIB-CA)₃/TMP-CA15* | 15 | 47 | −34 | −30 |
| Ø(PIB-CA)₃/TMP-CA42* | 42 | 76 | −35 to 35 broad range | −15 |
| Poly(TMP-CA)** | — | — | 35 | — |

CONCLUSIONS

Bulk polymerization of Ø(PIB-CA)₃ and bulk copolymerization of Ø(PIB-CA)₃/TMP-CA charges initiated by strong nucleophiles, e.g., Ø(PIB-NEt₂)₂ or 3, carried out in double-syringes by the reaction injection molding (RIM) technique instantaneously produce PIB networks and PIB/poly(TMP-CA) co-networks. Under well-defined conditions materials exhibiting a combination of promising properties for biomedical application are prepared.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. An injectible functionalized polyisobutylene compound comprising:
   a core structure having at least three polyisobutylene arms connected thereto,
   wherein each of the polyisobutylene arms contain a pendant group selected from a cyanoacrylate group, a —NH₂ group, a -NEt₂ group.

2. The injectible functionalized polyisobutylene compound of claim 1, wherein the number of polyisobutylene arms is between 4 and 6.

3. The injectible functionalized polyisobutylene compound of claim 1, wherein the number of polyisobutylene arms is at least 7.

4. The injectible functionalized polyisobutylene compound of claim 1, wherein the core structure is a benzene ring.

5. The injectible functionalized polyisobutylene compound of claim 1, wherein the core structure is selected from cyclic structures or non-cyclic structures that can be, at a minimum, tri-substituted.

6. The injectible functionalized polyisobutylene compound of claim 5, wherein the core structure is selected from a cycloalkane structure, a cycloalkene structure, or an aromatic structure.

7. The injectible functionalized polyisobutylene compound of claim 1, wherein the $M_n$ of the compound is in the range of about 1,500 g/mole to about 4,500 g/mole.

8. The injectible functionalized polyisobutylene compound of claim 1, wherein the $M_n$ of the compound is in the range of about 2,000 g/mole to about 3,500 g/mole.

9. The injectible functionalized polyisobutylene compound of claim 1, wherein the $M_n$ of the compound is in the range of about 2,200 g/mole to about 3,300 g/mole.

10. The injectible functionalized polyisobutylene compound of claim 1, wherein the $M_n$ of the compound is in the range of about 2,500 g/mole to about 3,000 g/mole.

11. The injectible functionalized polyisobutylene compound of claim 1, wherein each of the polyisobutylene arms contain a pendant cyanoacrylate group.

12. The injectible functionalized polyisobutylene compound of claim 1, wherein each of the polyisobutylene arms contain a pendant —NH₂ group.

13. The injectible functionalized polyisobutylene compound of claim 1, wherein each of the polyisobutylene arms contain a pendant -NEt₂ group.

14. An injectible functionalized polyisobutylene compound comprising:
    a core structure having at least three polyisobutylene arms connected thereto,
    wherein each of the polyisobutylene arms contain a pendant cyanoacrylate group and wherein the $M_n$ of the compound is in the range of about 1,500 g/mole to about 4,500 g/mole.

15. An injectible functionalized polyisobutylene compound comprising:
    a core structure having at least three polyisobutylene arms connected thereto,
    wherein each of the polyisobutylene arms contain a pendant —NH₂ group and wherein the $M_n$ of the compound is in the range of about 1,500 g/mole to about 4,500 g/mole.

16. An injectible functionalized polyisobutylene compound comprising:
    a core structure having at least three polyisobutylene arms connected thereto,
    wherein each of the polyisobutylene arms contain a pendant -NEt₂ group and wherein the $M_n$ of the compound is in the range of about 1,500 g/mole to about 4,500 g/mole.

17. A method for forming a network from an injectible functionalized polyisobutylene compound, the method comprising the steps of:
    (A) combining at least one injectible functionalized polyisobutylene compound and at least one initiator compound, wherein the at least one injectible functionalized polyisobutylene compound comprises a core structure having at least three polyisobutylene arms connected thereto and wherein each of the polyisobutylene arms contain a pendant group selected from a cyanoacrylate group, a —NH₂ group, a -NEt₂ group;
    (B) loading the combination of the at least one injectible functionalized polyisobutylene compound and at least one initiator compound into an injection device; and
    (C) injecting the combination of the at least one injectible functionalized polyisobutylene compound and at least one initiator compound into an environment suitable to cause the formation of a polymer network.

18. The method of claim 17, wherein the number of polyisobutylene arms is between 4 and 6.

19. The method of claim 17, wherein the number of polyisobutylene arms is at least 7.

20. The method of claim 17, wherein the core structure is a benzene ring.

21. The method of claim 17, wherein the core structure is selected from cyclic structures or non-cyclic structures that can be, at a minimum, tri-substituted.

22. The method of claim 21, wherein the core structure is selected from a cycloalkane structure, a cycloalkene structure, or an aromatic structure.

23. The method of claim 17, wherein the $M_n$ of the compound is in the range of about 1,500 g/mole to about 4,500 g/mole.

24. The method of claim 17, wherein the $M_n$ of the compound is in the range of about 2,000 g/mole to about 3,500 g/mole.

25. The method of claim 17, wherein the $M_n$ of the compound is in the range of about 2,200 g/mole to about 3,300 g/mole.

26. The method of claim 17, wherein the $M_n$ of the compound is in the range of about 2,500 g/mole to about 3,000 g/mole.

27. The method of claim 17, wherein each of the polyisobutylene arms contain a pendant cyanoacrylate group.

28. The method of claim 17, wherein each of the polyisobutylene arms contain a pendant $NH_2$ group.

29. The method of claim 17, wherein each of the polyisobutylene arms contain a pendant -$NEt_2$ group.

30. An injectible functionalized polyisobutylene blend comprising:
a first functionalized polyisobutylene compound comprising a core structure having at least three polyisobutylene arms connected thereto,
wherein each of the polyisobutylene arms contain a pendant cyanoacrylate group; and
a second functionalized polyisobutylene compound comprising a core structure having at least three polyisobutylene arms connected thereto,
wherein each of the polyisobutylene arms contain a pendant group selected from a —$NH_2$ group and a -$NEt_2$ group.

31. The method of claim 17, wherein the at least one injectible functionalized polyisobutylene compound comprises a core structure having at least three polyisobutylene arms connected thereto, wherein each of the polyisobutylene arms contain a pendant cyanoacrylate group; and wherein the at least one initiator compound comprises a second functionalized polyisobutylene compound comprising a core structure having at least three polyisobutylene arms connected thereto, wherein each of the polyisobutylene arms contain a pendant group selected from a —$NH_2$ group and a -$NEt_2$ group.

32. The injectible functionalized polyisobutylene blend of claim 30, wherein the first functionalized polyisobutylene compound and the second functionalized polyisobutylene compound each have an $M_n$ in the range of about 1,500 g/mole to about 4,500 g/mole.

* * * * *